United States Patent
Dunn

(10) Patent No.: US 11,116,928 B2
(45) Date of Patent: Sep. 14, 2021

(54) POSITIONING AND STABILISING STRUCTURE FOR A PATIENT INTERFACE SYSTEM

(71) Applicant: ResMed Pty Ltd, Bella Vista (AU)

(72) Inventor: Jessica Lea Dunn, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 1888 days.

(21) Appl. No.: 14/442,967

(22) PCT Filed: Nov. 15, 2013

(86) PCT No.: PCT/AU2013/001317
§ 371 (c)(1),
(2) Date: May 14, 2015

(87) PCT Pub. No.: WO2014/075141
PCT Pub. Date: May 22, 2014

(65) Prior Publication Data
US 2015/0290415 A1    Oct. 15, 2015

(30) Foreign Application Priority Data

Nov. 16, 2012  (AU) .............................. 2012904982

(51) Int. Cl.
*A61M 16/06*  (2006.01)
*A61M 16/00*  (2006.01)
(Continued)

(52) U.S. Cl.
CPC .... *A61M 16/0683* (2013.01); *A61M 16/0057* (2013.01); *A61M 16/0069* (2014.02);
(Continued)

(58) Field of Classification Search
CPC .......... A61M 16/0633; A61M 16/0666; A61M 16/0683; A61M 16/0616; A42B 3/14; A42B 3/142; A42B 3/145; A42B 3/147
See application file for complete search history.

(56) References Cited

U.S. PATENT DOCUMENTS

| 3,416,521 A | 12/1968 | Humphrey |
| 3,792,702 A * | 2/1974 | Delest .................. A62B 18/084 128/207.11 |

(Continued)

FOREIGN PATENT DOCUMENTS

| EP | 1 293 227 | 3/2003 |
| GB | 2 478 305 | 9/2011 |

(Continued)

OTHER PUBLICATIONS

"Respiratory Physiology", by John B. West, Lippincott Williams & Wilkins, 9th edition published 2011 (8 pages).
(Continued)

*Primary Examiner* — Colin W Stuart
*Assistant Examiner* — Douglas Y Sul
(74) *Attorney, Agent, or Firm* — Nixon & Vanderhye P.C.

(57) ABSTRACT

A patient interface system to treat sleep disordered breathing of a patient with pressurized gas, comprising: a patient interface; at least one strap; at least one retractor fixedly attached to the patient interface, said at least one retractor connected to the at least one strap and configured to retract the at least one strap without patient actuation; and at least one pad to cushion a rearward portion of the patient's head, said at least one pad having an opening, wherein said at least one strap passes through said opening to allow the at least one pad to move freely relative to said at least one strap.

33 Claims, 45 Drawing Sheets

(51) Int. Cl.
*A61M 16/20* (2006.01)
*A61M 16/08* (2006.01)
*A61M 16/10* (2006.01)
*A61M 16/16* (2006.01)

(52) U.S. Cl.
CPC .... *A61M 16/0616* (2014.02); *A61M 16/0875* (2013.01); *A61M 16/06* (2013.01); *A61M 16/0633* (2014.02); *A61M 16/0666* (2013.01); *A61M 16/0825* (2014.02); *A61M 16/0858* (2014.02); *A61M 16/107* (2014.02); *A61M 16/1055* (2013.01); *A61M 16/16* (2013.01); *A61M 16/208* (2013.01); *A61M 2016/0021* (2013.01); *A61M 2016/0027* (2013.01); *A61M 2016/0039* (2013.01); *A61M 2016/103* (2013.01); *A61M 2016/1025* (2013.01); *A61M 2202/0208* (2013.01); *A61M 2202/0225* (2013.01); *A61M 2205/21* (2013.01); *A61M 2205/3375* (2013.01); *A61M 2205/42* (2013.01); *A61M 2209/088* (2013.01); *A61M 2230/202* (2013.01); *A61M 2230/205* (2013.01); *A61M 2230/63* (2013.01)

(56) References Cited

U.S. PATENT DOCUMENTS

| | | | |
|---|---|---|---|
| 3,850,168 A * | 11/1974 | Ferguson | A62B 18/084 128/206.27 |
| 4,437,462 A | 3/1984 | Pijay et al. | |
| 4,782,832 A | 11/1988 | Trimble et al. | |
| 4,944,310 A | 7/1990 | Sullivan | |
| 5,687,425 A * | 11/1997 | Blosser | A42B 1/22 2/181.4 |
| 6,532,959 B1 | 3/2003 | Berthon-Jones | |
| 6,581,594 B1 | 6/2003 | Drew et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 2003/0051732 A1* | 3/2003 | Smith | A61M 16/06 128/206.27 |
| 2005/0172969 A1* | 8/2005 | Ging | A61M 16/0825 128/206.24 |
| 2007/0089749 A1* | 4/2007 | Ho | A61M 16/0616 128/207.18 |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2011/0023874 A1 | 2/2011 | Bath et al. | |
| 2012/0304999 A1* | 12/2012 | Swift | A61M 16/06 128/205.25 |
| 2013/0118500 A1* | 5/2013 | Stevens | A61M 16/024 128/205.25 |
| 2013/0312760 A1* | 11/2013 | Kostyk | A61M 16/0683 128/207.18 |
| 2015/0165152 A1* | 6/2015 | Haibach | A62B 18/084 128/206.21 |
| 2015/0174355 A1* | 6/2015 | Willard | A61M 16/0605 128/202.13 |
| 2015/0283349 A1* | 10/2015 | McLaren | A61M 16/06 128/206.21 |

FOREIGN PATENT DOCUMENTS

| | | |
|---|---|---|
| WO | WO1998004310 | 2/1998 |
| WO | WO1998034665 | 8/1998 |
| WO | WO2000078381 | 12/2000 |
| WO | WO2004073778 | 9/2004 |
| WO | WO2005063328 | 7/2005 |
| WO | WO2006074513 | 7/2006 |
| WO | WO2006130903 | 12/2006 |
| WO | WO2009052560 | 4/2009 |
| WO | WO2010135785 | 12/2010 |
| WO | 2011/077254 | 6/2011 |
| WO | WO 2012/000973 | 1/2012 |
| WO | WO2012171072 | 12/2012 |
| WO | WO2013020167 | 2/2013 |

OTHER PUBLICATIONS

First Examination Report issued in related New Zealand Application No. 630754 dated Jul. 1, 2015, 2 pages.
Notification Concerning Transmittal of International Preliminary Report on Patentability (Chapter I of the Patent Cooperation Treaty) for Application No. PCT/AU2013/001317, issued in related PCT case, dated May 28, 2015, (8 pages).
International Search Report for PCT/AU2013/001317 dated Feb. 3, 2014, four pages.
Written Opinion of the ISA for PCT/AU2013/001317 dated Feb. 3, 2014, six pages.
European Search Report issued in related European Application No. 13 85 4417.6 dated May 11, 2016, 8 pages.
First Examination Report issued in related New Zealand Application No. 742150 dated May 22, 2018, 1 page.

* cited by examiner

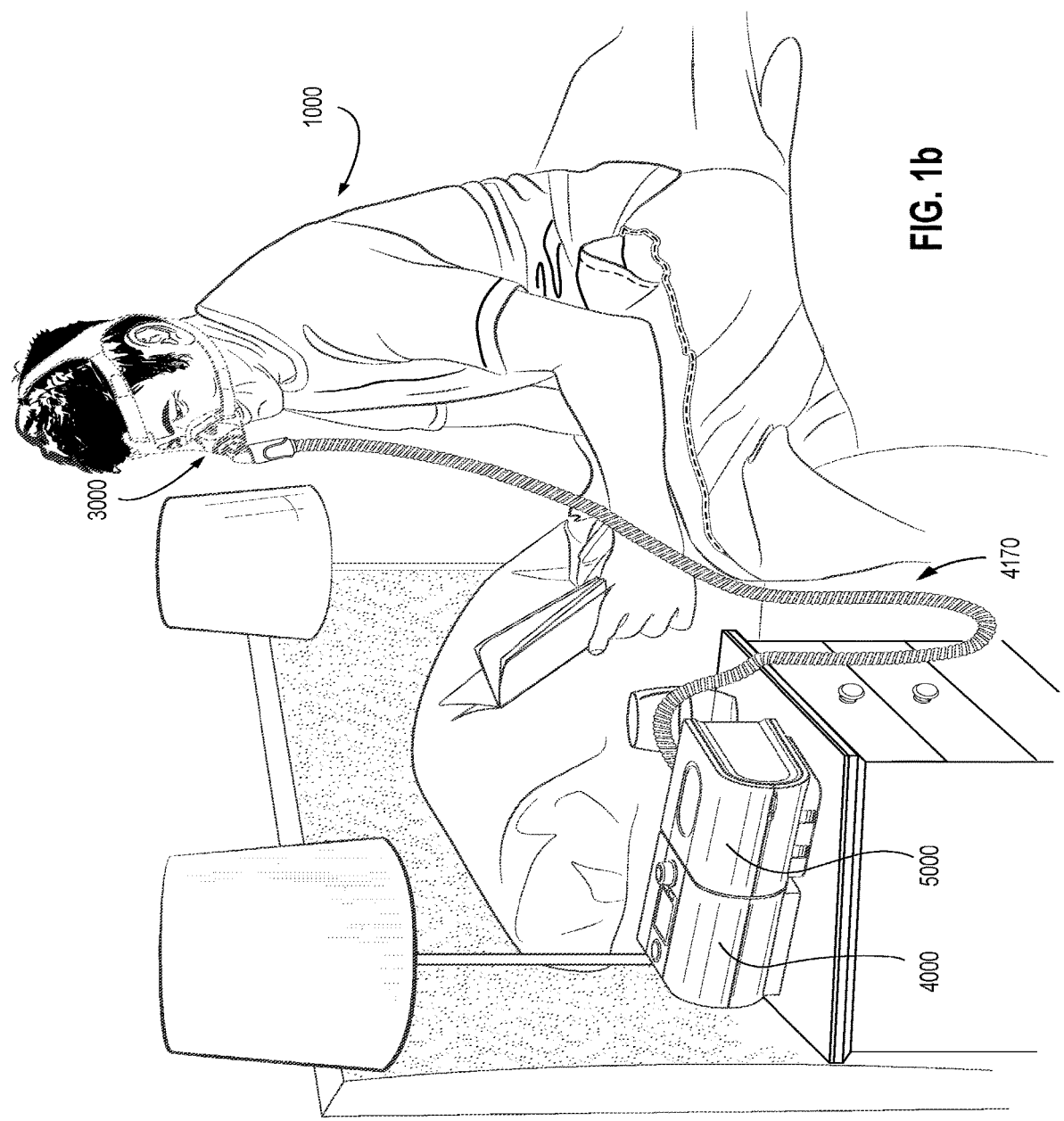

POSITIONING AND STABILISING STRUCTURE FOR A PATIENT INTERFACE SYSTEM

1 CROSS-REFERENCE TO RELATED APPLICATIONS

This application is the U.S. national phase of International Application No. PCT/AU2013/001317 filed 15 Nov. 2013 which designated the U.S. and claims the benefit of Australian Provisional Application No. 2012904982 filed 16 Nov. 2012, the entire contents of each of which are hereby incorporated by reference.

2 BACKGROUND OF THE TECHNOLOGY

2.1 Field of the Technology

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders.

2.2 Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

2.2.1 Systems

One known product used for treating sleep disordered breathing is the S9 Sleep Therapy System, manufactured by ResMed. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilator support to a patient through the upper airways to assist the patient in taking a full breath and/or maintain adequate oxygen levels in the body. The ventilator support is provided by a mask or nasal interface. NIV has been used to treat OHS, COPD, MD and Chest Wall disorders.

Invasive ventilation (IV) provides ventilatory support to patients that are no longer able to effectively breathe themselves and is provided using a tracheotomy tube.

Ventilators also control the timing and pressure of breaths pumped into the patient and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

2.2.3 Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping or throughout the day A tracheotomy tube is another form of patient interface that may be used for invasive ventilation.

2.2.3.1 Seal-Forming Portion

Patient interfaces typically include a seal-forming portion.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

2.2.3.2 Positioning and Stabilising

A seal-forming portion of a patient interface used for positive air pressure therapy is subject to the corresponding force of the air pressure to disrupt a seal. Thus, a variety of techniques have been used to position the seal-forming portion, and to maintain it in sealing relation with the appropriate portion of the face.

One technique is the use of adhesives. See, for example, US Patent publication US 2010/0000534.

Another technique is the use of one or more straps and stabilising harnesses. Many such harnesses suffer from being one or more of ill-fitting, bulky, uncomfortable and awkward to use.

2.2.3.3 Vent Technologies

Some forms of patient interface systems may include a vent to allow the washout of exhaled carbon dioxide. Many such vents are noisy. Others may block in use and provide insufficient washout. Some vents may be disruptive of the sleep of a bed-partner 1100 of the patient 1000, e.g. through noise or focused airflow.

ResMed Limited has developed a number of improved mask vent technologies. See WO 1998/034,665; WO 2000/078,381; U.S. Pat. No. 6,581,594; US Patent Application; US 2009/0050156; US Patent Application 2009/0044808.

Table of noise of prior masks (ISO 17510-2:2007, 10 cmH$_2$O pressure at 1 m )

| Mask name | Mask type | A-weighted sound power level dbA (uncertainty) | A-weighted sound pressure dbA (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed | nasal | 29 (3) | 22 (3) | 2008 |

-continued

| Mask name | Mask type | A-weighted sound power level dbA (uncertainty) | A-weighted sound pressure dbA (uncertainty) | Year (approx.) |
|---|---|---|---|---|
| Mirage SoftGel ResMed | nasal | 26 (3) | 18 (3) | 2010 |
| Mirage FX ResMed | nasal | 37 | 29 | 2004 |
| Mirage Swift (*) ResMed | pillows nasal | 28 (3) | 20 (3) | 2005 |
| Mirage Swift II ResMed | pillows nasal | 25 (3) | 17 (3) | 2008 |
| Mirage Swift LT | pillows | | | |

((*) one specimen only, measured using test method specified in ISO3744 in CPAP mode at 10 cmH$_2$O)

Sound pressure values of a variety of objects are listed below

| Object | A-weighted sound pressure dbA (uncertainty) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.3.4 Nasal Pillow Technologies

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063, 328 and WO 2006/130,903 (describing amongst other things aspects of ResMed LIBERTY full-face mask); International Patent Application WO 2009/052,560 (describing amongst other things aspects of ResMed SWIFT FX nasal pillows).

2.2.4 PAP Device

The air at positive pressure may be supplied to the airway of a patient by a PAP device such as a motor-driven blower. The outlet of the blower is connected via a flexible delivery conduit to a patient interface as described above.

Ventilators typically include a flow generator, an inlet filter, a patient interface, an air delivery conduit connecting the flow generator to the patient interface, various sensors and a microprocessor-based controller. The patient interface may include a mask or a tracheotomy tube as described above. The flow generator may include a servo-controlled motor, volute and an impeller that forms a blower. In some cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the flow generator may also include a valve capable of discharging generated air to atmosphere as a means for altering the pressure delivered to the patient as an alternative to motor speed control. The sensors measure, amongst other things, motor speed, mass flow rate and outlet pressure, such as with a pressure transducer or the like. The apparatus may optionally include a humidifier and/or heater elements in the path of the air delivery circuit. The controller may include data storage capacity with or without integrated data retrieval and display functions.

2.2.5 Humidifier

Respiratory apparatuses commonly have the ability to alter the humidity of the breathable gas in order to reduce drying of the patient's airway and consequent patient discomfort and associated complications. The use of a humidifier placed between the flow generator or PAP device or ventilator and the patient interface produces humidified gas that minimizes drying of the nasal mucosa and increases patient airway comfort. In addition in cooler climates, warm air applied generally to the face area in and about the patient interface is more comfortable than cold air.

Humidity refers to the quantity of water vapour present in the air. It is commonly measured in two ways:
  (1) Absolute Humidity (AH) is the actual content of water recorded in terms of weight per volume—usually in grams per cubic meter (g/m3) or milligrams per liter (mg/L).
  (2) Relative Humidity (RH) is a percentage expression of the actual water vapour content of a gas compared to its capacity to carry water at any given temperature.

The capacity of air to hold water vapour increases as the temperature of the air increases. This means that for air with a stable AH, the RH will decline as the temperature of the air is increased. Conversely, for air saturated with water (100% RH), if the temperature is reduced then the excess water will condense out. Air breathed by humans is generally naturally heated and humidified by the airway to reach a temperature of 37° C. and 100% humidity. At this temperature the AH humidity is 44 mg/L.

Respiratory humidifiers are available in many forms and may be a standalone device that is coupled to a respiratory device via a air delivery tube, is integrated with the respiratory device or configured to be directly coupled to the relevant respiratory apparatus. While passive humidifiers can provide some relief, generally a heated humidifier is required to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, a gas inlet to receive gas from the flow generator or PAP device, and a gas outlet adapted to be connected to an air delivery conduit that delivers the humidified gas to the patient interface.

Heated passover humidification is one common form of humidification used with a PAP device. In such systems the heating element may be incorporated in a heater plate which sits under, and is in thermal contact with, the water tub. Thus, heat is transferred from the heater plate to the water reservoir primarily by conduction. The air flow from the PAP device or flow generator or ventilator passes over the heated water in the water tub resulting in water vapour being taken up by the air flow. The ResMed H4i™ and H5i™ Humidifiers are examples of such heated passover humidification systems that are used in combination with ResMed S8 and S9 CPAP systems respectively.

Other humidification systems may also be used such as a bubble or diffuser humidifier, a jet humidifier or a wicking humidifier. In a bubble or diffuser humidifier the air is conducted below the surface of the water and allowed to bubble back to the top. A jet humidifier produces an aerosol of water and baffles or filters may be used so that the particles are either removed or evaporated before leaving the humidifier. A wicking humidifier uses a water absorbing material, such as sponge or paper, to absorb water by capillary action. The water absorbing material is placed within or adjacent at least a portion of the air flow path to allow evaporation of the water in the absorbing material to be taken up into the air flow.

An alternative form of humidification is provided by the ResMed HumiCare™ D900 humidifier that uses a Counter-Stream™ technology that directs the air flow over a large surface area in a first direction whilst supplying heated water to the large surface area in a second opposite direction. The ResMed HumiCare™ D900 humidifier may be used with a range of invasive and non-invasive ventilators.

2.2.6 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and include a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a user's mouth the mandible is held in an advanced position. The length of the connecting rods may be adjusted to change the level of protrusion of the mandible. A dentist may determine a preferred level of protrusion for the mandible that will determine the length of the connecting rods.

Some MRDs are structured to push that mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

3. BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

Another aspect of one form of the present technology is a patient interface that is moulded or otherwise constructed with a clearly defined perimeter shape which is intended to match that of an intended wearer.

Another aspect of the technology relates to retractable positioning and stabilizing structure for use with respiratory patient interfaces and its method of use in patient ventilation.

Another aspect of the technology is directed towards a retractable positioning and stabilizing structure that comprises a mechanical means adapted to extend and retract straps of the positioning and stabilizing structure without relying solely on elastic properties of the strap material.

Another aspect of the present technology is directed to a retractable CPAP mask. The retractable CPAP mask according to this aspect of the present technology may be retractable without actuation by the patient and/or the retractable CPAP mask may be automatically retractable.

Another aspect of the technology is directed towards a retractable headgear capable of extending to fit 100% of the population and retracting to provide sufficient force to create an effective seal to a patient's face while remaining less than the force required to cause discomfort.

Another aspect of the technology is directed towards a retractable positioning and stabilizing structure that provides a force displacement curve that is substantially flat in a defined range, wherein the force is a measure of force between the patient interface and the patient's face and displacement is a measure of the length of the straps. The force may be defined as the force sufficient to create an effective seal while avoiding discomfort, whereas the displacement may be defined as a length that the straps are capable of extending that is sufficient to fit all head sizes while maintaining an effective seal force that is less than the force required for discomfort.

Another aspect of the technology is directed towards retractable positioning and stabilizing structure that comprises a retractable cord or strap mechanism that may automatically retract to store a strap or cord within. The retractable mechanism may comprise a "retracting device" or a "retractor" that may comprise a housing section, wherein a cord or strap is capable of retracting into said housing automatically such that a portion of cable or strap, or a cable/strap connected member, such as a ring/hook remains outside the housing following full retraction. Said portion of excess cable/strap or connecting member that remains outside the housing may be referred to as the "pulling member". The pulling member of the retractable positioning and stabilizing structure may be capable of being pulled to extend the cord/strap out of the housing by a user and automatically retract when released. The automatic retraction of the cord/strap may be via a spring coil mechanism.

Another aspect of the technology is directed towards a retractable positioning and stabilizing structure wherein at least one end of the retractable positioning and stabilizing structure may be connected to one end of the patient interface and the other end may be attached to another end of said patient interface such that the retractable positioning and stabilizing structure strap/cord may be extended around the user's head and released to automatically fit the patient interface to said user's face.

The retractable device of the retractable positioning and stabilizing structure may be connected to one end of the patient interface; the pulling member of the retractable positioning and stabilizing structure may be connected to another end of the patient interface such that the cord or strap may be extendable by a user by holding the patient interface in one hand and pulling the retractable positioning and stabilizing structure away from said patient interface to extend the strap/cord.

The device may include have the positioning and stabilizing structure cord/strap coming out of the case from one location in one direction only, with the other pulling member attached to the patient interface in another location.

Moreover the positioning and stabilizing structure may be adapted to be pulled over the head and released to allow the strap/cord to retract and automatically fit said user's face. That is, the positioning and stabilizing structure may be capable of retracting to a position that provides enough force to the patient interface to create an effective seal while avoiding excessive force that causes discomfort.

The strap/cord may be extendable to an extent that allows for a circumference capable of fitting around all head sizes.

Another aspect of the technology is directed towards an arrangement of the retractable positioning and stabilizing structure that allows for an asymmetrical arrangement to appear to retract in a symmetrical fashion. In order for the asymmetrical arrangement of the positioning and stabilizing structure to retract smoothly when in communication with a patient interface, a casing or pad or sock (having a smooth inner surface that allows the cord/strap to move freely within it) may be used as a holding location for the hand, therefore allowing the positioning and stabilizing structure strap/cord to be pulled over the head in a natural action.

A user may be capable of extending the strap/cord of said positioning and stabilizing structure by placing one hand on the connected patient interface and using the other hand to pull on said casing or sock for extension, or vice versa. As the cord becomes longer from one side of the patient interface, it may slide within the casing/sock/pad that serves as the pulling point. The casing or sock or pad may remain approximately in the middle of the extended cord/strap ensuring that about equal lengths of the cord/strap may be on either side of said casing or sock or pad, ultimately making an asymmetrical device appear to work in a symmetrical manner. Furthermore, the strap or cord may be extended by hand such that a user may extend the strap or cord around their heads then release the strap such that it automatically retracts into a fitted position.

Another aspect of the technology is directed towards an additional sock or casing or pad used to cover portions of the positioning and stabilizing structure strap/cord to prevent it from directly contacting the face. A further aspect of the technology is directed towards said additional sock or casing or pad being made from a soft material that prevents discomfort or irritation when in contact with a patient's face.

Another aspect of the technology is directed towards varying the location of the retractable device on the patient interface, such as on the front, top, or bottom of the patient interface, on the side of the patient interface, or on the side or back or top of the positioning and stabilizing structure.

The retractable device may be located anywhere where the patient would not be at risk of directly lying on the mechanism. It might also be located in the small of the neck such that said device does not affect a patient lying on their back as the device remains in the recess created by the natural curvature of the neck.

The retractable device may be of a flat-enough profile such that it is not too obtrusive to lie upon, or it may be covered, coated or overmoulded in a soft cushioning material, e.g., silicone, gel, textile or foam.

Another aspect of the technology is directed towards the configuration of the retractable positioning and stabilizing structure in communication with a patient interface, said retractable positioning and stabilizing structure may be capable of extending its straps/cords out in two or more directions, symmetrically. That is, there may be two retractable devices comprising housings connected to corresponding sides of a patient interface with a single continuous or two/more connected strap/cords running between the devices. This allows for the cable to retract and extend symmetrically from both the left and right side of the patient interface when in use.

Another aspect of the technology is directed towards a retractable positioning and stabilizing structure comprising two or more retracting mechanisms in the positioning and stabilizing structure component and patient interface arrangement. That is, the retractable positioning and stabilizing structure may comprise multiple retractable devices comprising extendable/retractable straps, wherein each strap could be of a fixed length and combined into one positioning and stabilizing structure arrangement with multiple extending/retracting vectors.

Another aspect of the technology is directed towards one retractable device, capable of extending and retracting in two or more directions, is located on the casing/sock of the retractable positioning and stabilizing structure. Said retractable device may comprise two or more pulling members capable of extending and retracting in opposite directions. Said pulling members may be capable of connecting to or being fixed on corresponding sides of a patient interface such that the patient interface may be pulled away from the retractable device to extend the straps and place the positioning and stabilizing structure over a users head while automatically positioning the patient interface.

The retractable device may comprise one continuous cable/strap that is capable of extending in two directions out of the same housing. Alternatively, the one retractable device may comprise two or more straps capable of extending in two or more directions from the same housing.

Another aspect of the technology is directed towards the retracting positioning and stabilizing structure capable of creating a variable diameter crown element to fit many different sized heads.

A further aspect of the technology is directed towards positioning and stabilizing structure strap/cord comprising various properties and materials. The positioning and stabilizing structure strap/cord could have a flat or a rounded profile, or a mostly flat with a rounded edge profile, i.e., obround.

In another aspect of the technology, the positioning and stabilizing structure strap could be made from a braided cord, or a woven tape, or a knitted narrow fabric.

In a further aspect of the technology, the positioning and stabilizing structure strap could be a textile, a polymer or a composite material.

In another aspect of the technology, the positioning and stabilizing structure strap could have in-built cushioning such as a 3D-spacer knit, or a foam or rubbery (e.g. silicone) inner core, or it could be a very narrow diameter (e.g. 1 mm) and be encased with a soft (e.g. textile or gel) sock or sheath around it to prevent facial marking on the patient.

In another aspect of the technology positioning and stabilizing structure strap/cord could be a hollow and/or tubular structure.

In a further aspect of the technology, the positioning and stabilizing structure strap could be bifurcated, that is, one strap divides into two sections in order to fit over the crown of the head, and then comes together as one strap again at the point of attachment to the patient interface or upon entry into the housing of the retractable device.

In another aspect of the technology, the retracting device comprises a ratchet mechanism whereby the positioning and stabilizing structure locks at a certain extension (or series of lengths) with a push-button to release the ratchet, returning the coil spring to a more relaxed state, thereby retracting the positioning and stabilizing structure strap.

In yet another aspect of the technology, if the positioning and stabilizing structure strap is flat, it could exit the casing in a continuous manner, or it could twist 90 degrees in order to better conform to the head.

In yet another aspect of the technology the positioning and stabilizing structure strap/cord could travel through a guide or tube in order to achieve the correct vector or anthropometric fit, e.g., in order to travel between the ears and the eyes. This tube or guide could be straight or curved.

Another aspect of the technology is directed towards the smaller compact size of the retractable positioning and stabilizing structure arrangement that is easier to transport and store.

Yet another aspect of the technology is directed towards the ease of use of the patient interface and retractable positioning and stabilizing structure relying on a natural extend and release action to automatically fit the patient interface and positioning and stabilizing structure.

Another aspect of the present technology is directed to a patient interface system to treat sleep disordered breathing of a patient with pressurized gas. The patient interface system may comprise: a patient interface; at least one strap; at least one retractor fixedly attached to the patient interface, said at least one retractor connected to the at least one strap and configured to retract the at least one strap without patient actuation; and at least one pad to cushion a rearward portion of the patient's head, said at least one pad having an opening, wherein said at least one strap passes through said opening to allow the at least one pad to move freely relative to said at least one strap.

In examples, (a) said at least one retractor may comprise a pair of retractors, each disposed on an opposite side of the patient interface, and each of the pair of retractors may be connected to a respective end of said at least one strap, (b) said at least one strap may comprise a single strap, each of the pair of retractors configured to retract a respective end of said single strap, and said single strap may pass above the patient's ears and below the patient's eyes when the patient interface system is donned by the patient, (c) said single strap may comprise a pair of bifurcation points, and said single strap may be split into a pair of rear straps at said pair of bifurcation points, (d) said at least one retractor may comprise a single retractor connected to a first end of the at least one strap and disposed on a first side of said patient interface, and a second end of said at least one strap may be fixedly attached to a second side of said patient interface, said second side being opposite said first side, (e) said at least one strap may comprise a single strap, and said single strap may pass above the patient's ears and below the patient's eyes when the patient interface system is donned by the patient, (f) said at least one retractor may comprise a first retractor and a second retractor, said first retractor disposed on the patient interface higher than the second retractor in a plane parallel to the patient's sagittal plane, said at least one strap may comprise a first strap and a second strap and said at least one pad comprises a first pad and a second pad, each corresponding to the first strap and the second strap, and the first retractor may be structured to retract both ends of the first strap and the second retractor is structured to retract both ends of the second strap, (g) said first strap may pass above the patient's ears and below the patient's eyes and, said second strap may pass below the patient's ears, when the patient interface system is donned on the patient, (h) said at least one retractor may comprise a single retractor disposed centrally on the patient interface in a horizontal plane, the at least one strap may comprise a single strap, and the single retractor may be structured to retract both ends of the single strap, (i) said single strap may pass above the patient's ears and below the patient's eyes when the patient interface system is donned by the patient, (j) the patient interface system may further comprise a pair of rigidiser arms, each disposed on an opposite side of said patient interface, each of the pair of rigidiser arms may be structured to allow the strap to pass freely therethrough such that tension force vectors of the strap are directed above the patient's ears and below the patient's eyes when the patient interface system is donned by the patient, (k) said pair of rigidiser arms may be deformable to substantially conform to the patient's face by flexing in a plane parallel to the patient's sagittal plane and in a plane parallel to the Frankfort horizontal, (l) the pair of rigidiser arms may comprise a first material and the patient interface may comprise a second material, the first material being less rigid than the second material, (m) said at least one strap may comprise a pair of straps, said at least one retractor may comprise a single retractor disposed centrally on the patient interface in a horizontal plane, said single retractor structured to retract both ends of each of the pair of straps, and a pair of sliders may be slidingly disposed on the pair of straps to provide a pair of adjustable bifurcation points between the pair of straps, (n) the patient interface system may further comprise additional pads to cushion the patient's cheeks against the at least one strap when said patient interface system is donned on the patient, the additional pads each comprise an additional pad opening, said at least one strap may pass through said additional pad opening to allow the additional pads to move freely relative to said at least one strap, (o) each of the additional pads may comprise a smooth surface on the additional pad opening to minimize friction between the additional pads and the at least one strap, (p) each of the additional pads may comprise a soft external material to prevent irritation of the patient's skin, (q) each at least one pad may comprise a smooth surface on the opening to minimize friction between the at least one pad and the at least one strap, (r) each at least one pad may comprise a soft external material to prevent irritation of the patient's skin, (s) each at least one retractor may be fixedly attached to the patient interface at a joint, (t) the joint may comprise a material that is less rigid than the patient interface, (u) the at least one strap may comprise an inelastic material, (v) the at least one strap may have a substantially rectangular cross-section, (w) the at least one strap may have a substantially circular cross-section, (x) the at least one strap may be hollow, (z) the at least one strap may comprise a braided cord, a woven tape, or a knitted narrow fabric, (aa) the at least one strap may comprise a textile, a polymer, or a composite material, (bb) the at least one strap may comprise built-in cushioning, (cc) the at least one strap may comprise a soft external material to prevent irritation of the patient's skin, (dd) the at least one retractor may be configured to retract the at least one strap with a retracting force of between about 2.2N and about 2.6N, (ee) the retracting force may be about 2.4N, (ff) the patient interface system may further comprise: a seal-forming structure structured to form a seal with the patient's airways; and a plenum chamber to connect the seal-forming structure to the patient interface, and/or (gg) the seal-forming structure may be structured to form a seal with the patient's nose and/or mouth.

Another aspect of the present technology is directed to a patient interface system to treat sleep disordered breathing of a patient with pressurized gas. The patient interface system may comprise: a patient interface; at least one strap; at least one cushion structured to at least partially conform to the patient's head; and at least one retractor fixedly attached to said at least one cushion, said at least one retractor connected to the at least one strap and configured to retract the at least one strap without patient actuation to urge the patient interface toward the patient's face.

In examples, (a) the at least one strap may comprise a pair of straps and the at least one retractor may comprises a pair of retractor, and a first end of each of the pair of straps may be fixedly attached to the patient interface and a second end of each of the pair of straps may be connected to a respective one of the pair of retractors, (b) the at least one cushion may comprise a one-piece crown cushion having a substantially circular shape, (c) each of the pair of straps may be fixedly attached to the patient interface by a rigidiser arm, (d) the rigidiser arm may be structured to direct a tension force vector of a respective strap above the patient's ears and below the patient's eyes when the patient interface system is donned by the patient, (e) said rigidiser arm may be deformable to substantially conform to the patient's face by flexing in a plane parallel to the patient's sagittal plane and in a plane parallel to the Frankfort horizontal, (f) the pair of rigidiser arms may comprise a first material and the patient interface may comprise a second material, the first material being less rigid than the second material, (e) the at least one cushion may comprise a top cushion and a rear cushion, said top cushion structured to at least partially conform to a top portion of the patient's head, and said rear cushion structured to at least partially conform to a rear portion of the patient's head, said top cushion may include a loop at each end, each of the pair of straps passing freely through a respective loop, and each of the pair of retractors may befixedly attached to the rear cushion at opposite ends, (f) each of the pair of straps may be fixedly attached to the patient interface by a rigidiser arm, (g) the rigidiser arm may be structured to direct a tension force vector of a respective strap above the patient's ears and below the patient's eyes when the patient interface system is donned by the patient, (h) said rigidiser arm may be deformable to substantially conform to the patient's face by flexing in a plane parallel to the patient's sagittal plane and in a plane parallel to the Frankfort horizontal, (i) the pair of rigidiser arms may comprise a first material and the patient interface may comprise a second material, the first material being less rigid than the second material, (j) the at least one retractor may comprise a pair of retractors, the at least one strap may comprise a pair of straps, and the at least cushion may comprise a retractor cushion and a guide cushion, the pair of retractors may be fixedly attached to the retractor cushion, each of the pair of retractors may be configured to retract both ends of a respective one of the pair of straps, and the guide cushion may be structured to direct a first strap of the pair of straps above the patient's ears and below the patient's eyes and to direct a second strap of the pair of straps below the patient's ears when the patient interface system is donned by the patient, (k) the at least one retractor may comprise a pair of retractors, the at least one strap may comprise a pair of straps, and the at least cushion may comprise a pair of retractor cushions, the pair of retractors may be fixedly attached to a respective one of the pair of retractor cushions, each of the pair of retractors may be configured to retract both ends of a respective one of the pair of straps, and a first strap of the pair of straps may be directed above the patient's ears and below the patient's eyes and a second strap of the pair of straps is directed below the patient's ears when the patient interface system is donned by the patient, (l) the at least one cushion may comprise a crown cushion, the at least one strap may comprise a pair of straps, each of the pair of straps may be connected to the patient interface at a first end, and the at least one retractor may comprise a single retractor disposed on the crown cushion such that the retractor is located above the patient's head when the patient interface system is donned by the patient, the retractor may be configured to retract a second end of each of the pair of straps, and the crown cushion may comprise a channel on each side of the retractor to direct a respective one of the pair of straps above the patient's ears and below the patient's eyes when the patient interface system is donned by the patient, (m) the at least one cushion may comprise a crown cushion, the at least one strap may comprise a single strap, and the at least one retractor may comprise a single retractor disposed on the crown cushion such that the retractor is located above the patient's head when the patient interface system is donned by the patient, the retractor may be configured to retract both ends of the strap, the patient interface system may comprise a pair of patient interface channels, each connected to an opposite side of the patient interface, and the strap passing freely through each of the pair of patient interface channels such that two portions of the strap are directed below the patient's eyes and above the patient's ears when the patient interface system is donned by the patient, and the crown cushion may comprise a cushion channel, the strap passing freely through the cushion channel such that two portions of the strap are directed below the patient's ears when the patient interface system is donned by the patient, (n) each of the pair of patient interface channels is spaced from the patient interface by an extension, (o) the at least one cushion may comprise a crown cushion, the at least one strap may comprise a pair of straps, each of the pair of straps may be connected to the patient interface at a first end, and the at least one retractor may comprise a single retractor disposed on the crown cushion such that the retractor is located above the patient's head when the patient interface system is donned by the patient, the retractor may be configured to retract a second end of each of the pair of straps, the patient interface may comprise a pair of patient interface channels, each disposed on an opposite side of the patient interface, and the strap passing freely through each of the pair of patient interface channels such that two portions of the strap are directed below the patient's eyes and above the patient's ears when the patient interface system is donned by the patient, and the crown cushion may comprise a pair of cushion channels, respective ones of the pair of straps passing freely through the cushion channel such that two portions of each of the pair of straps are directed below the patient's ears and each of the pair of straps is doubled back through a respective one of the pair of cushion channels when the patient interface system is donned by the patient, (p) the patient interface system may further comprise additional pads to cushion the patient's cheeks against the at least one strap when said patient interface system is donned on the patient, the additional pads each comprise an additional pad opening, said at least one strap may pass through said additional pad opening to allow the additional pads to move freely relative to said at least one strap, (q) each of the additional pads may comprise a smooth surface on the additional pad opening to minimize friction between the additional pads and the at least one strap, (r) each of the additional pads may comprise a soft external material to prevent irritation of the patient's skin, (s) each at least one cushion may comprises a smooth surface on the opening to minimize friction between the at least one cushion and the at least one strap, (t) each at least one cushion may comprise a soft external material to prevent irritation of the patient's skin, (u) the at least one strap may comprise an inelastic material, (v) the at least one strap may have a substantially rectangular cross-section, (w) the at least one strap may have a substantially circular cross-section, (x) the at least one strap may be hollow, (y) the at least one strap may comprise a braided cord, a woven tape, or a knitted narrow fabric, (z) the at least one strap may comprise a textile, a polymer, or a composite material, (aa) the at least one strap may comprise built-in cushioning, (bb) the at least one strap may comprise a soft external material to prevent irritation of the patient's skin, (cc) the at least one retractor may be configured to retract the at least one strap with a retracting force of between about 2.2N and about 2.6N, (dd) the retracting force may be about 2.4N, the patient interface system may further comprise: a seal-forming structure structured to form a seal with the patient's airways; and a plenum chamber to connect the seal-forming structure to the patient interface, and/or (ee) the seal-forming structure may be structured to form a seal with the patient's nose and/or mouth.

Another aspect of the present technology is directed to a patient interface system to treat sleep disordered breathing of a patient with pressurized gas. The patient interface system may comprise: a patient interface; a strap; a retractor fixedly attached to the patient interface, said retractor connected to the strap and configured to retract both ends of the strap without patient actuation; and a patient interface channel fixedly attached to the patient interface channel; and a cushion structured to at least partially conform to the patient's head, the cushion having a pair of cushion channels, wherein said strap passes freely through each of said cushion channels and the patient interface channel such that upper portions of the strap pass above the patient's ears and below the patient's eyes when donned by the patient and lower portions of the strap pass below the patient's ears when donned by the patient.

In examples, (a) the patient interface system may further comprise additional pads to cushion the patient's cheeks against the at least one strap when said patient interface system is donned on the patient, the additional pads each comprise an additional pad opening, and said at least one strap may pass through said additional pad opening to allow the additional pads to move freely relative to said at least one strap, (b) each of the additional pads may comprise a smooth surface on the additional pad opening to minimize friction between the additional pads and the at least one strap, (c) each of the additional pads may comprise a soft external material to prevent irritation of the patient's skin, (d) each cushion channel and patient interface channel may comprise a smooth internal surface to minimize friction with the strap, (e) the cushion may comprise a soft external material to prevent irritation of the patient's skin, (f) the retractor may be fixedly attached to the patient interface at a joint, (g) the joint may comprise a material that is less rigid than the patient interface, (h) the strap may comprise an inelastic material, (i) the strap may have a substantially rectangular cross-section, (j) the strap may have a substantially circular cross-section, (k) the strap may be hollow, (l) the strap may comprise a braided cord, a woven tape, or a knitted narrow fabric, (m) the strap may comprise a textile, a polymer, or a composite material, (n) the strap may comprise built-in cushioning, (o) the strap may comprise a soft external material to prevent irritation of the patient's skin, (p) the retractor may be configured to retract the at least one strap with a retracting force of between about 2.2N and about 2.6N, (q) the retracting force may be about 2.4N, (r) the patient interface system may further comprise: a seal-forming structure structured to form a seal with the patient's airways; and a plenum chamber to connect the seal-forming structure to the patient interface, and/or (s) the seal-forming structure is structured to form a seal with the patient's nose and/or mouth.

Another aspect of the present technology is directed to a patient interface system to treat sleep disordered breathing of a patient with pressurized gas. The patient interface system may comprise: a patient interface; a first strap and a second strap; a cushion structured to at least partially conform to the patient's head, the cushion having cushion channels; a patient interface channel fixedly attached to the patient interface channel; a first retractor fixedly attached to the patient interface and connected to both ends of the first strap to retract both ends of the first strap without patient actuation; and a second retractor fixedly attached to the cushion and connected to both ends of the second strap to retract both ends of the second strap without patient actuation, wherein said first strap passes freely through the patient interface channel such that the first strap pass above the patient's ears and below the patient's eyes and said second strap passes freely through said cushion channel and below the patient's ears when the patient interface is donned by the patient.

In examples, (a) patient interface system may further comprise additional pads to cushion the patient's cheeks against the first strap and the second strap when said patient interface system is donned on the patient, the additional pads each comprise an additional pad opening, and said first strap or the second strap may pass through said additional pad opening to allow the additional pads to move freely relative to said first strap or the second strap, (b) each of the additional pads may comprise a smooth surface on the additional pad opening to minimize friction between the additional pads and the first strap or the second strap, (c) each of the additional pads may comprise a soft external material to prevent irritation of the patient's skin, (d) each cushion channel and patient interface channel may comprise a smooth internal surface to minimize friction with the first strap or the second strap, (e) the cushion may comprise a soft external material to prevent irritation of the patient's skin, (f) the first retractor may be fixedly attached to the patient interface at a joint, (g) the joint may comprise a material that is less rigid than the patient interface, (h) the first strap and the second strap may comprise an inelastic material, (i) the first strap and the second strap may have a substantially rectangular cross-section, (j) the first strap and the second strap may have a substantially circular cross-section, (k) the first strap and the second strap may be hollow, (l) the first strap and the second strap may comprise a braided cord, a woven tape, or a knitted narrow fabric, (m) the first strap and the second strap may comprise a textile, a polymer, or a composite material, (n) the first strap and the second strap may comprise built-in cushioning, (o) the first strap and the second strap may comprise a soft external material to prevent irritation of the patient's skin, (p) the first retractor and the second retractor may be configured to retract the respective strap with a retracting force of between about 2.2N and about 2.6N, (q) the retracting force may be about 2.4N, (r) the patient interface system may further comprise: a seal-forming structure structured to form a seal with the patient's airways; and a plenum chamber to connect the seal-forming structure to the patient interface, and/or (s) the seal-forming structure may be structured to form a seal with the patient's nose and/or mouth.

An aspect of one form of the present technology is a method of manufacturing apparatus.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

4.1 Treatment Systems

FIG. 1a shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000.

4.2 Therapy

4.2.1 Respiratory System

Figure 1A:
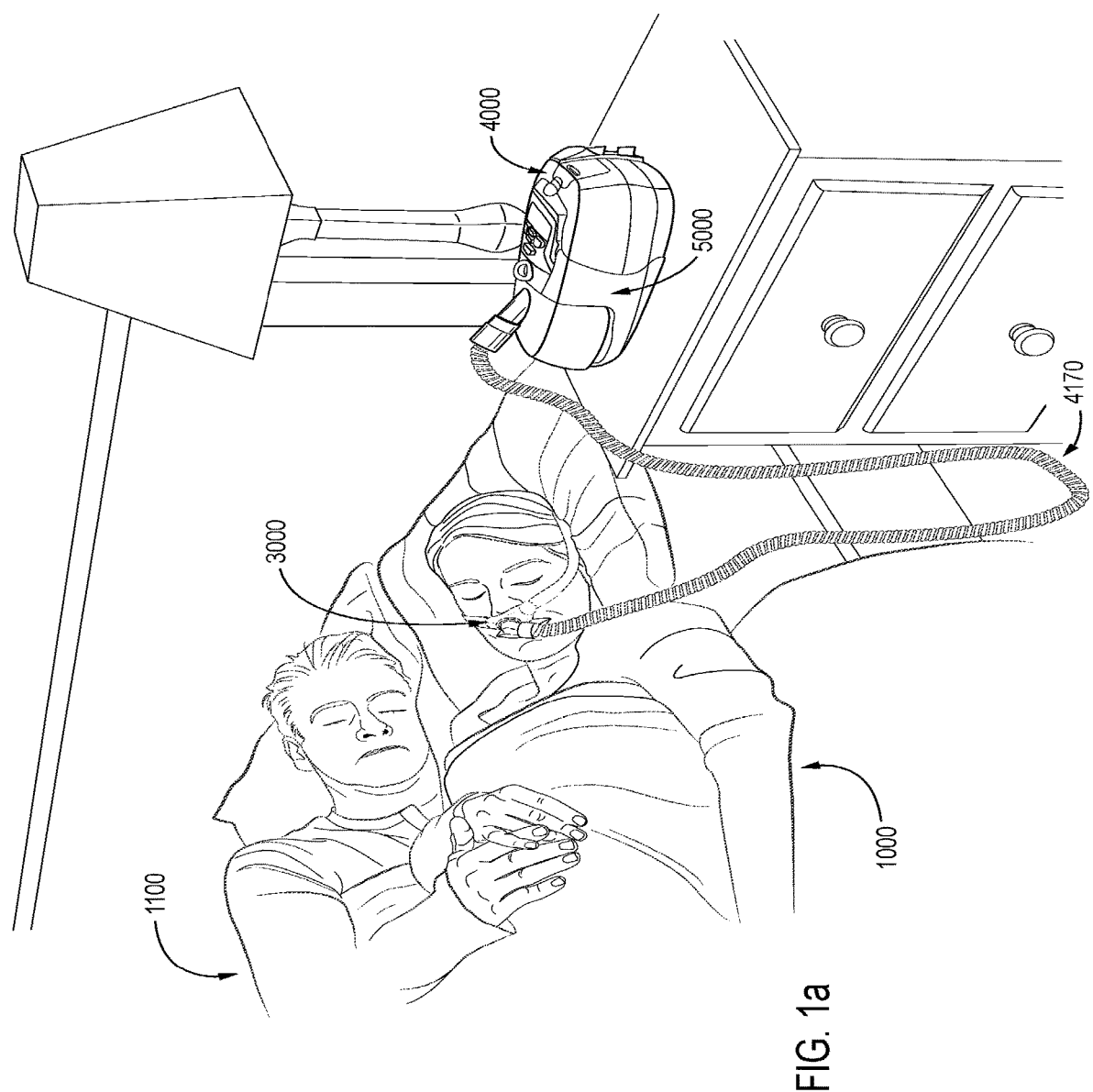
FIG. 1b shows a PAP device in use on a patient with a nasal mask.
FIG. 1c shows a PAP device in use on a patient with a full-face mask.
Figure 1C:
Figure 2A:
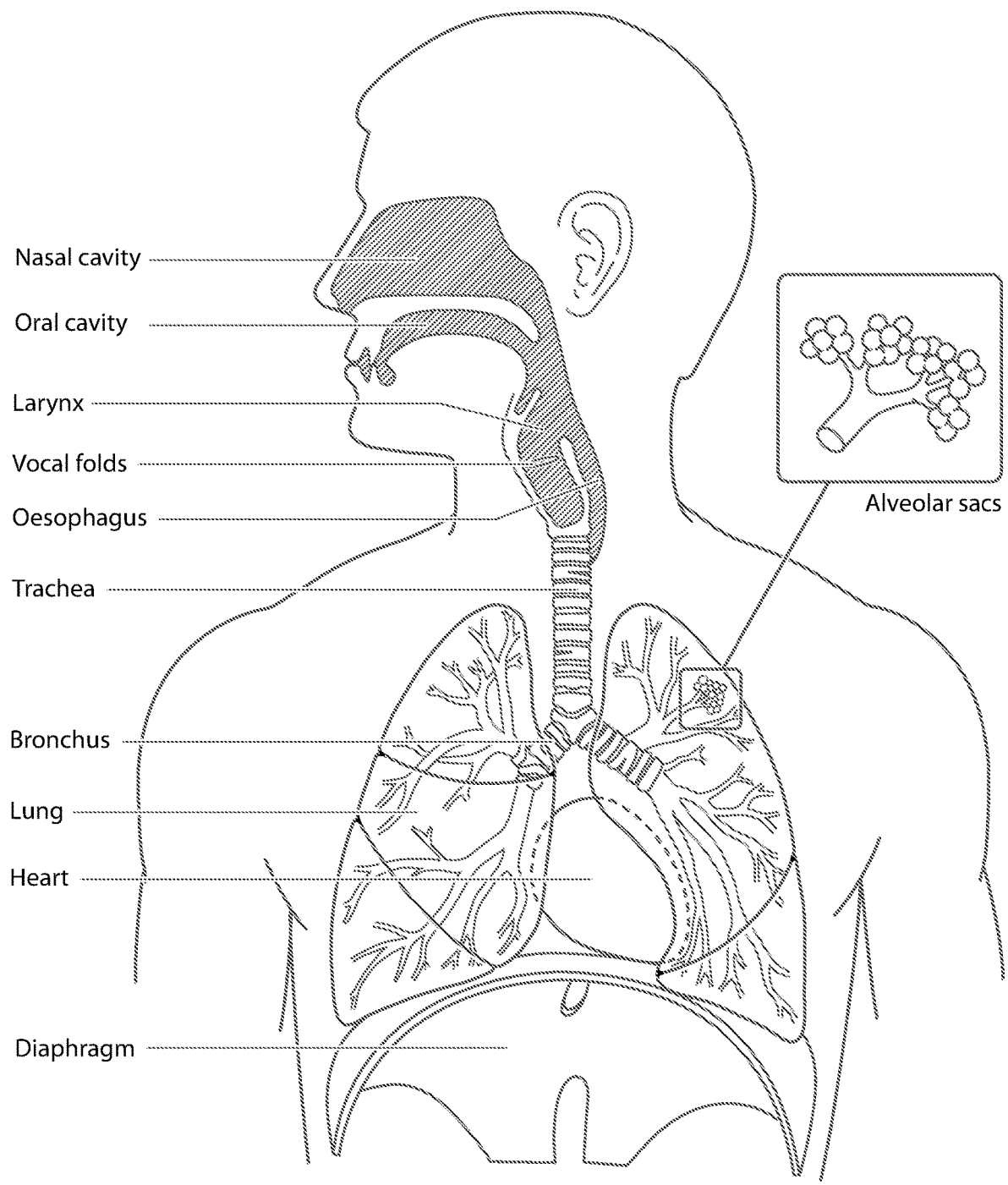

FIG. 2a shows an overview of a human respiratory system including the nasal and oral cavities, the larynx, vocal folds, esophagus, trachea, bronchus, lung, alveolar sacs, heart and diaphragm.

Figure 2B:
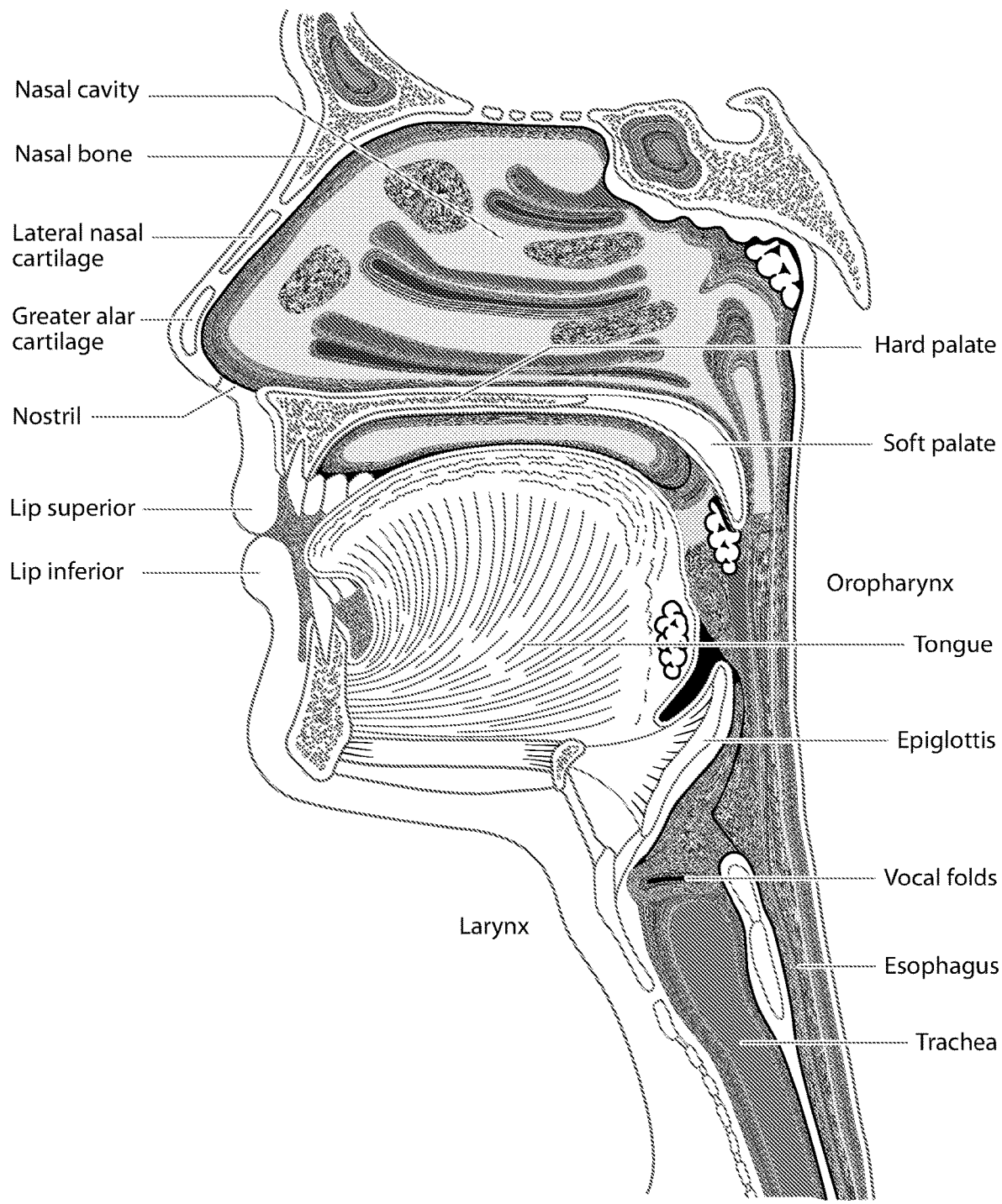

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, esophagus and trachea.

4.2.2 Facial Anatomy

Figure 2C:
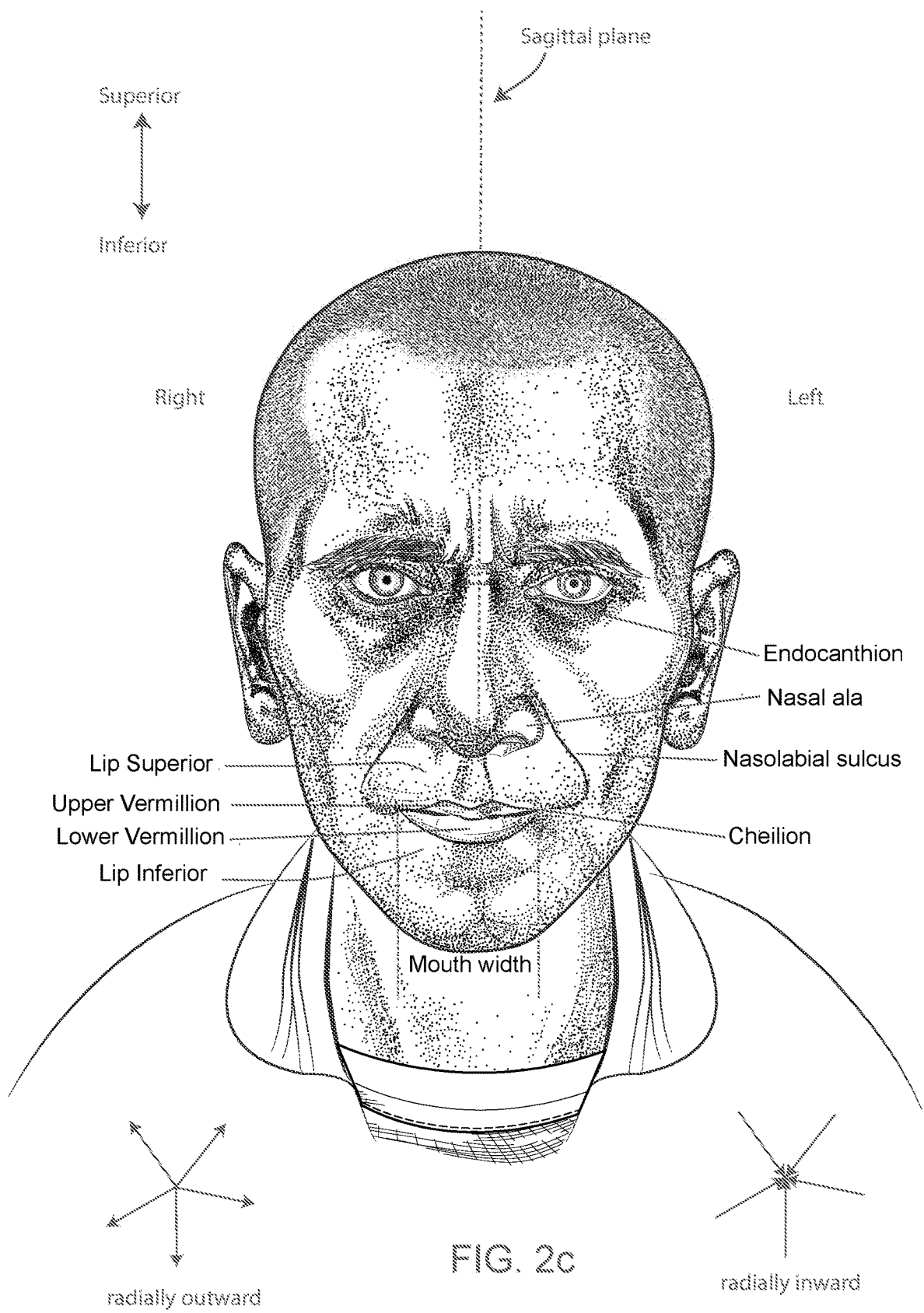

FIG. 2c is a front view of a face with several features of surface anatomy identified including the lip superior, upper vermillion, lower vermillion, lip inferior, mouth width, endocanthion, a nasal ala, nasolabial sulcus and cheilion.

FIG. 2d is a side view of a head with several features of surface anatomy identified including glabella, sellion, pronasale, subnasale, lip superior, lip inferior, supramenton, nasal ridge, otobasion superior and otobasion inferior. Also indicated are the directions superior & inferior, and anterior & posterior.

Figure 2G:
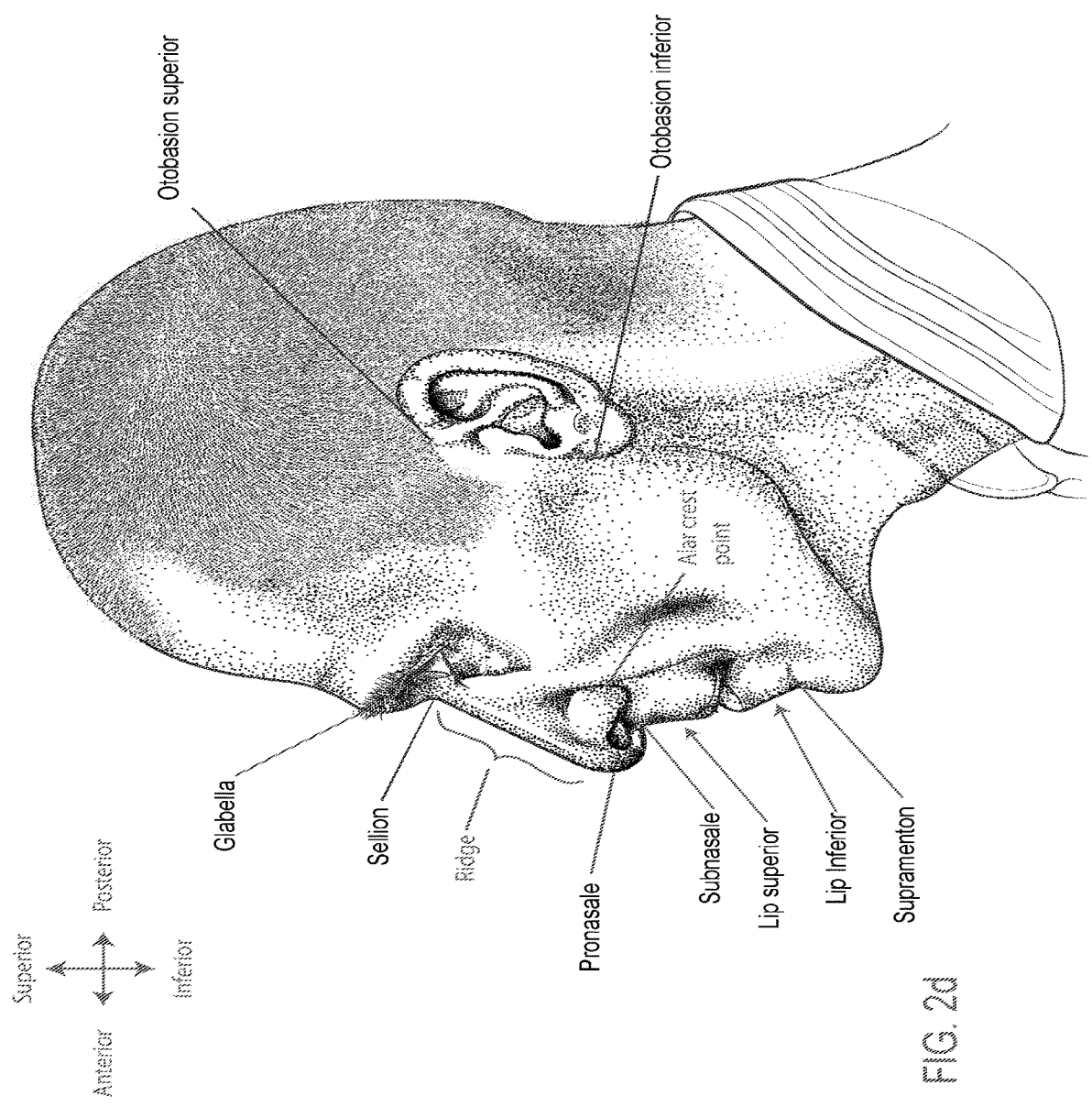
Figure 2E:
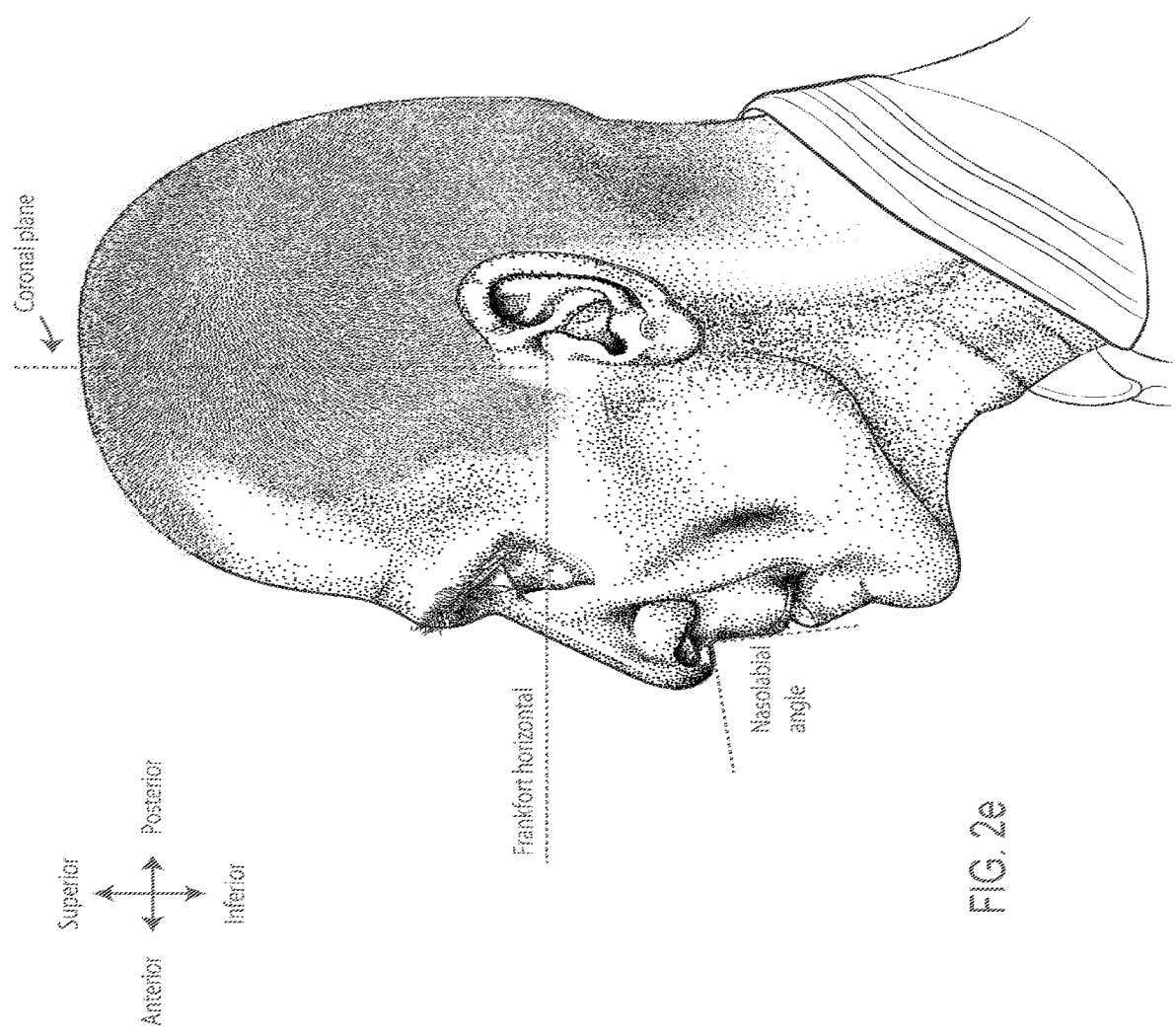

FIG. 2e is a further side view of a head. The approximate locations of the Frankfort horizontal and nasolabial angle are indicated.

Figure 2F:
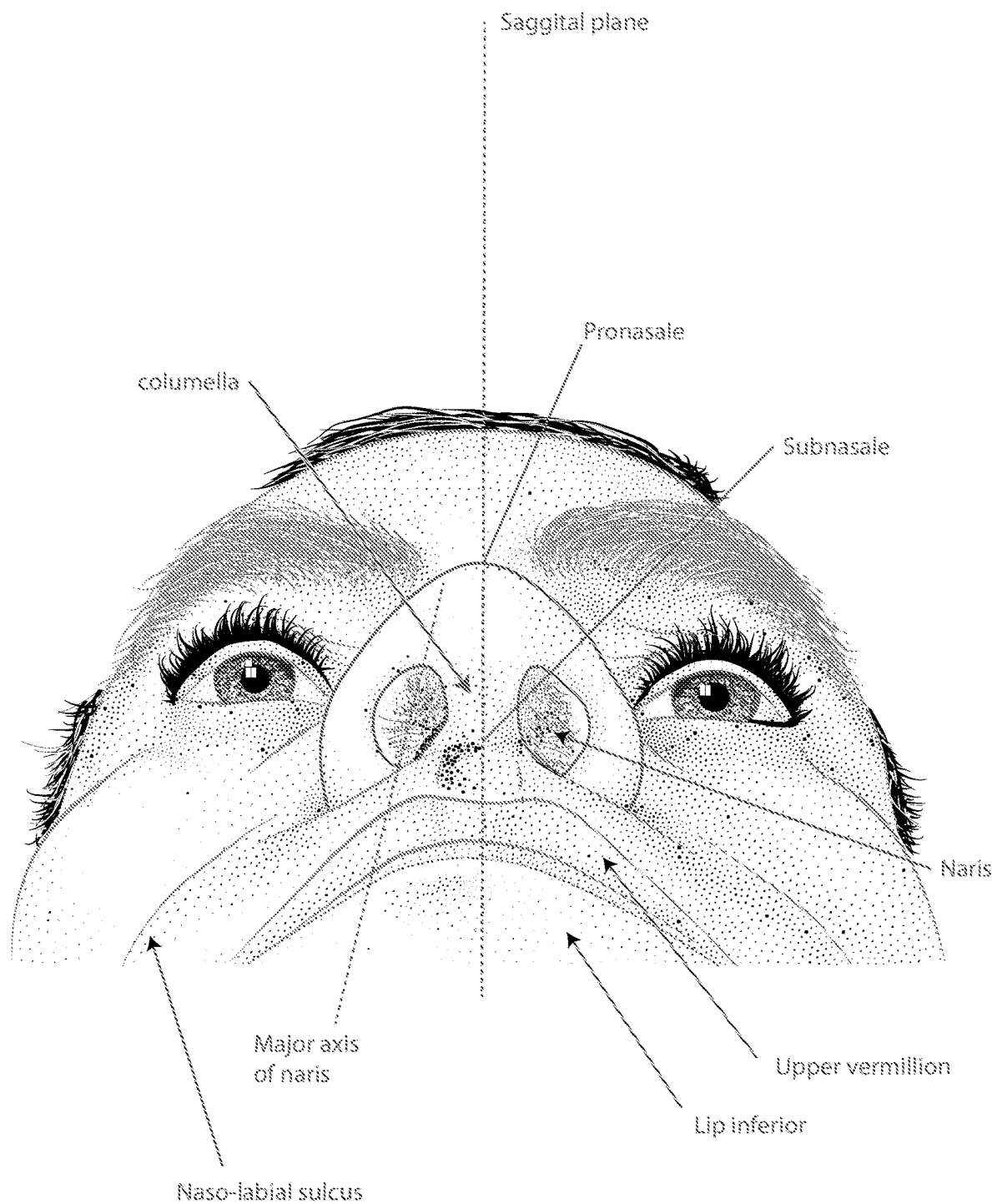

FIG. 2f shows a base view of a nose.

FIG. 2g shows a side view of the superficial features of a nose.

Figure 2I:
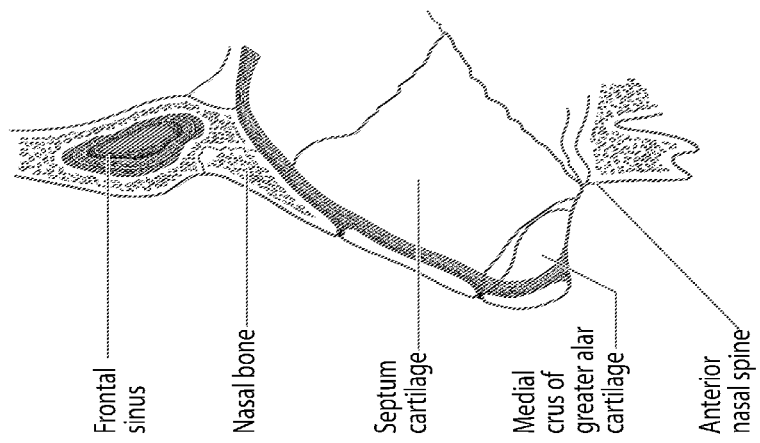
Figure 2H:
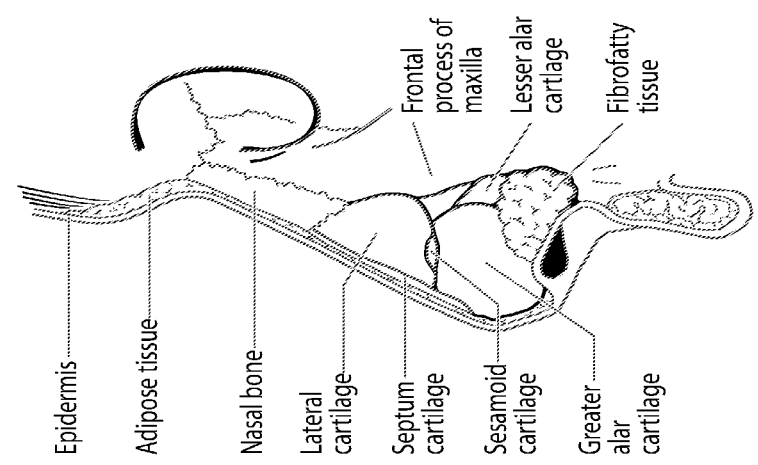
Figure 2G:

FIG. 2h shows subcutaneal structures of the nose, including lateral cartilage, septum cartilage, greater alar cartilage, lesser alar cartilage and fibrofatty tissue.

FIG. 2i shows a medial dissection of a nose, approximately several millimeters from a sagittal plane, amongst other things showing the septum cartilage and medial crus of greater alar cartilage.

Figure 2J:
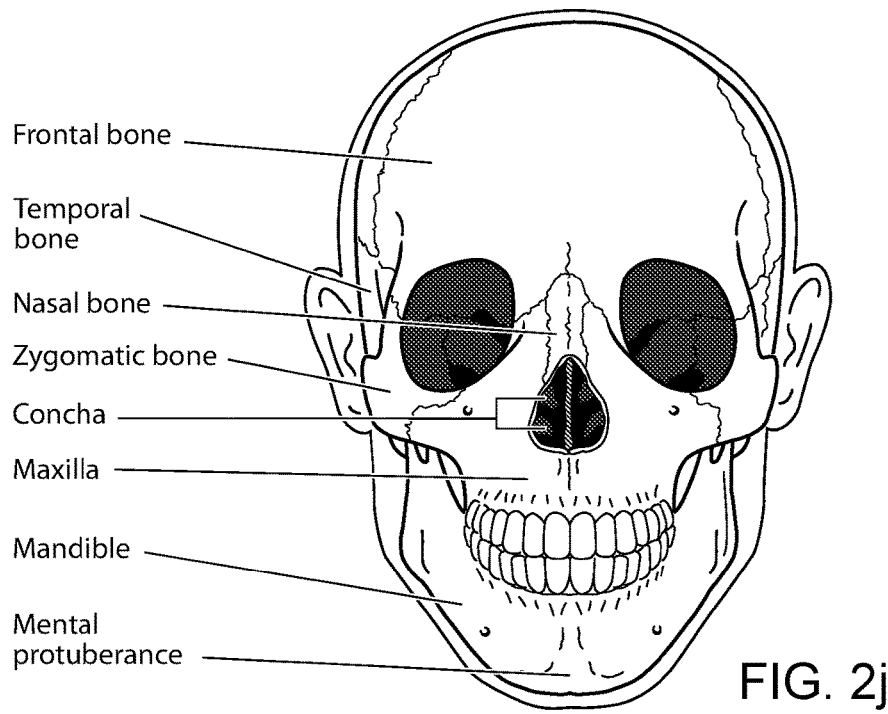

FIG. 2j shows a front view of the bones of a skull including the frontal, temporal, nasal and zygomatic bones. Nasal concha are indicated, as are the maxilla, mandible and mental protuberance.

Figure 2K:
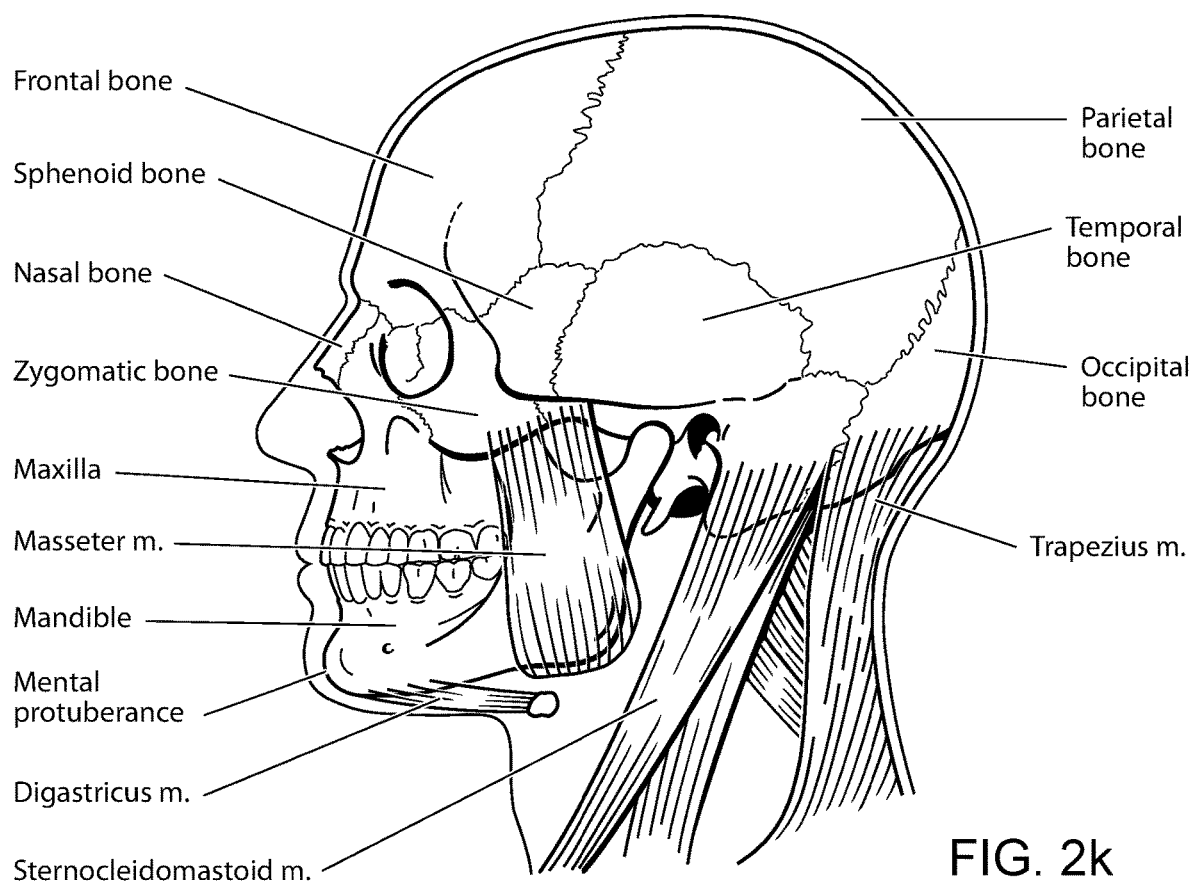
Figure 2I:
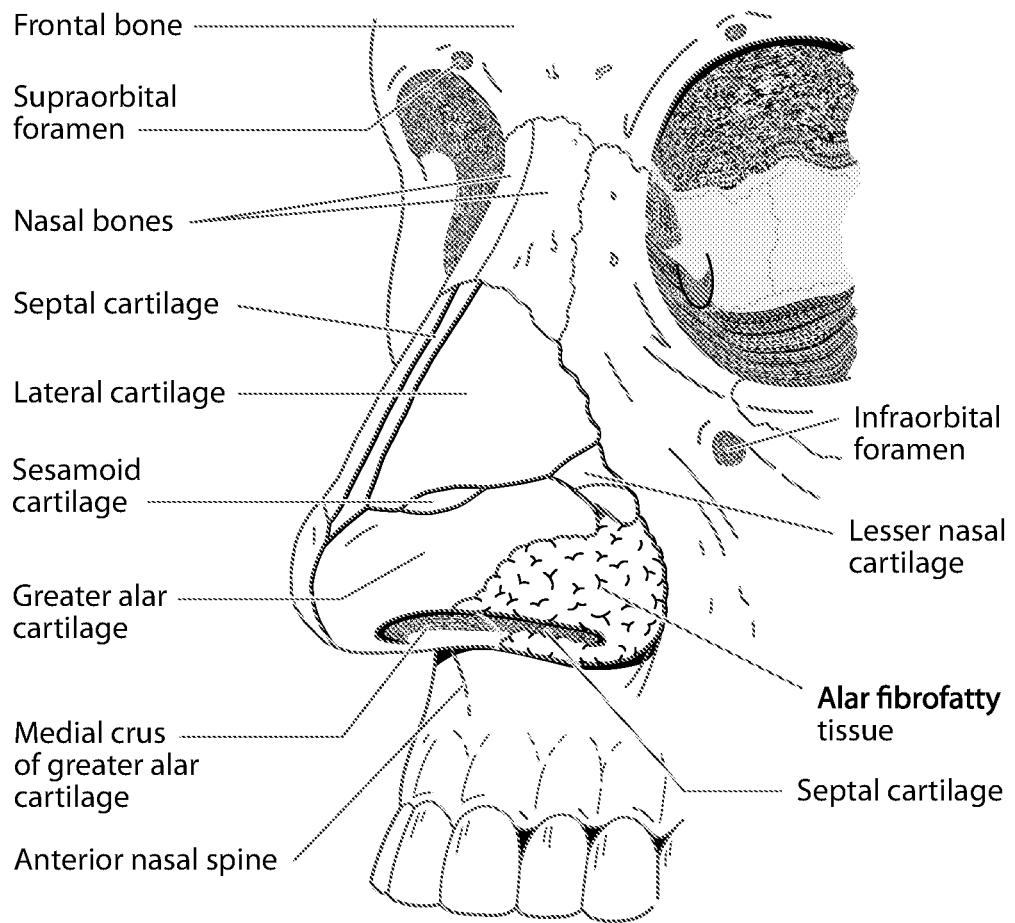

FIG. 2k shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter sternocleidomastoid and trapezius.

FIG. 2l shows an anterolateral view of a nose.

4.3 Pap Device and Humidifier

Figure 3A:
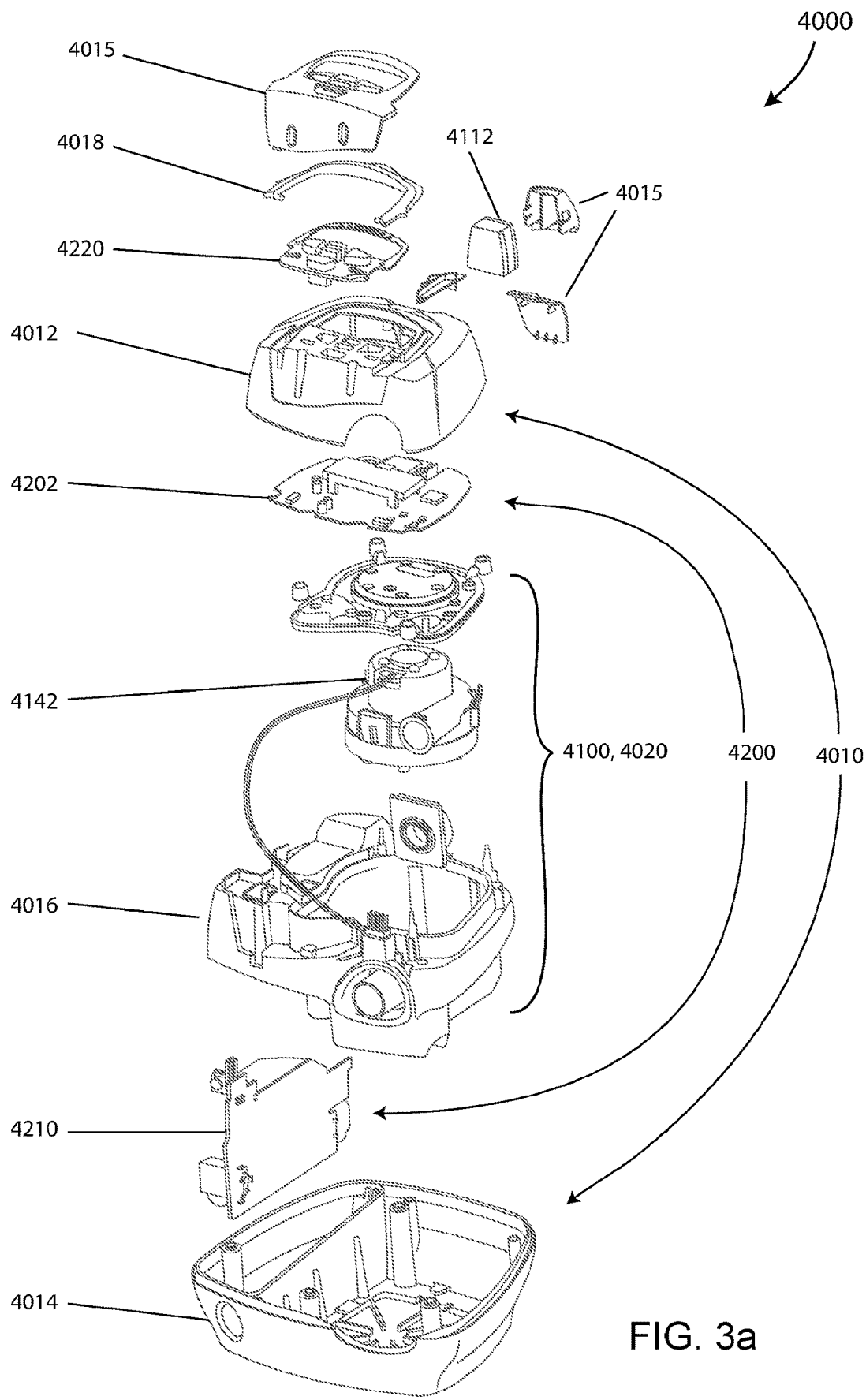

FIG. 3a shows an exploded view of a PAP device according to an example of the present technology.

Figure 3B:
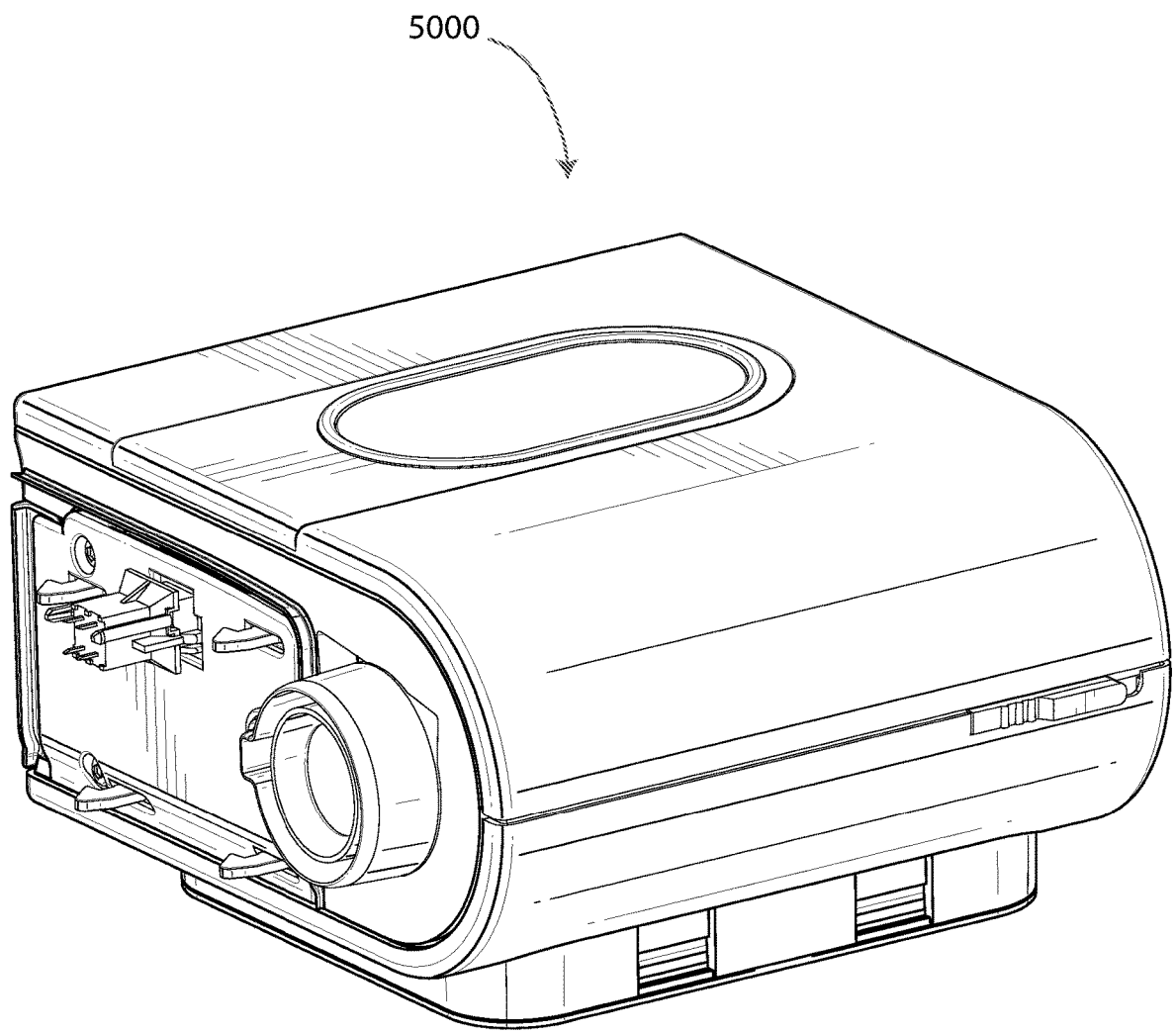

FIG. 3b shows a perspective view of a humidifier in accordance with one form of the present technology.

Figure 3C:
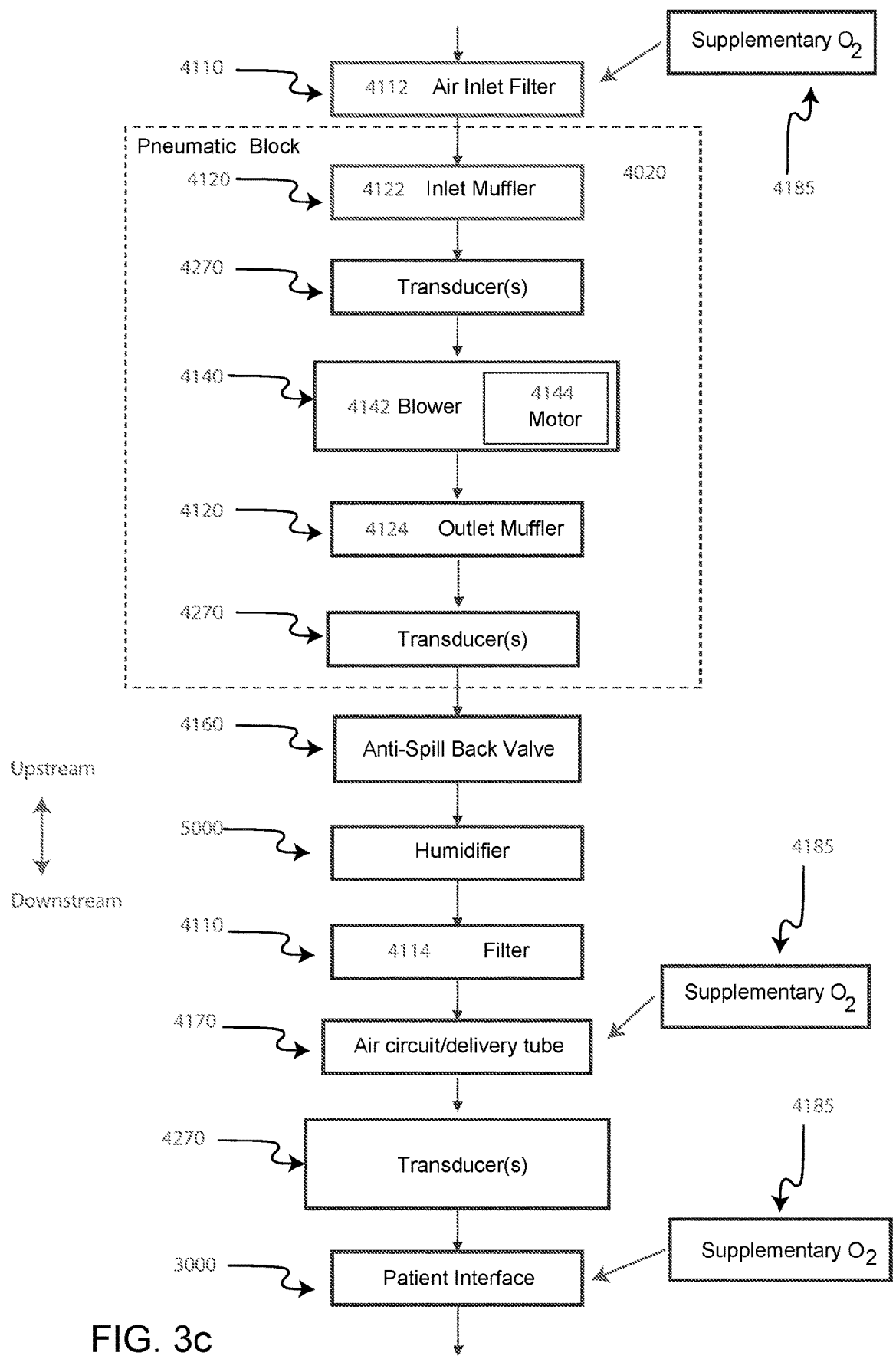

FIG. 3c shows a schematic diagram of the pneumatic circuit of a PAP device in accordance with one form of the present technology. The directions of upstream and downstream are indicated.

4.4 Patient Interface

Figure 4A:
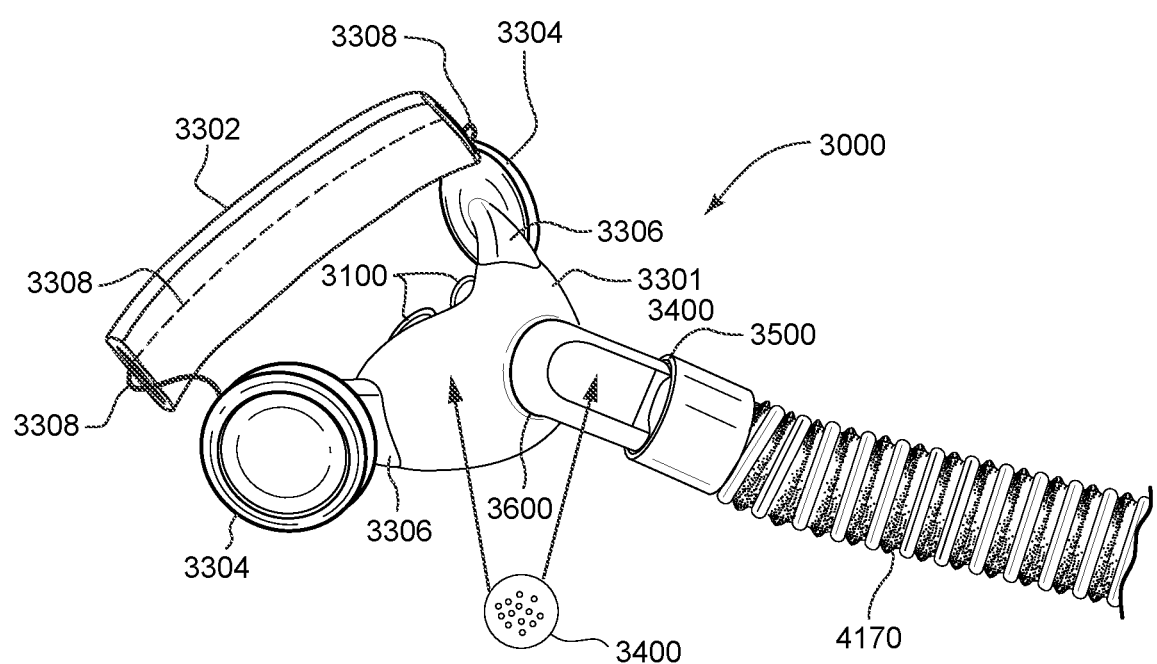

FIG. 4a shows a perspective view of a patient interface according to an example of the present technology.

Figure 4B:
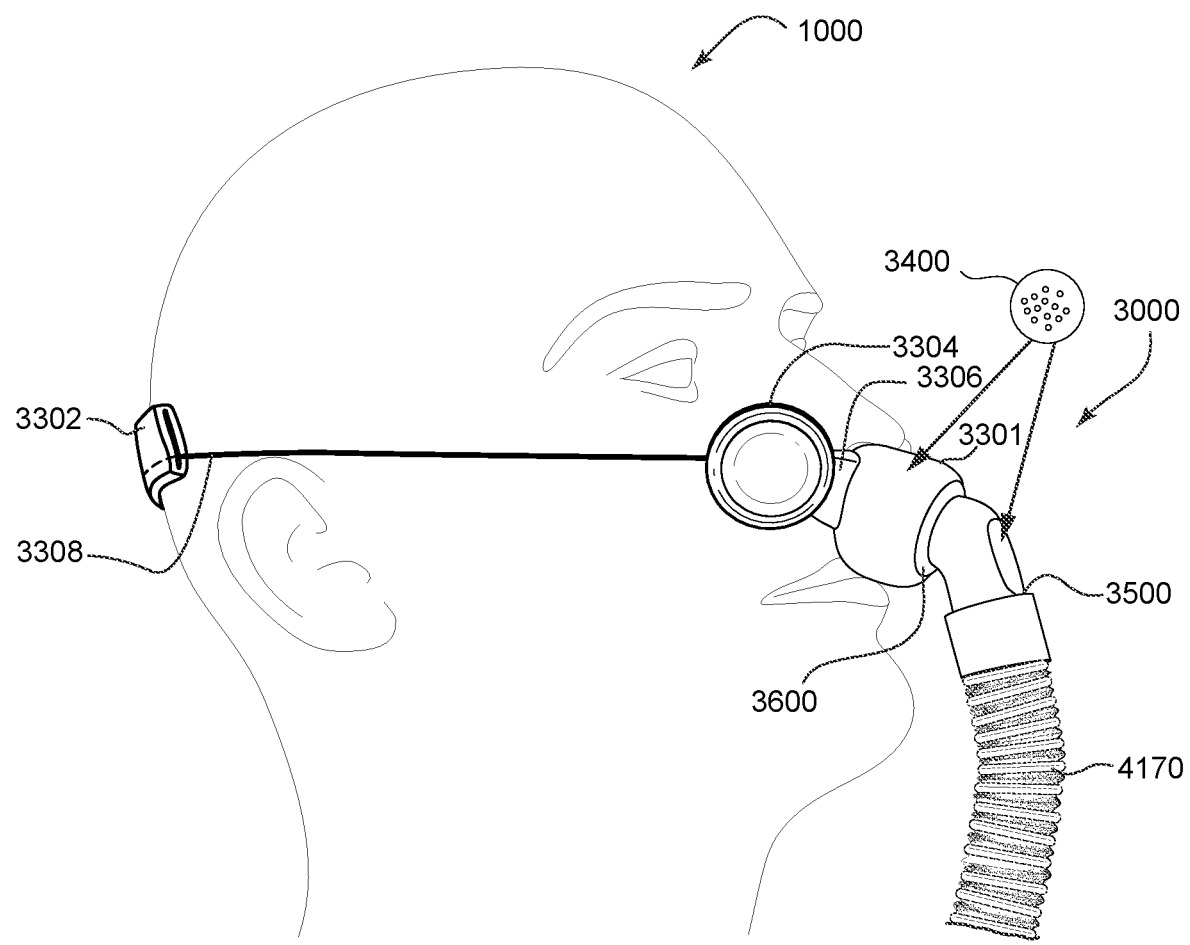

FIG. 4b shows a side view of a patient wearing a patient interface according to an example of the present technology.

Figure 4C:
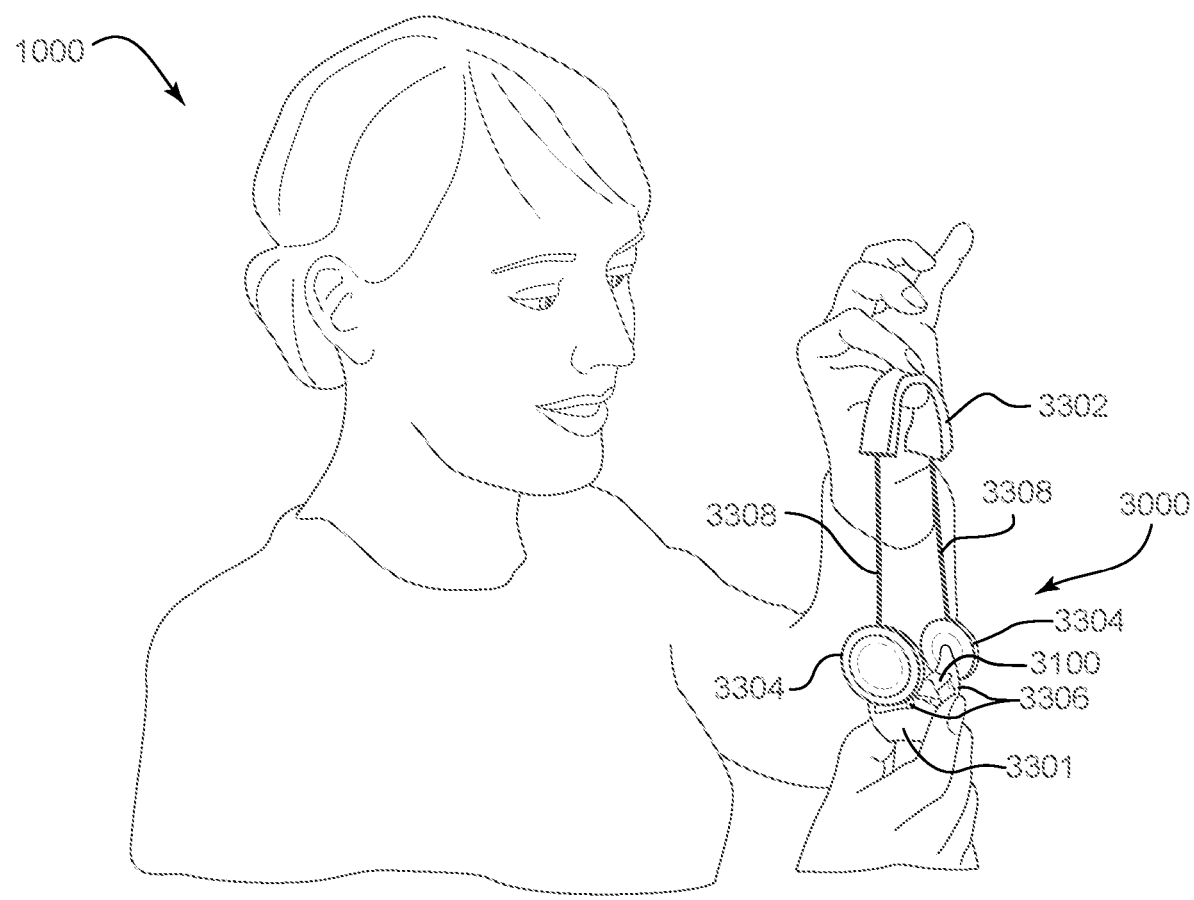

FIG. 4c shows a patient donning a patient interface according to an example of the present technology.

Figure 4D:
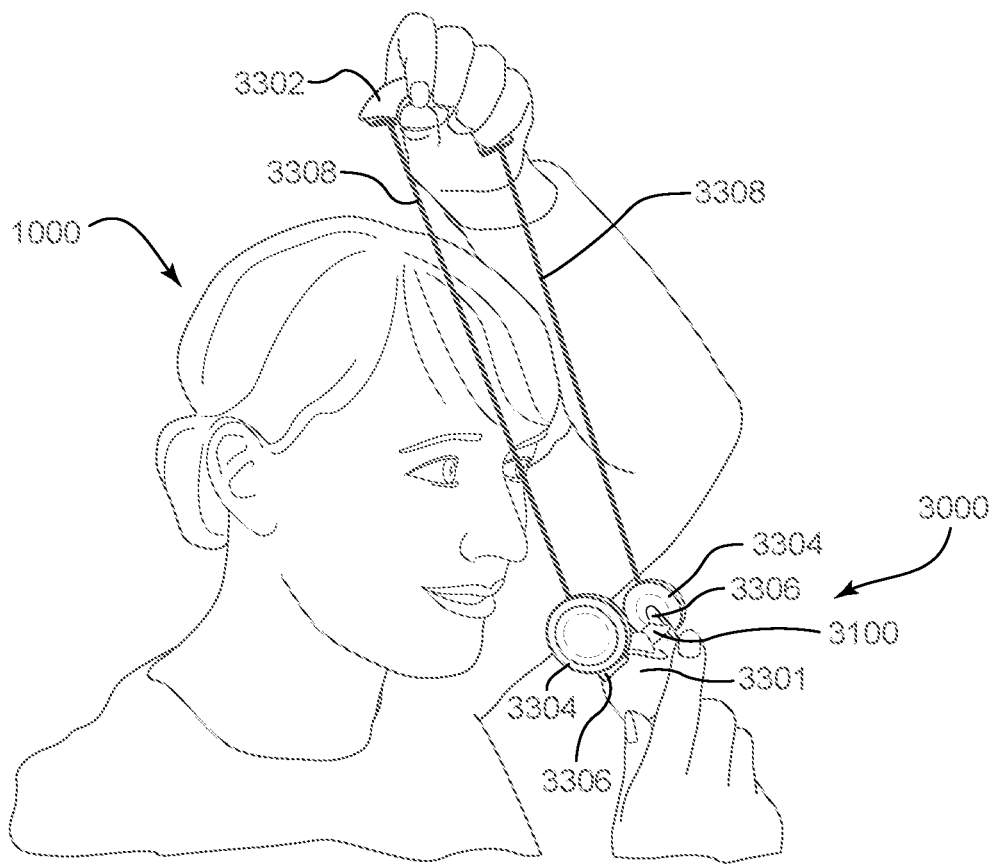

FIG. 4d shows a patient donning a patient interface according to an example of the present technology.

Figure 4E:
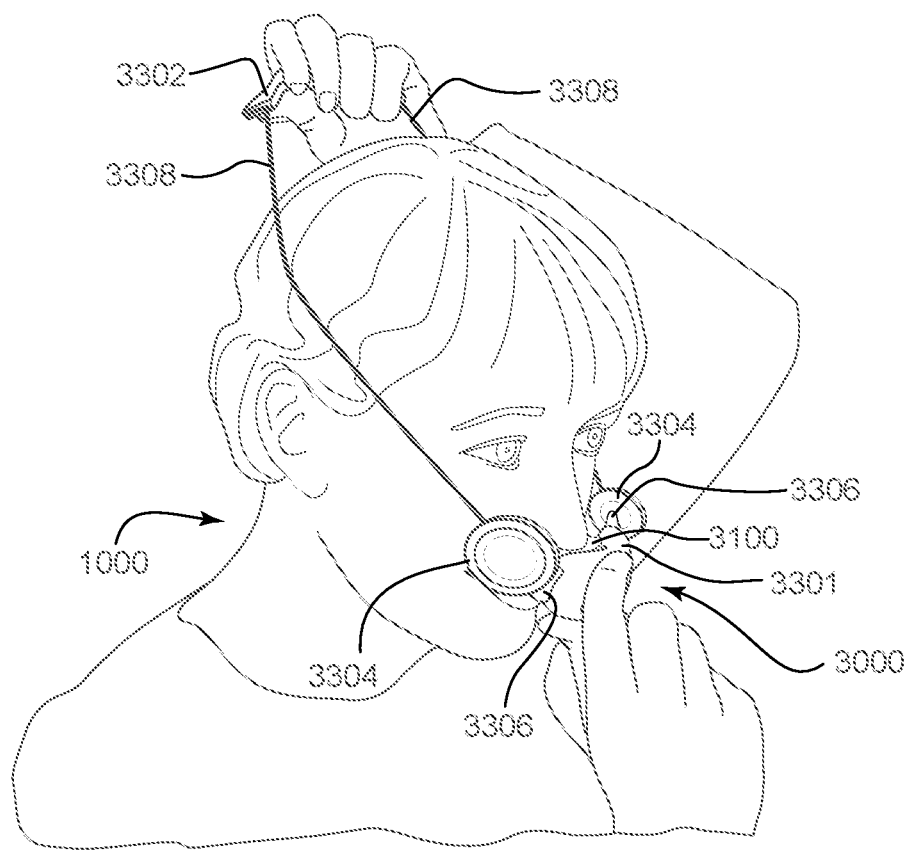

FIG. 4e shows a patient donning a patient interface according to an example of the present technology.

Figure 4F:
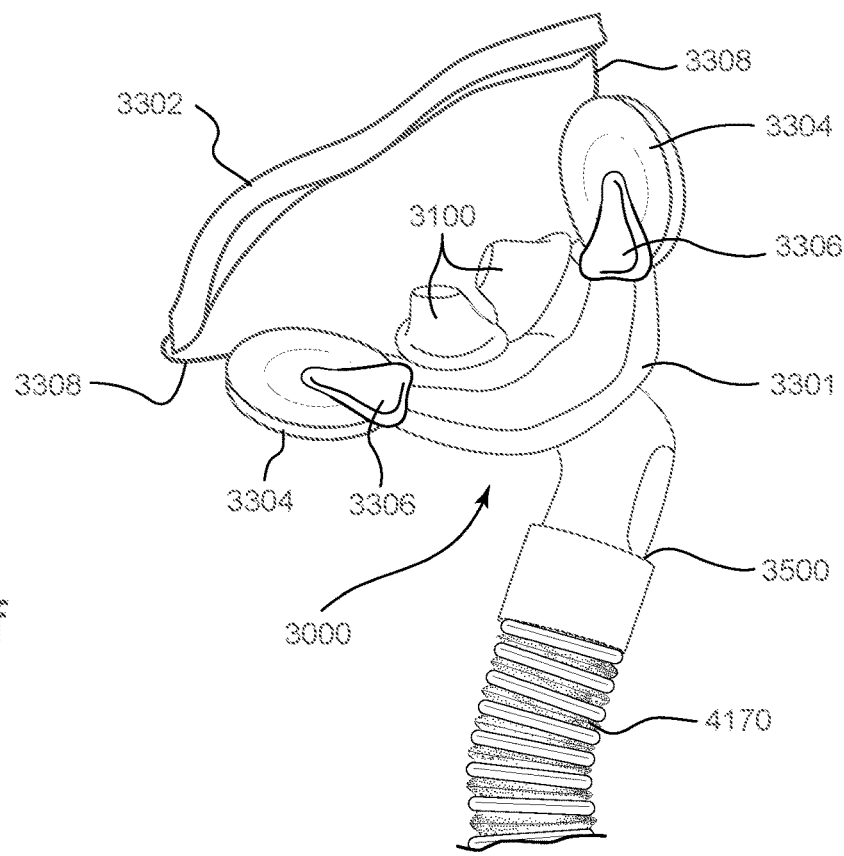

FIG. 4f shows a top view of a patient interface according to an example of the present technology.

Figure 4G:
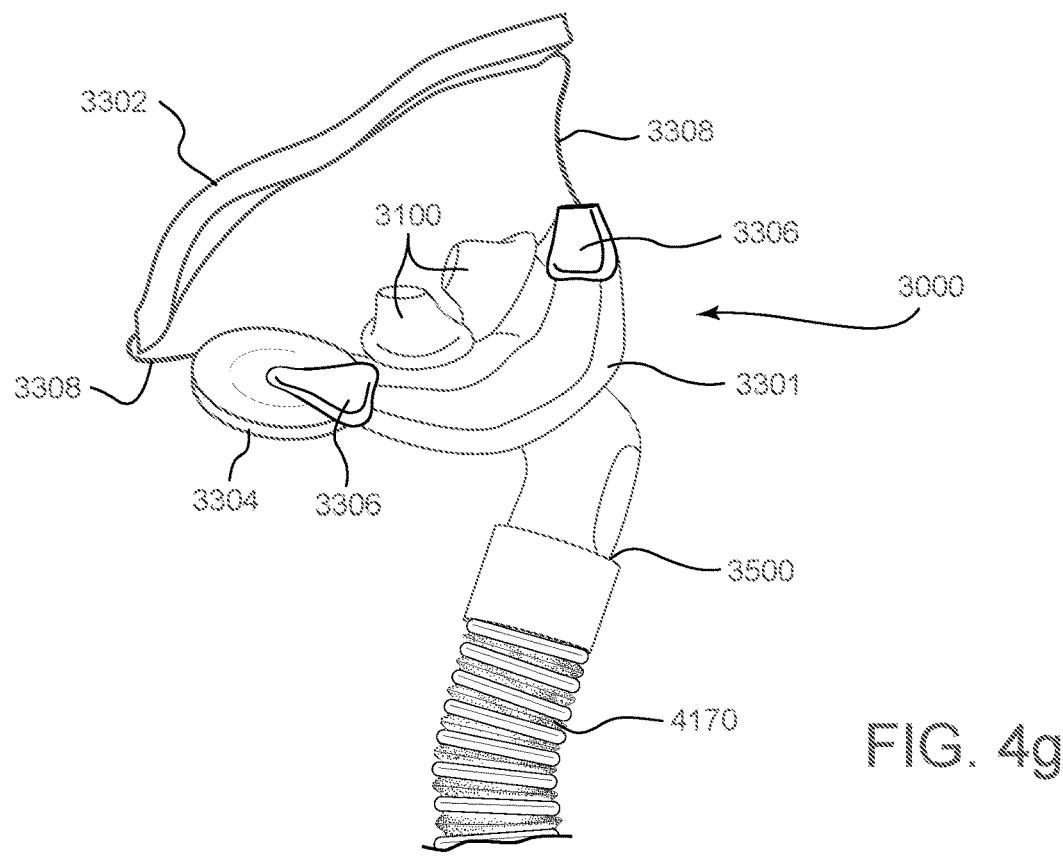

FIG. 4g shows a top view of a patient interface according to an example of the present technology.

Figure 5A:
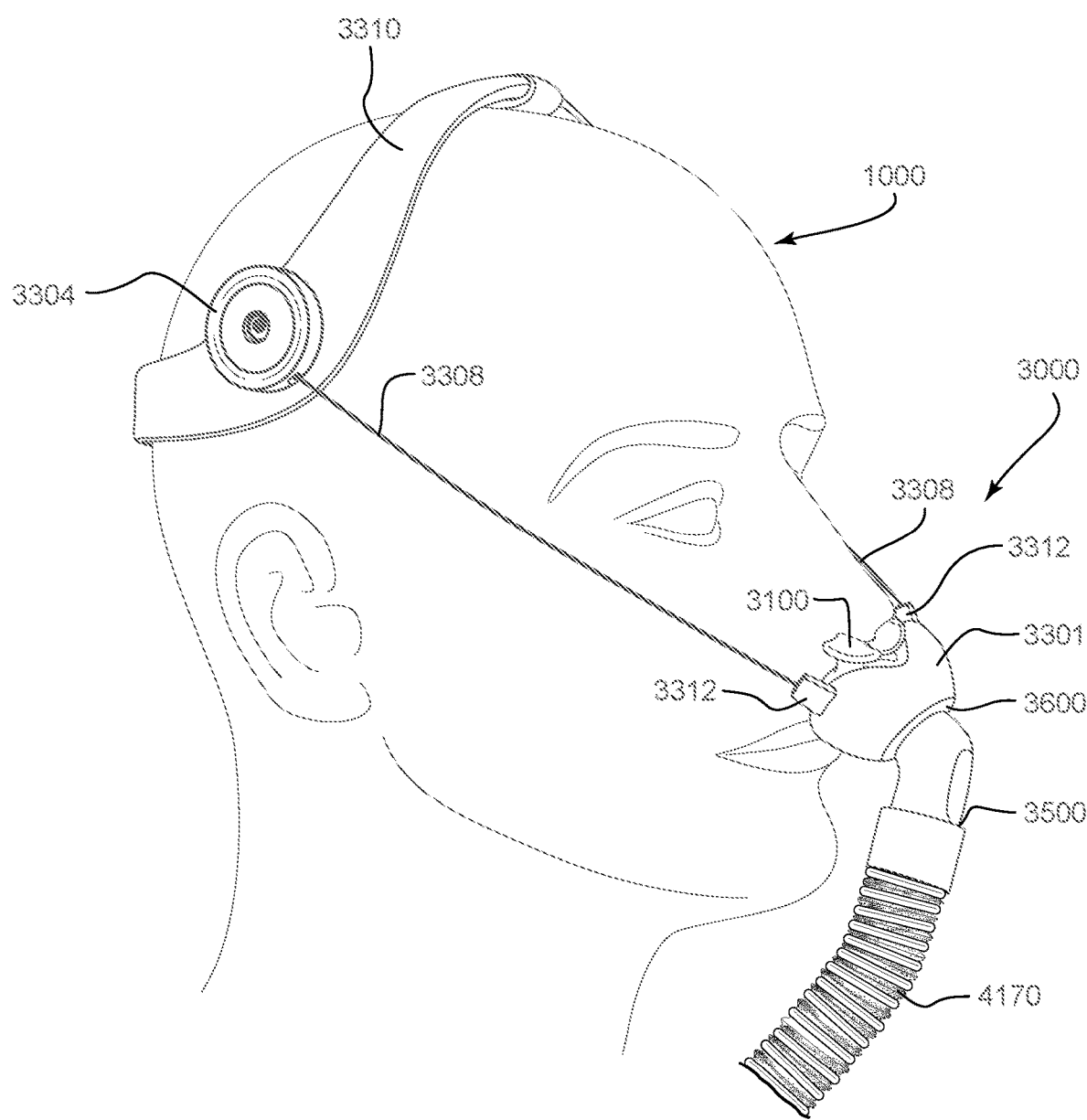

FIG. 5a shows a side view of a patient wearing a patient interface according to an example of the present technology.

Figure 5B:
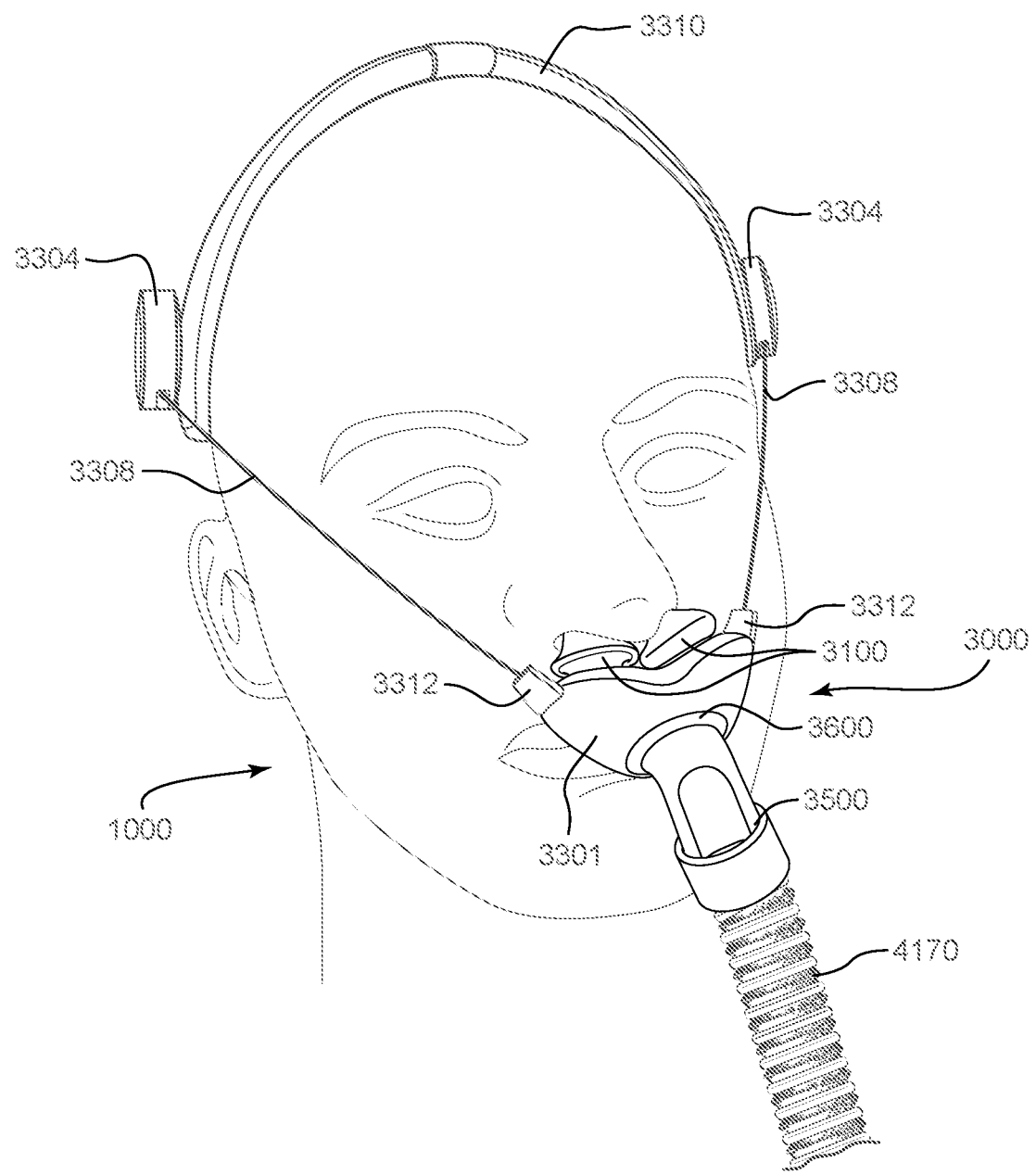

FIG. 5b shows a front perspective view of a patient wearing a patient interface according to an example of the present technology.

Figure 5C:
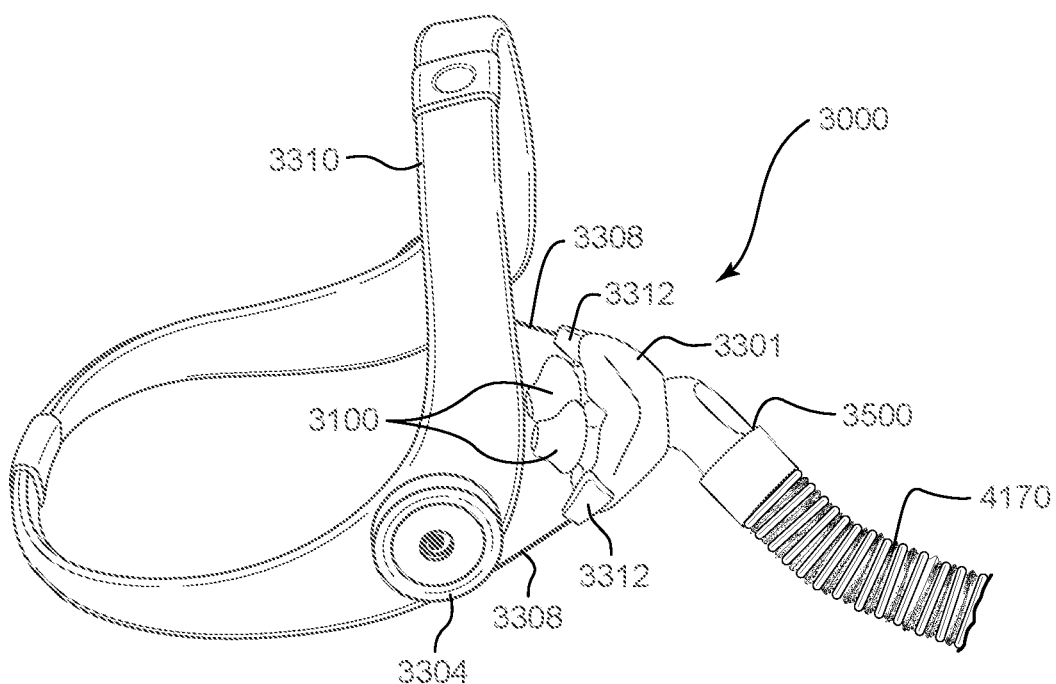

FIG. 5c shows a side view of a patient interface according to an example of the present technology.

Figure 5D:
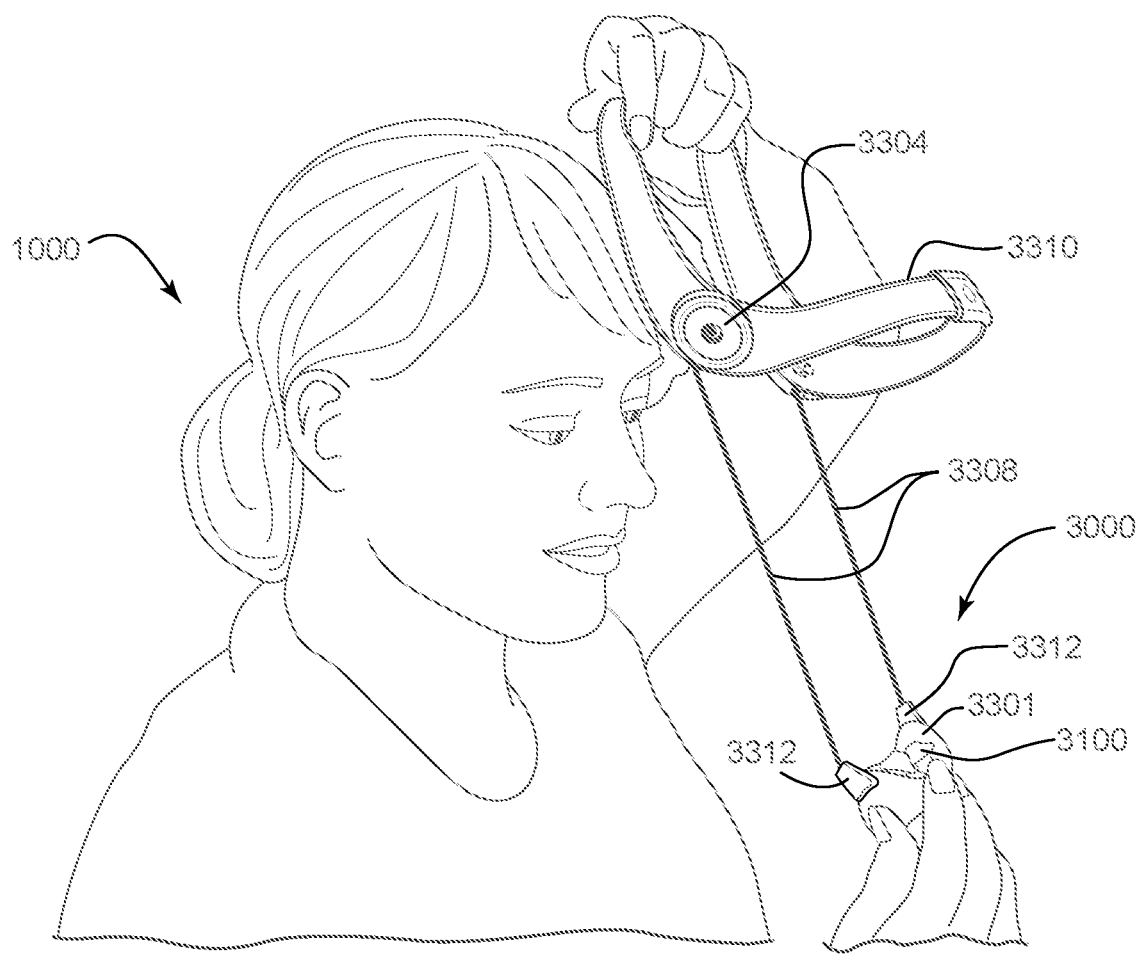

FIG. 5d shows a patient donning a patient interface according to an example of the present technology.

Figure 5E:
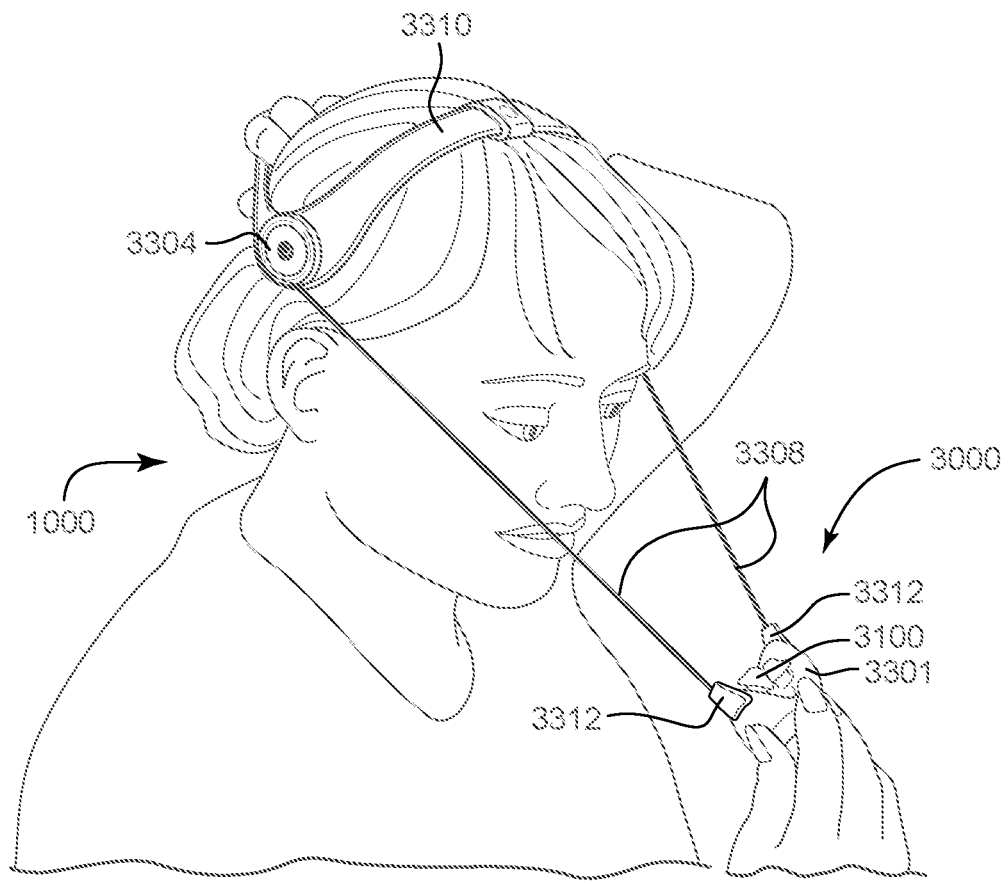

FIG. 5e shows a patient donning a patient interface according to an example of the present technology.

Figure 5F:
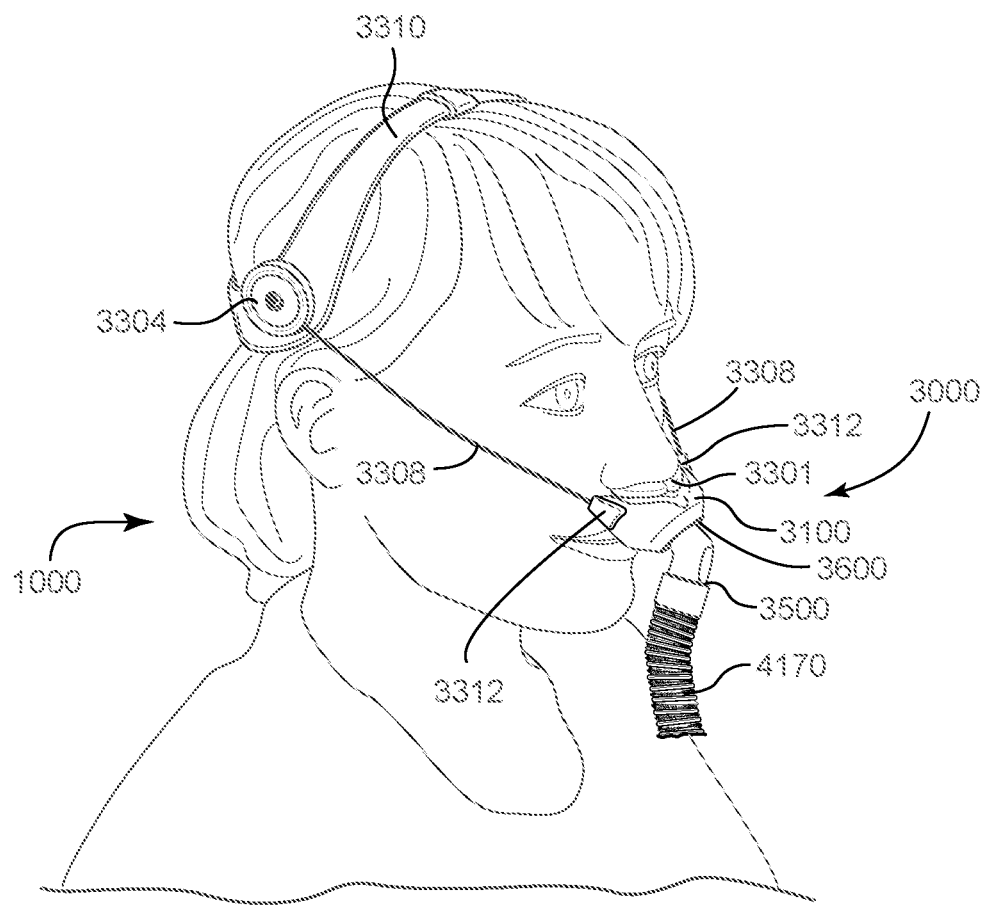

FIG. 5f shows a perspective view of a patient wearing a patient interface according to an example of the present technology.

Figure 5G:
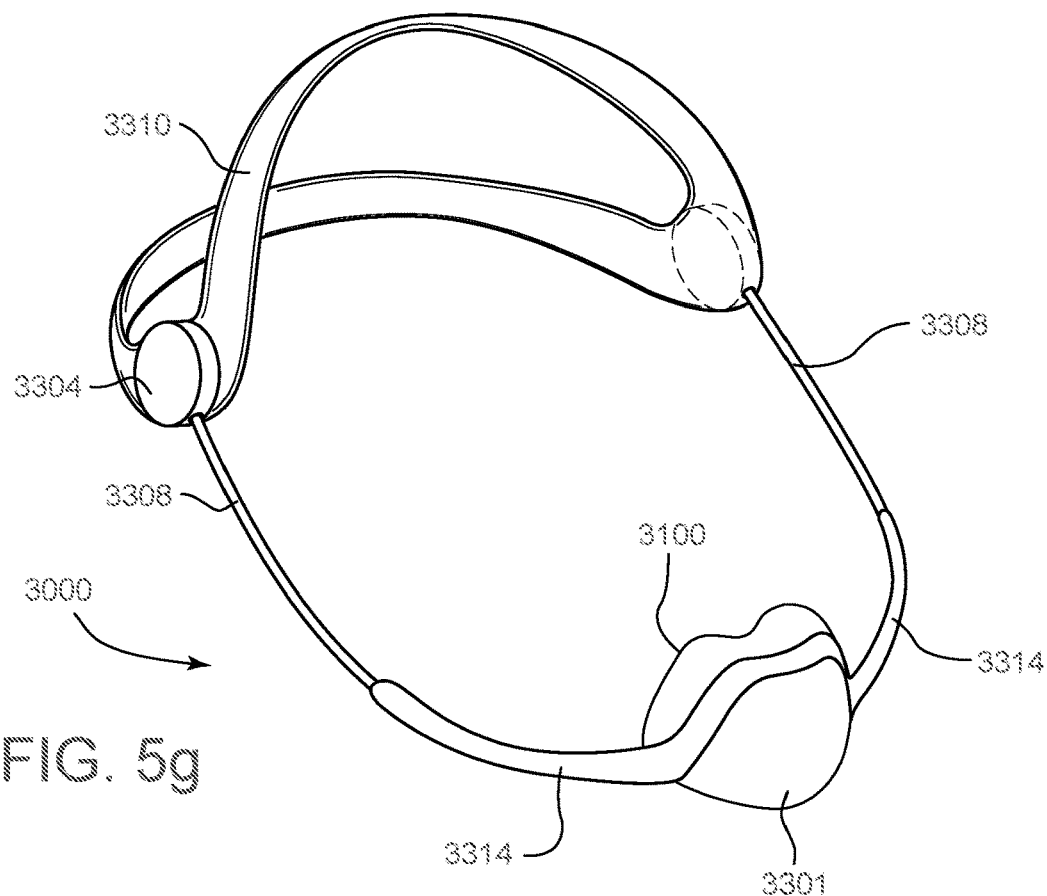

FIG. 5g shows a perspective view of a patient interface according to an example of the present technology.

Figure 5H:
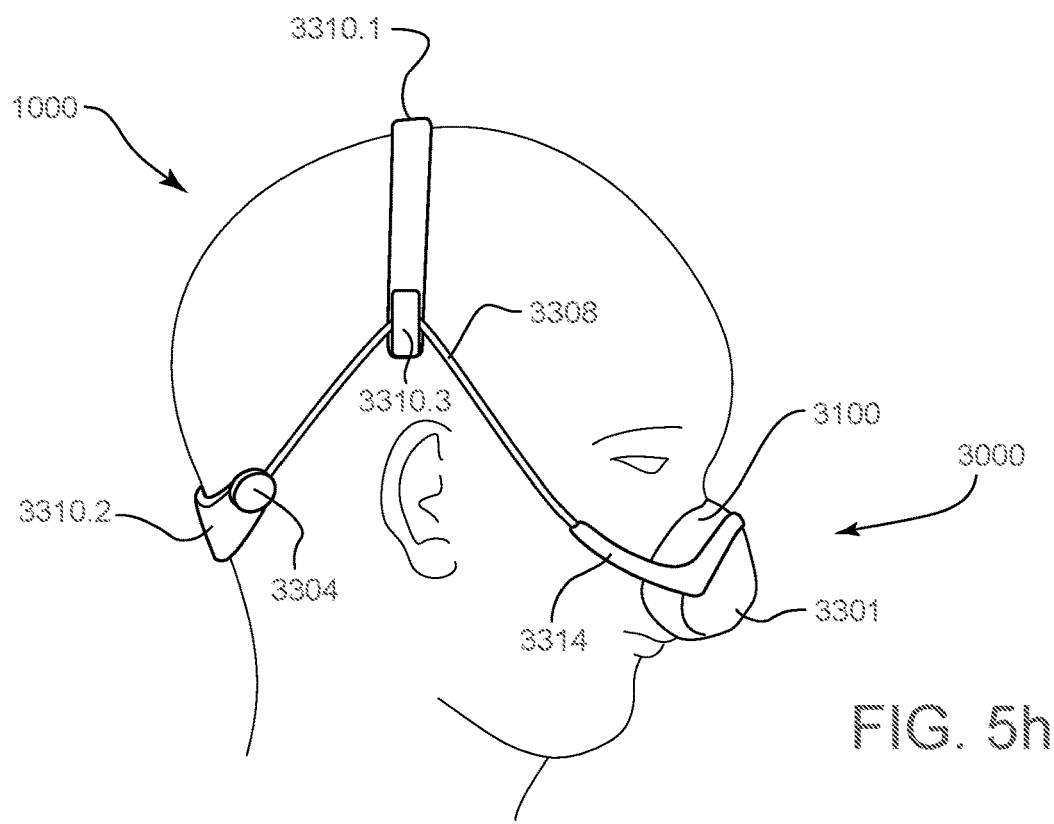

FIG. 5h shows a side view of a patient wearing a patient interface according to an example of the present technology.

Figure 6A:
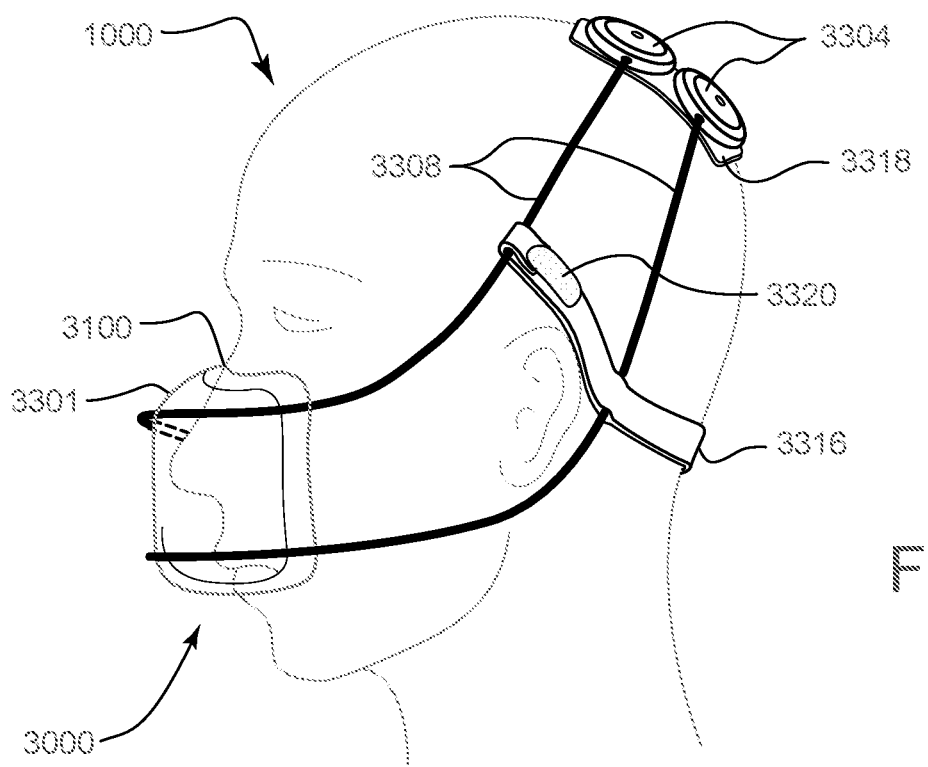

FIG. 6a shows a side view of a patient wearing a patient interface according to an example of the present technology.

Figure 6B:
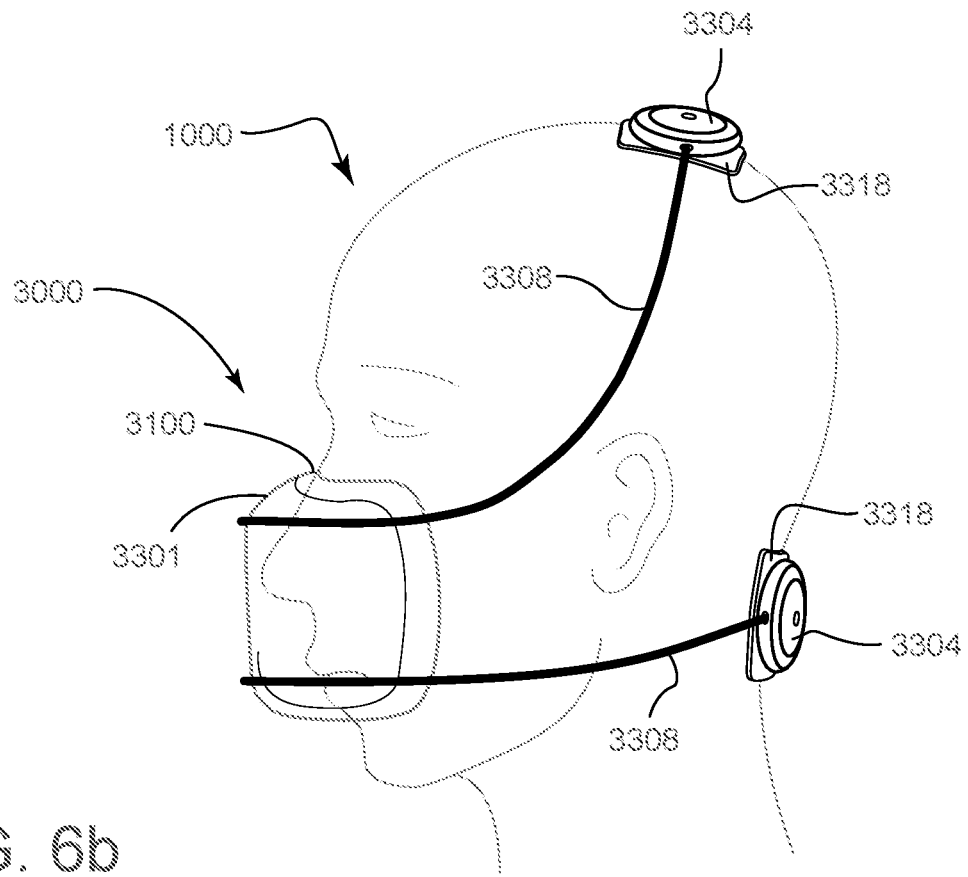

FIG. 6b shows a side view of a patient wearing a patient interface according to an example of the present technology.

Figure 6C:
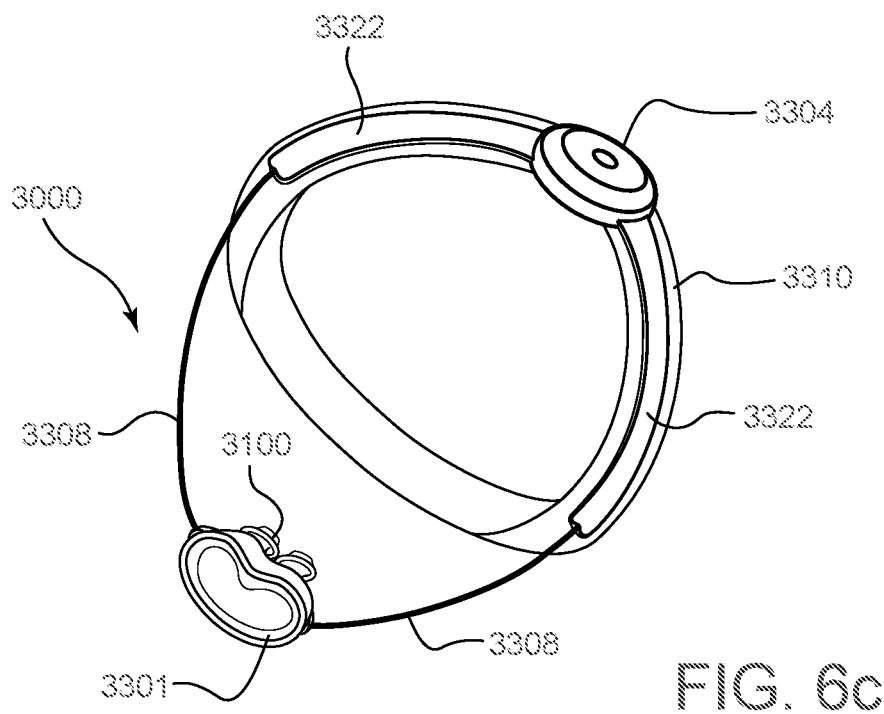

FIG. 6c shows a top view of a patient interface according to an example of the present technology.

Figure 6D:
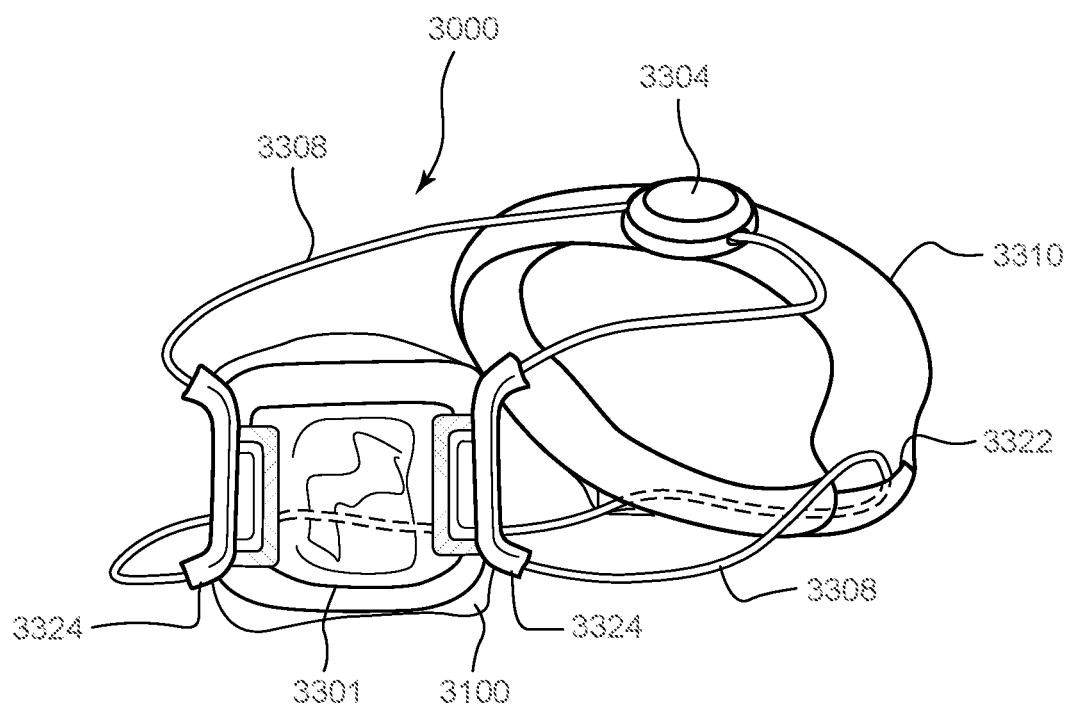

FIG. 6d shows a front perspective view of a patient interface according to an example of the present technology.

Figure 6E:
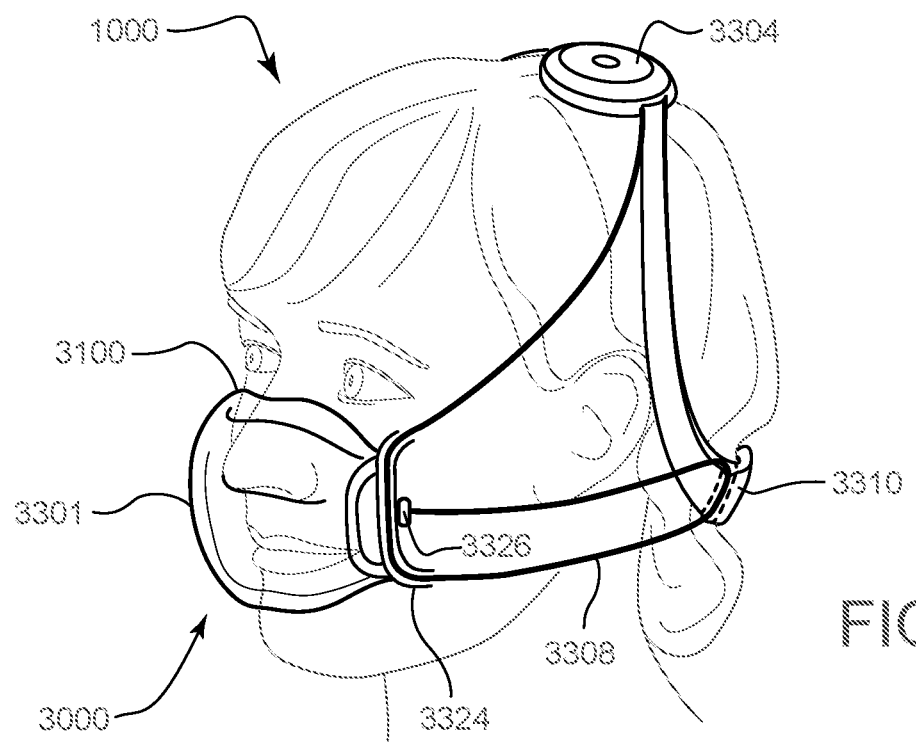

FIG. 6e shows a perspective view of a patient wearing a patient interface according to an example of the present technology.

Figure 6F:
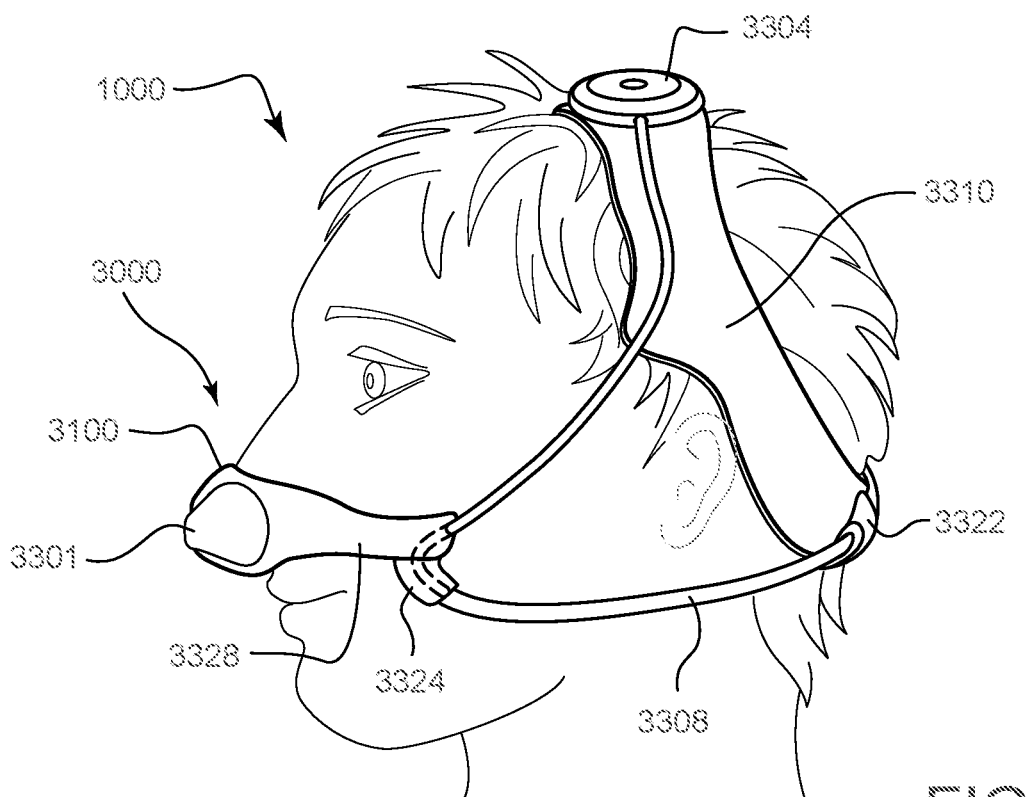

FIG. 6f shows a side view of a patient wearing a patient interface according to an example of the present technology.

Figure 7A:
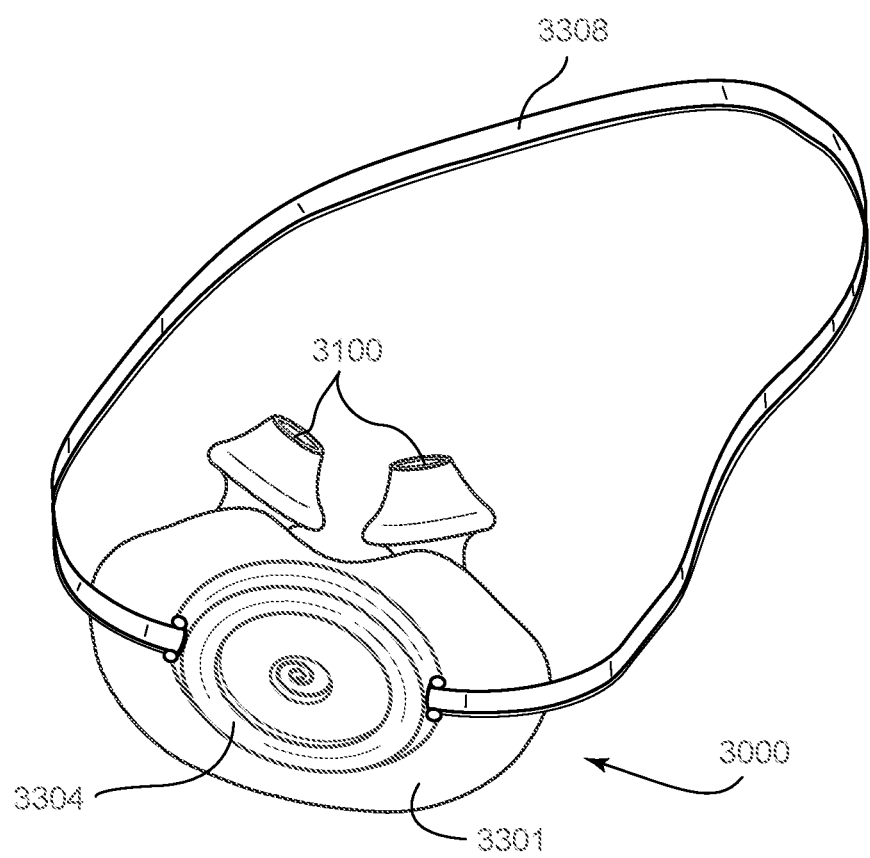

FIG. 7a shows a front view of a patient interface according to an example of the present technology.

Figure 7B:
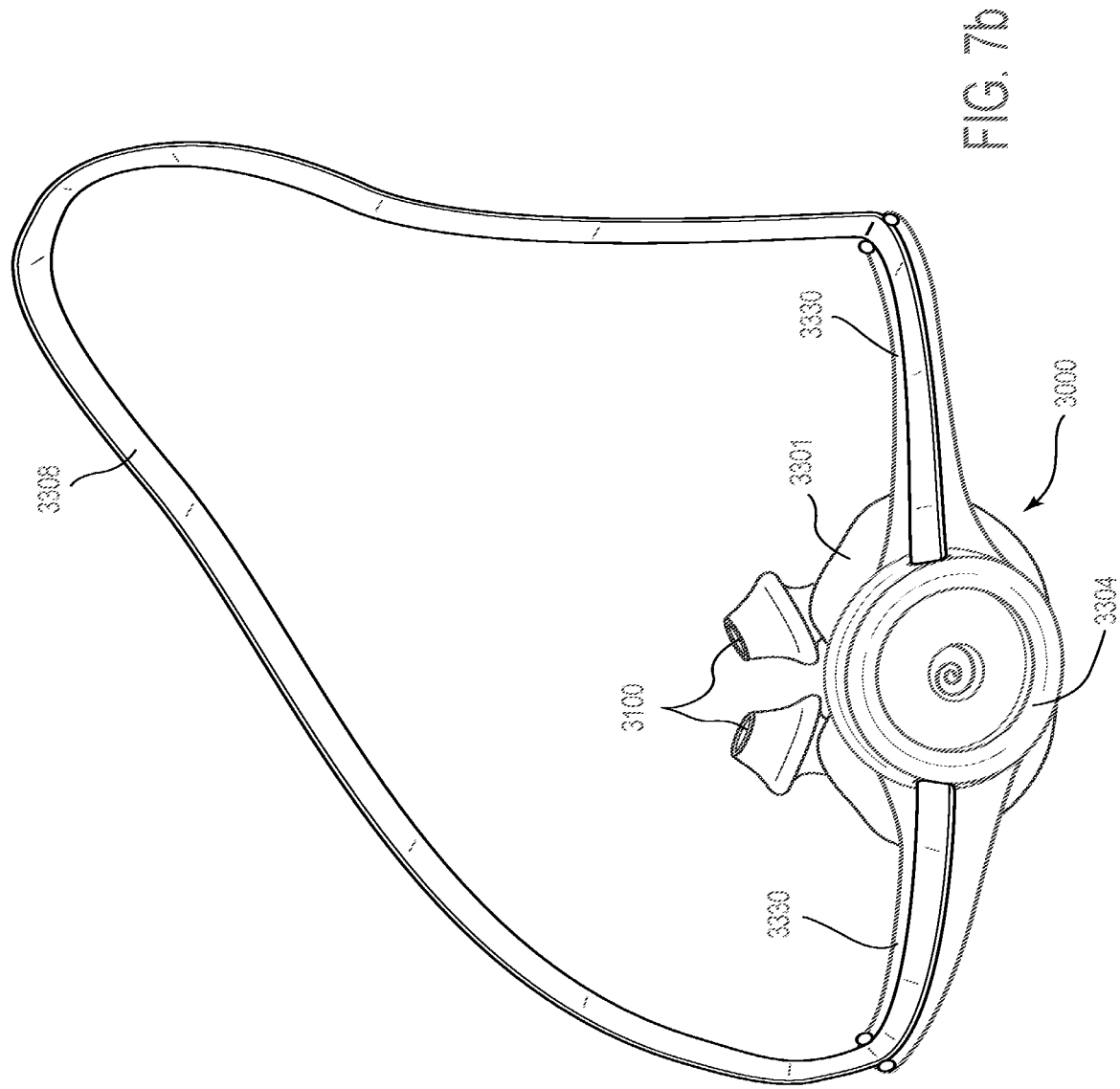

FIG. 7b shows a front view of a patient interface according to an example of the present technology.

Figure 8A:
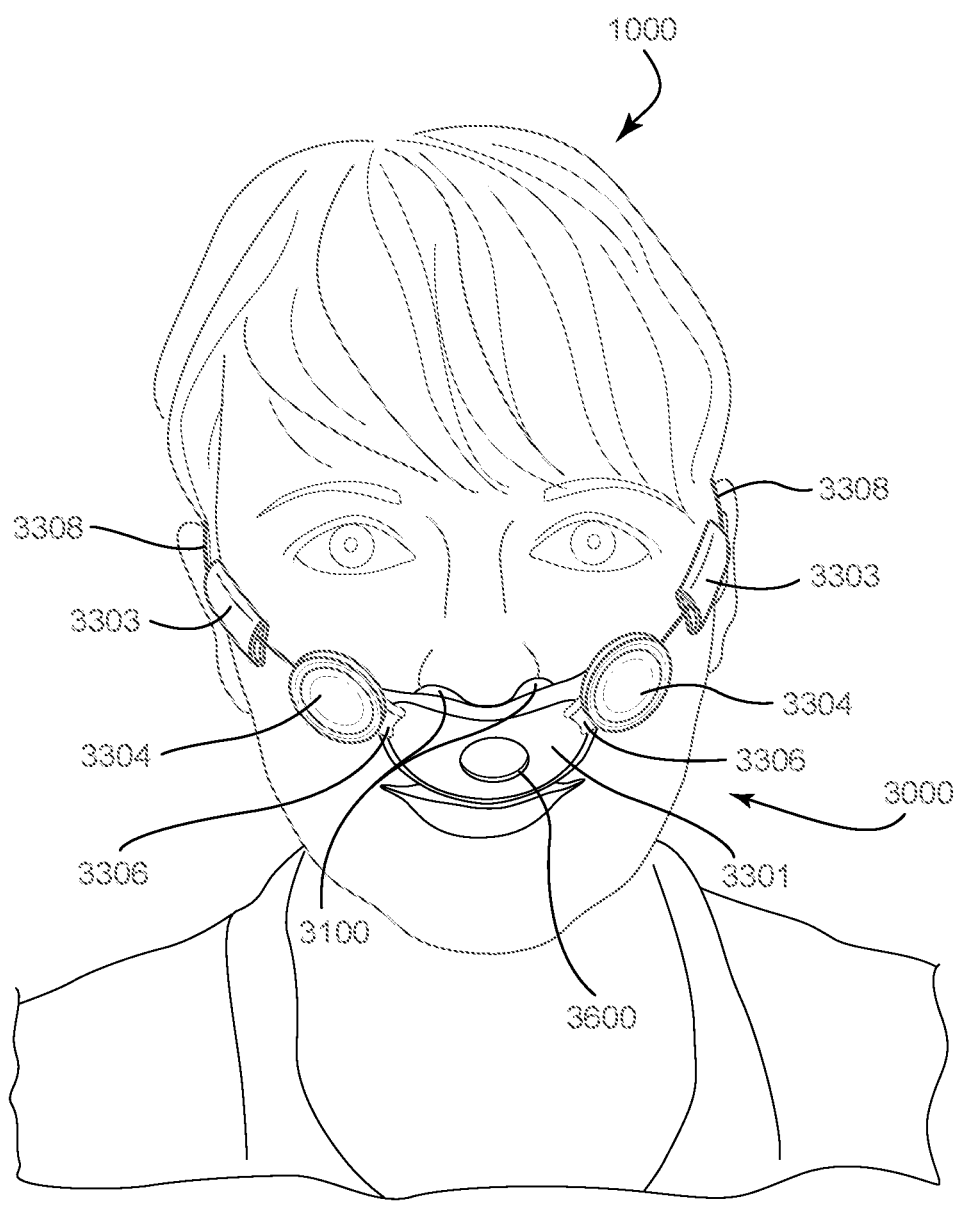

FIG. 8a shows a front view of a patient wearing a patient interface according to an example of the present technology.

Figure 8B:
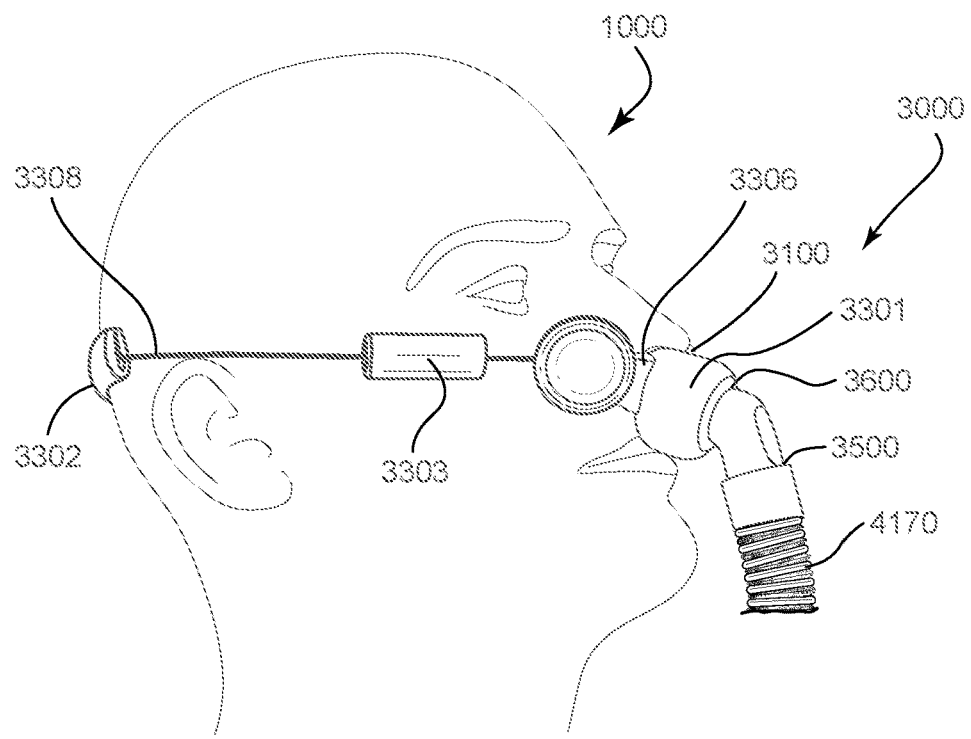

FIG. 8b shows a side view of a patient wearing a patient interface according to an example of the present technology.

Figure 8C:
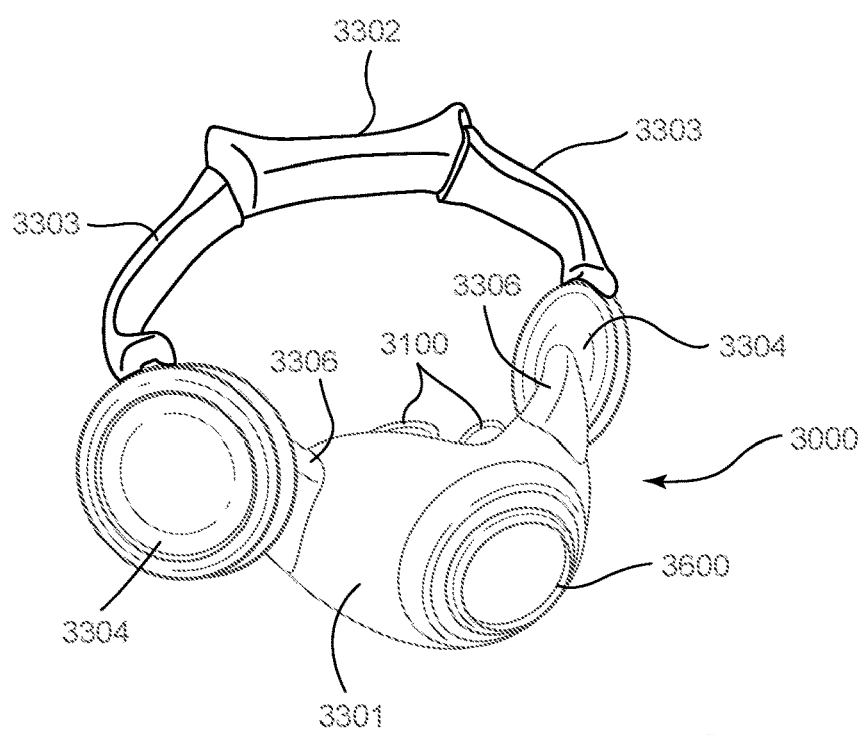

FIG. 8c shows a perspective view of a patient interface according to an example of the present technology.

Figure 9A:
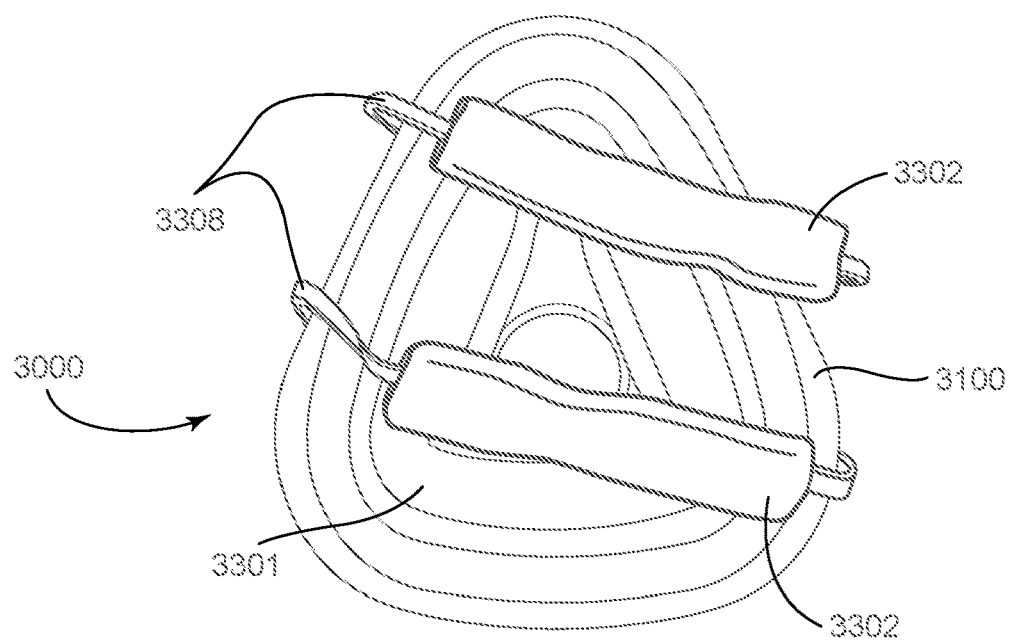

FIG. 9a shows a rear view of a patient interface according to an example of the present technology.

Figure 9B:
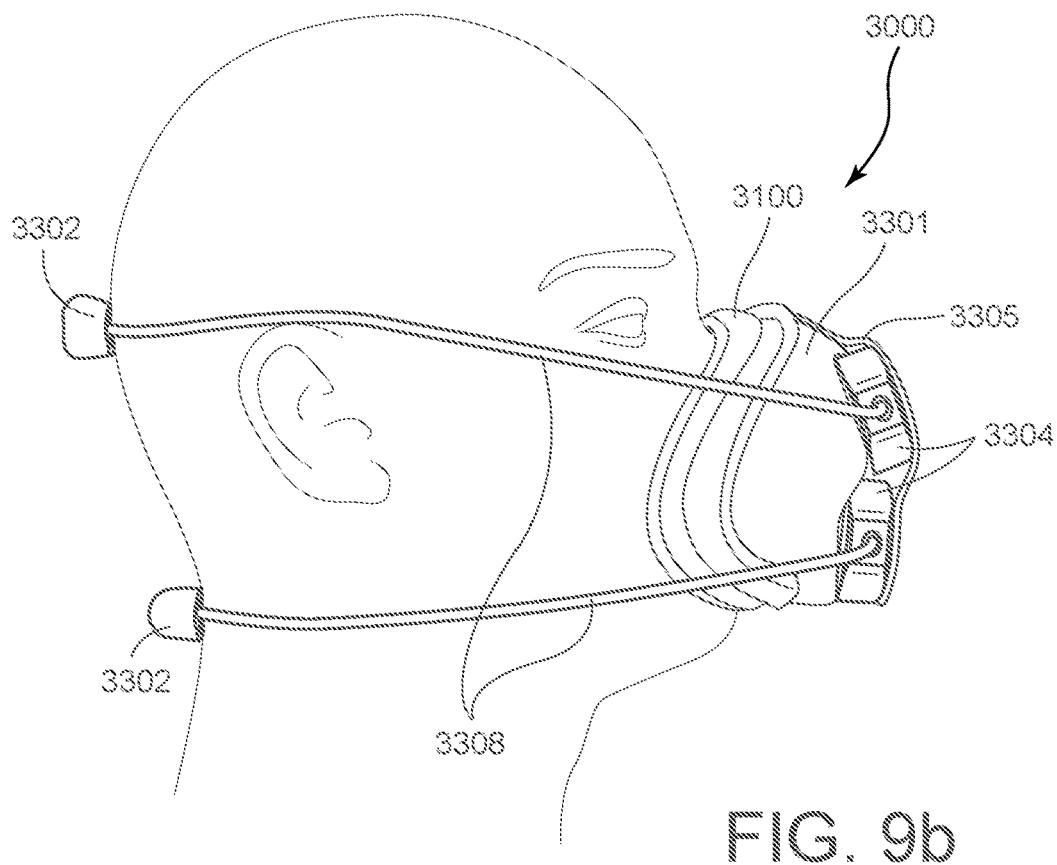

FIG. 9b shows a side view of a patient wearing a patient interface according to an example of the present technology.

Figure 9C:
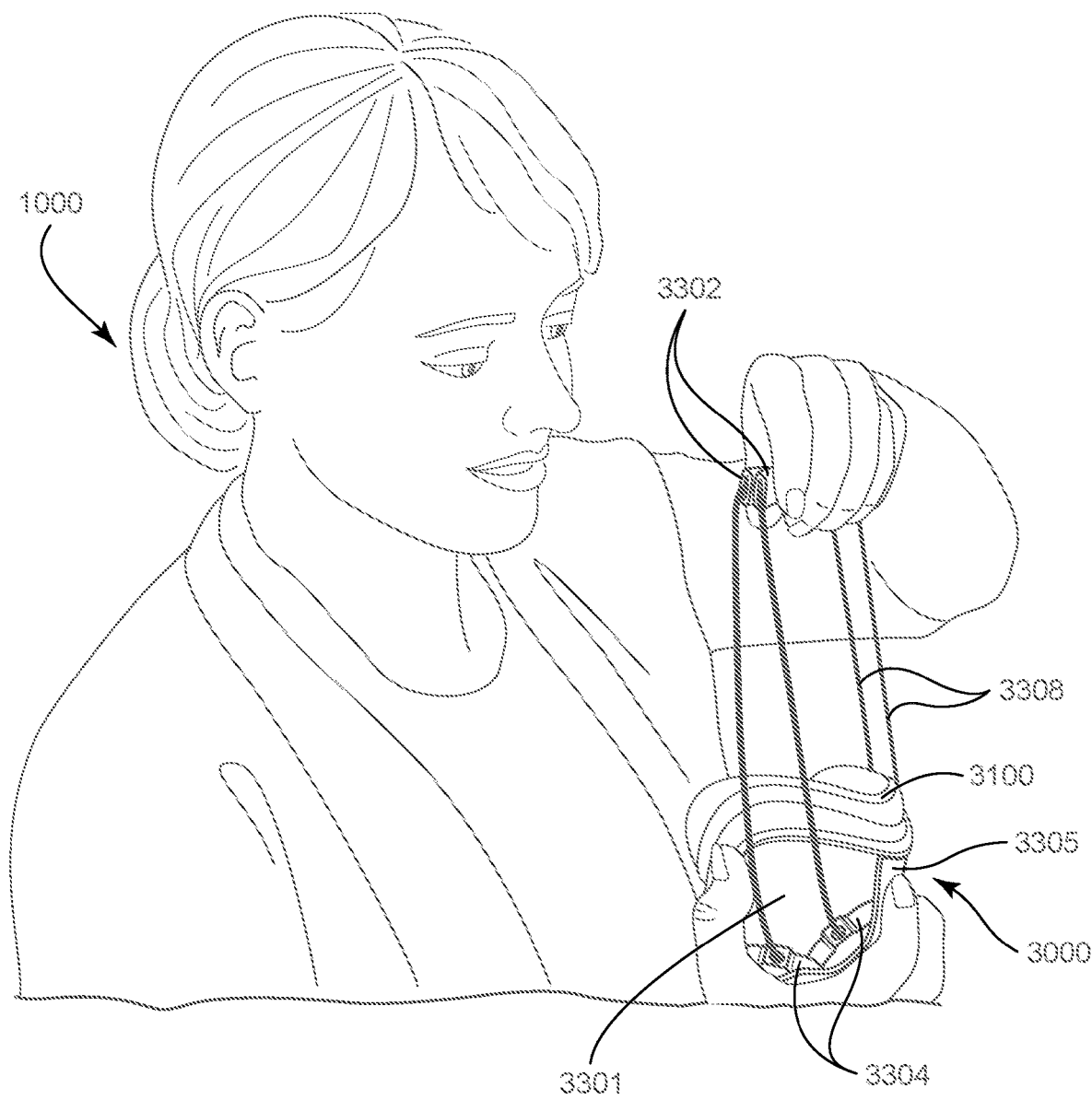

FIG. 9c shows a patient donning a patient interface according to an example of the present technology.

Figure 9D:
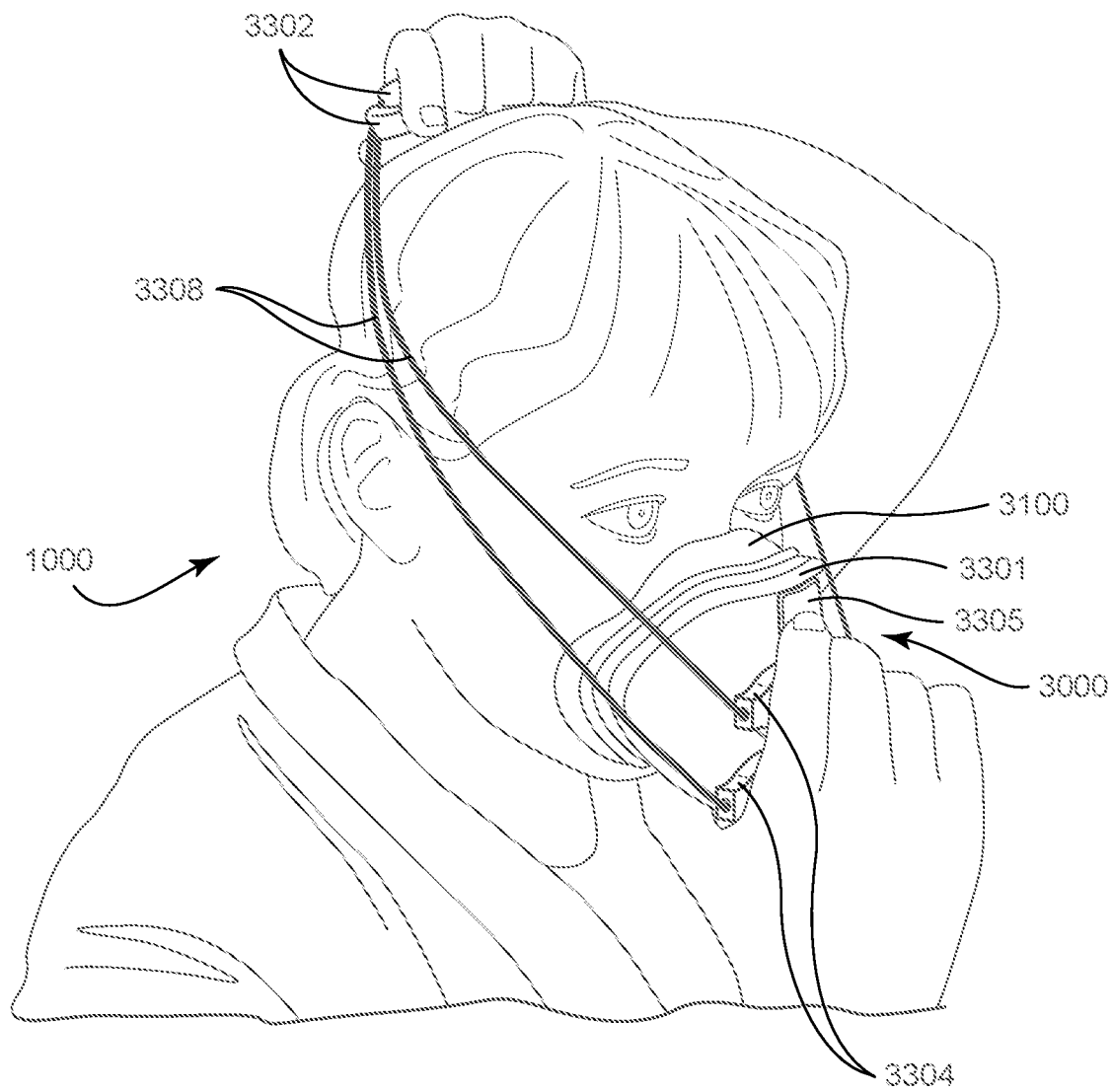

FIG. 9d shows a patient donning a patient interface according to an example of the present technology.

Figure 9E:
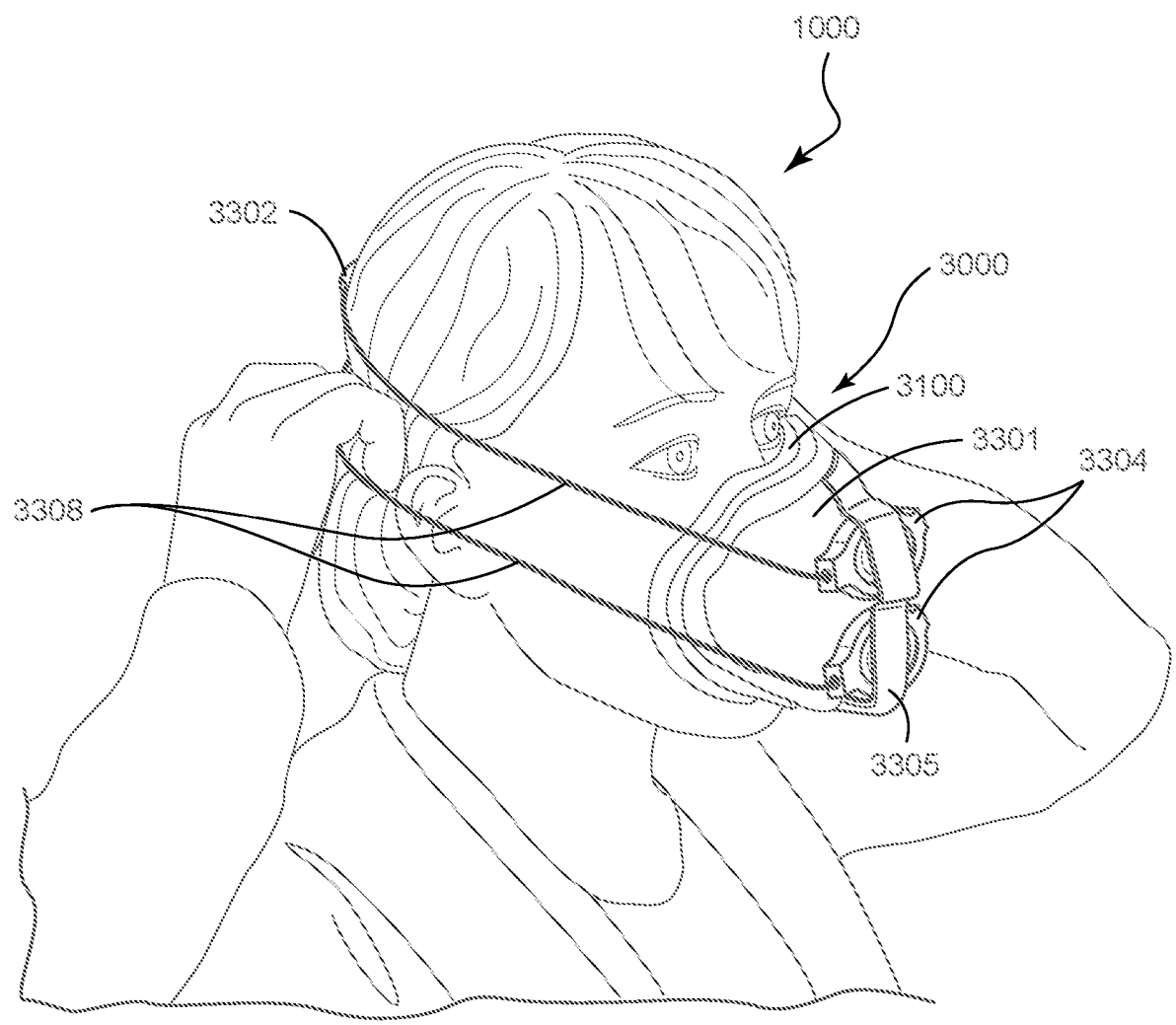

FIG. 9e shows a patient donning a patient interface according to an example of the present technology.

Figure 9F:
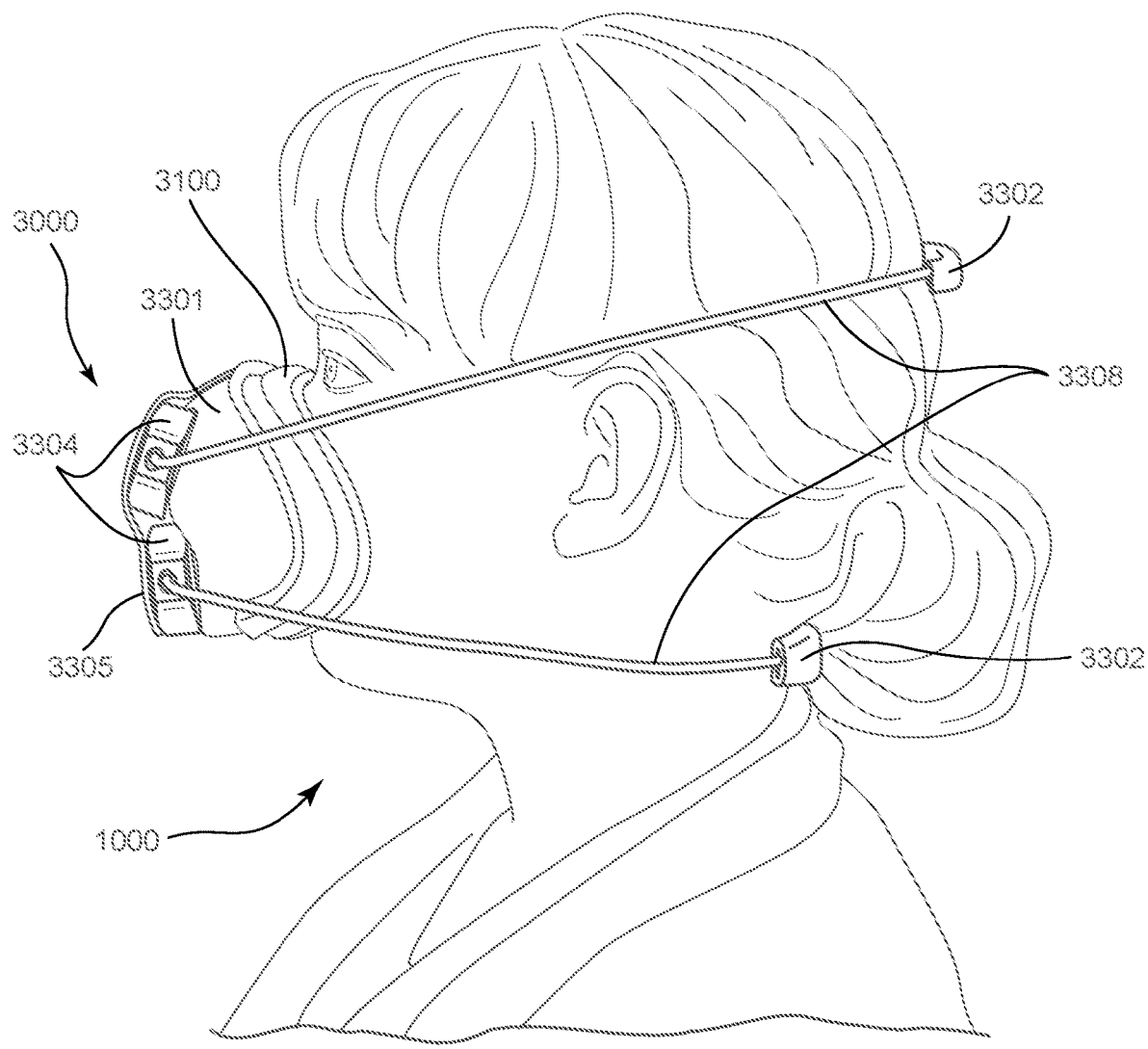

FIG. 9f shows a side view of a patient wearing a patient interface according to an example of the present technology.

Figure 10A:
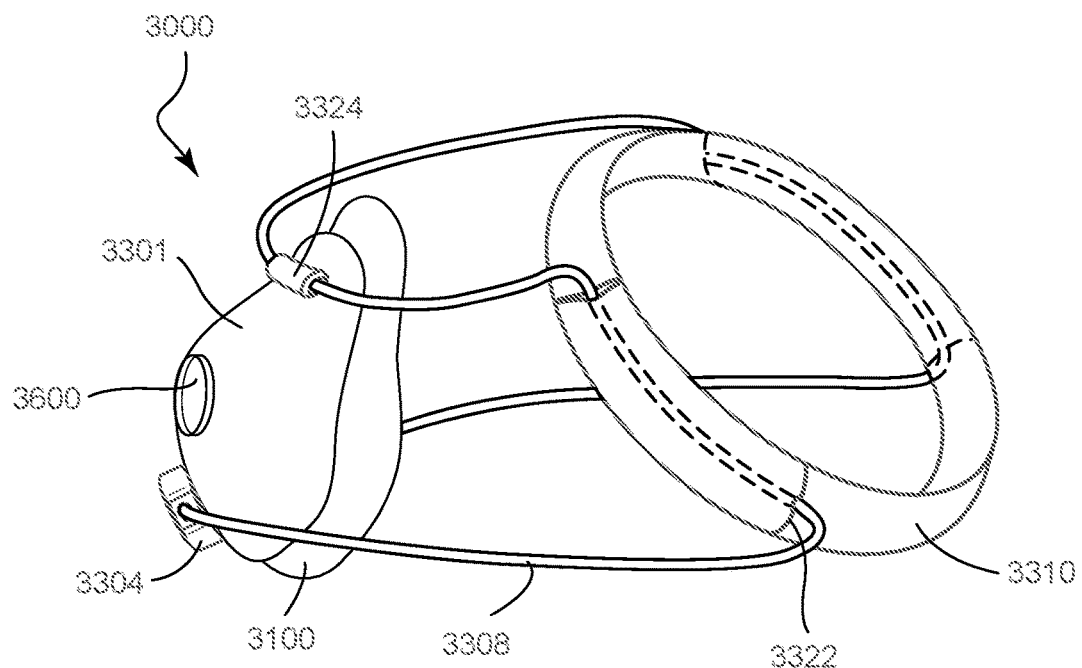

FIG. 10a shows a side view of a patient interface according to an example of the present technology.

Figure 10B:
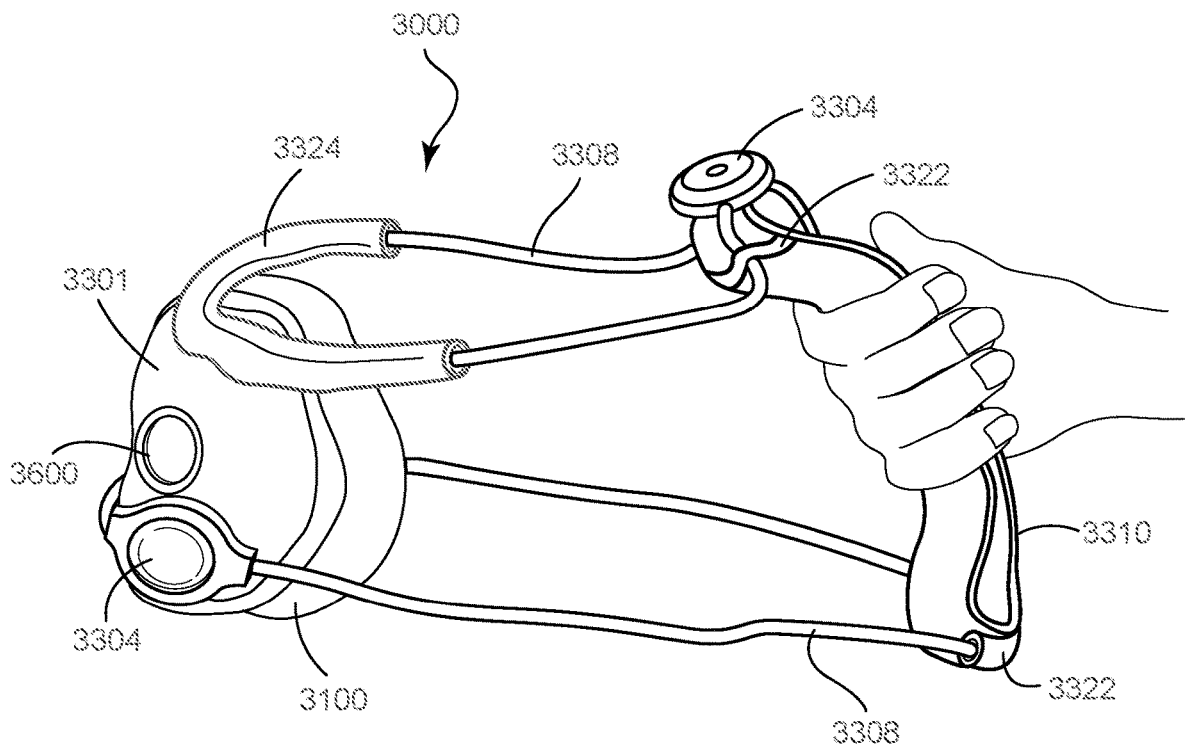

FIG. 10b shows a side view of a patient interface according to an example of the present technology.

Figure 11A:
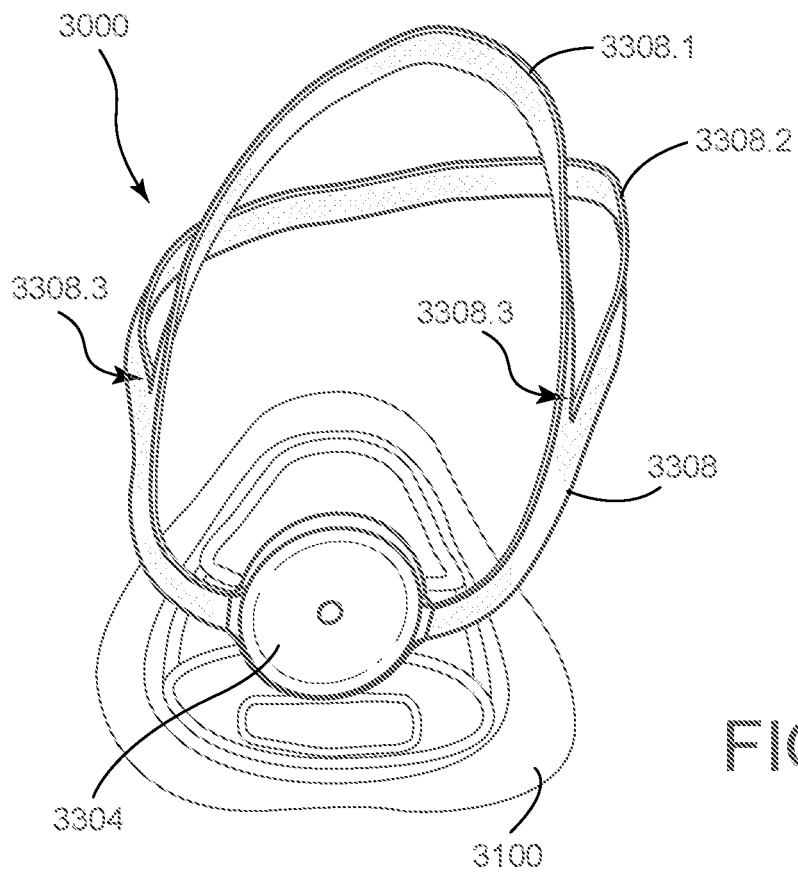

FIG. 11a shows a front view of a patient interface according to an example of the present technology.

Figure 11B:
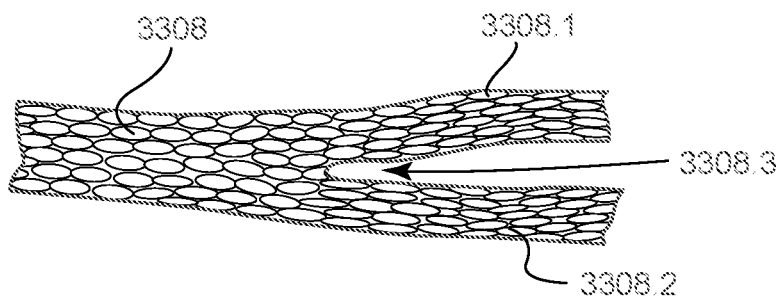

FIG. 11b shows a detailed view of a bifurcated strap of a patient interface according to an example of the present technology.

Figure 11C:
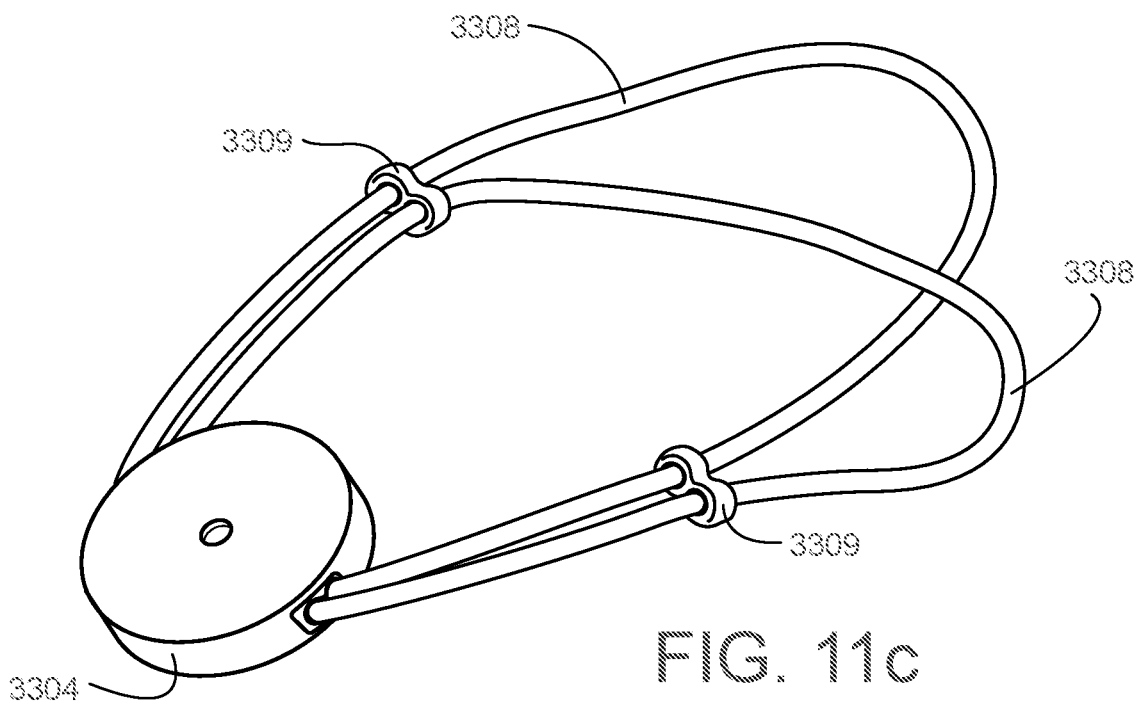

FIG. 11c shows a perspective view of a patient interface according to an example of the present technology.

Figure 11D:
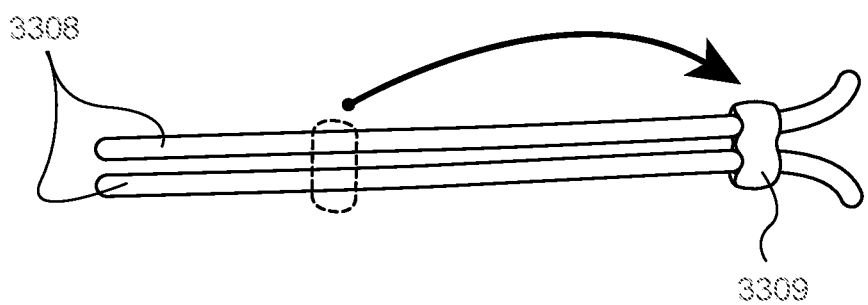

FIG. 11d shows straps and a slider for a patient interface according to an example of the present technology.

Figure 11E:
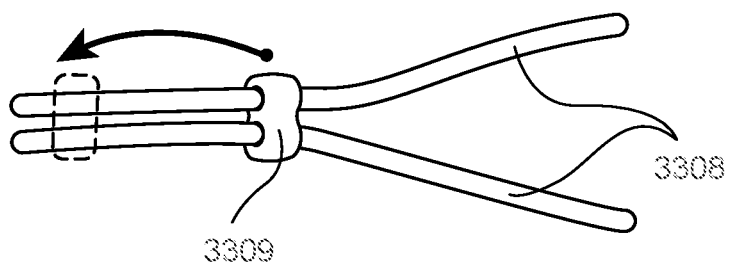

FIG. 11e shows straps and a slider for a patient interface according to an example of the present technology.

Figure 12:
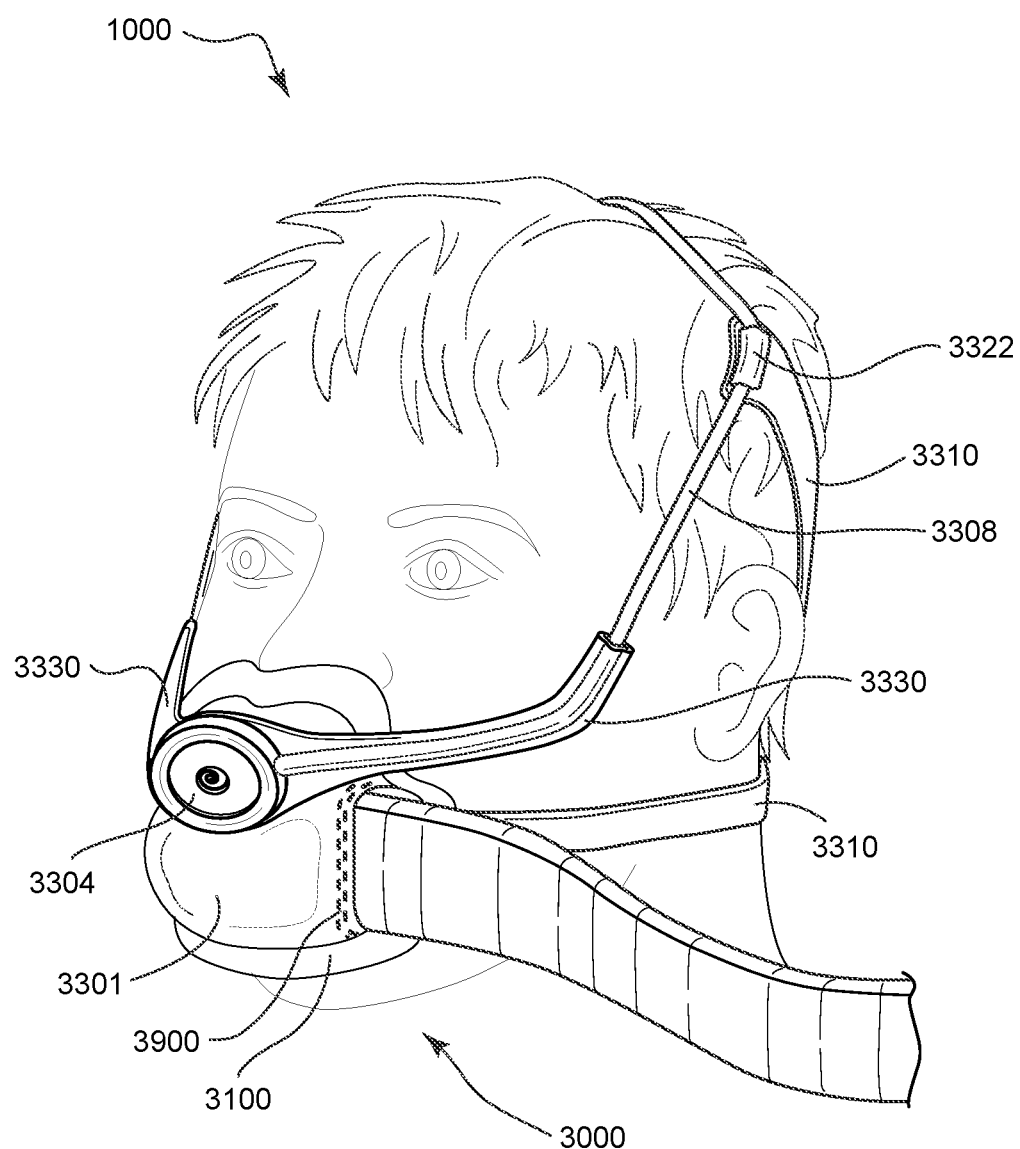

FIG. 12 shows a perspective view of a patient wearing a patient interface according to an example of the present technology.

Figure 13:
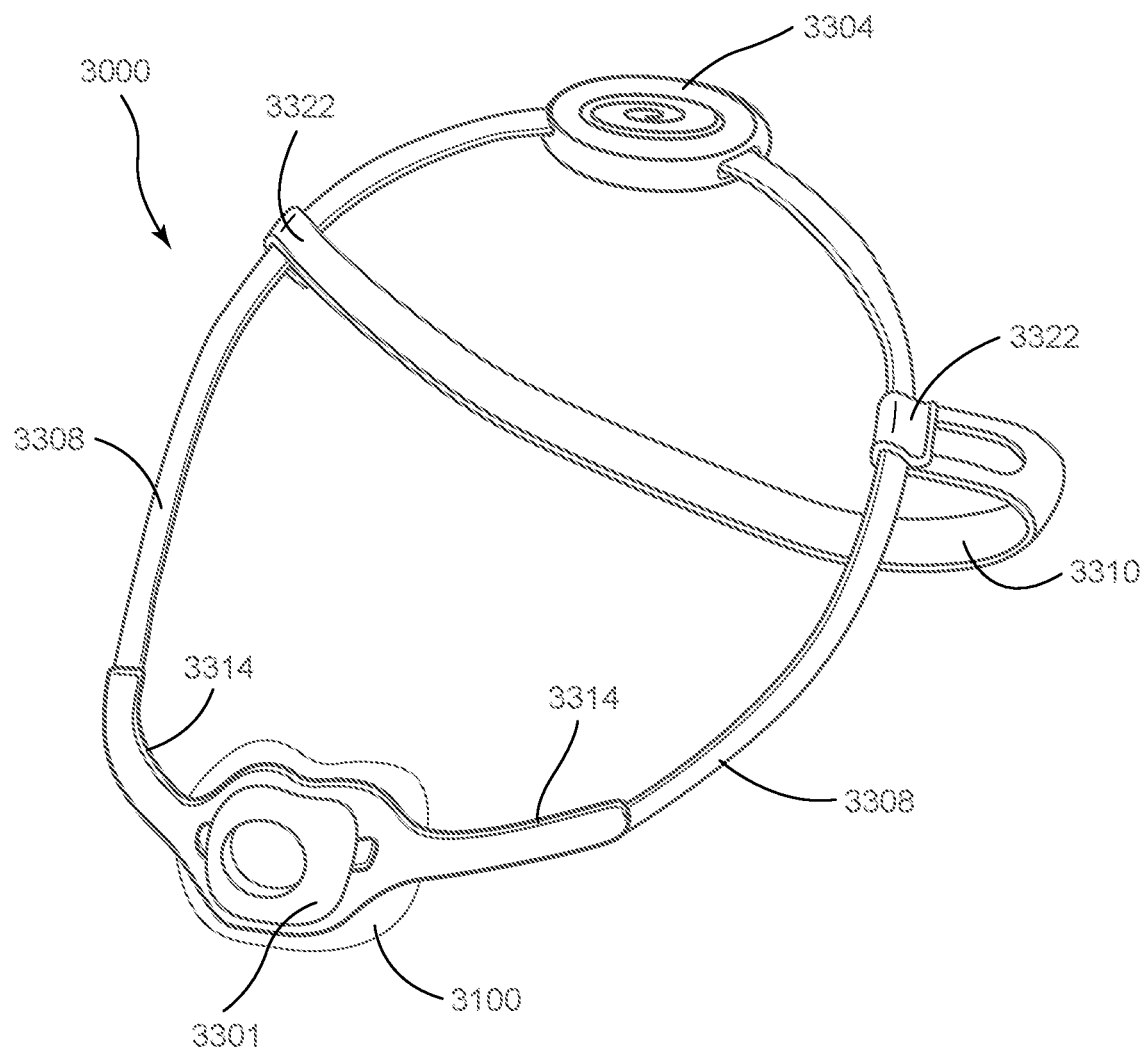

FIG. 13 shows a perspective view of a patient interface according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

5.1 Treatment Systems

In one form, the present technology comprises apparatus for treating a respiratory disorder. The apparatus may comprise a flow generator or blower for supplying pressurised respiratory gas, such as air, to the patient 1000 via an air delivery tube leading to a patient interface 3301.

5.2 Therapy

In one form, the present technology comprises a method for treating a respiratory disorder comprising the step of applying positive pressure to the entrance of the airways of a patient 1000.

5.2.1 Nasal CPAP for OSA

In one form, the present technology comprises a method of treating Obstructive Sleep Apnea in a patient by applying nasal continuous positive airway pressure to the patient.

In certain examples of the present technology, a supply of air at positive pressure is provided to the nasal passages of the patient via one or both nares.

5.3 Patient Interface

A non-invasive patient interface system 3000 in accordance with one aspect of the present technology may comprise the following functional aspects: a seal-forming structure 3100, a plenum chamber, a positioning and stabilising structure and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.3.1 Seal-Forming Structure

In one form of the present technology, a seal-forming structure 3100 may provide a sealing-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange and a support flange. The sealing flange may comprise a relatively thin member with a thickness of less than about 1 mm, for example about 0.25 mm to about 0.45 mm, that extends around the perimeter of the plenum chamber. Support flange may be relatively thicker than the sealing flange. The support flange is disposed between the sealing flange and the marginal edge of the plenum chamber, and extends at least part of the way around the perimeter. The support flange is or includes a spring-like element and functions to support the sealing flange from buckling in use. In use the sealing flange can readily respond to system pressure in the plenum chamber acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose; a stalk, a flexible region on the underside of the cone and connecting the cone to the stalk. In addition, the structure to which the nasal pillow of the present technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

5.3.2 Plenum Chamber

The plenum chamber may have a perimeter that is shaped to be complementary to the surface contour of the face of an average person in the region where a seal will form in use. In use, a marginal edge of the plenum chamber is positioned in close proximity to an adjacent surface of the face. Actual contact with the face is provided by the seal-forming structure 3100. The seal-forming structure 3100 may extend in use about the entire perimeter of the plenum chamber.

5.3.3 Positioning and Stabilising Structure

The seal-forming portion 3100 of the patient interface 3000 of the present technology may be held in sealing position in use by a positioning and stabilising structure.

5.3.3.1 Retractable Positioning and Stabilising Structure

Due to CPAP patients' heads coming in many different shapes and sizes, it may be advantageous to develop a one size fits all positioning and stabilizing structure for simplicity of fitting and sizing a patient. Existing positioning and stabilizing structure solutions use macro adjustment methods such as hook tabs and UBL (unbroken loop) fabric or ladder locks. However, a positioning and stabilizing structure that is capable of fitting a range of head sizes may also be desired to be capable of exerting the correct pressure to a patient interface to create an effective seal but avoiding excessive pressure that causes discomfort. Thus, it may be advantageous to develop positioning and stabilizing structure capable of fitting a range of head sizes while maintaining its ability to provide an optimum pressure to a patient interface.

The use of a retractable positioning and stabilizing structure, may advantageously address the problem of being able to fit various head shapes and sizes. Moreover, a retractable positioning and stabilizing structure may also have the ability to be customized, i.e., exerting a given force in between a desired range (e.g. 2.2N to 2.6N) at a given displacement (e.g. 500 mm-700 mm). Thus, the positioning and stabilizing structure can fit a much wider range of patients with an optimum force for both effective therapy and patient comfort. There is the potential to comfortably fit 100% of the adult patient population with this technology. Additionally, the straps can nearly completely retract within the reel if desired, leading to a positioning and stabilizing structure that is "non-tangle" and extremely easy to use. Moreover, the overall size of the positioning and stabilizing structure may be reduced with its ability to completely retract and, therefore, may result in easier packaging and portability.

5.3.3.1.1 Retractor(s) on the Patient Interface

FIGS. 4a to 4f show an example of a patient interface system 3000 with a patient interface 3301 having a retractable positioning and stabilising structure, according to an example of the present technology. The exemplary patient interface 3301 comprises a connection port 3600 for attachment of a decoupling structure 3500 that is in turn connected to an air delivery conduit 4170. The air delivery conduit 4170 may be connected at its opposite end to a PAP device (not shown) to provide a flow of pressurized gas to the patient interface 3301 to treat sleep disordered breathing. The pressurized gas may be provided to the patient's airways via a seal-forming structure 3100, which is a nasal pillow structure in this example.

To fit the patient interface 3301 to the patient's head and retain the seal-forming structure 3100 in sealing engagement with the patient's airways a positioning and stabilising structure is provided. The exemplary positioning and stabilising structure includes a pair of retractors 3304 connected to the patient interface via joints 3306. The retractors 3304 may be connected to the strap 3308 at both of its ends. The retractors 3304 may be winding or retracting devices that wind and/or spool the strap 3308 to draw it against the patient's head when the patient interface 3301 is donned by the patient. The retractors 3304 may retract or pull the respective ends of the strap 3308 and wind it therein by the force of a wound spring. The retractors 3304 may hold the strap 3308 in tension against the patient's head with sufficient force to sealingly engage the seal-forming structure 3100 with the patient's airways. The retractors 3304 may be operable to hold the strap 3308 in tension against the patient's head without any form of active or manual retraction by the patient. In other words, the retractors 3304 may always be pulling on respective ends of the strap 3308.

According to an example of the present technology, the retractor 3304 may include a wound spring connected to the end of the strap 3308 to generate the tension force that winds the strap in the retractor and resists unwinding of the strap. The spring may have a spring rate that generates between about 2.2N and about 2.6N of tension, according to an example of the present technology. According to yet another example of the present technology, the spring may generate about 2.4N of tension in the strap 3308. These tension values have been found to generate a sufficient level of tension force to cause an effective seal of the seal-forming structure 3100 against the patient's airways such that a flow of pressurized gas, delivered at therapy pressures discussed above, does not leak from the seal-forming structure, while at the same time the patient does not experience discomfort due to the strap 3308 being too tight. It should be understand that the spring of the retractor 3304, according to an example of the present technology, would be capable of generating these tension forces over a wide range of displacement of the strap 3308, for example 500 mm to 700 mm, from the retractor.

The positioning and stabilising structure may include a pad 3302 to cushion the strap 3308 against the patient's 1000 head, as shown in FIG. 4b for example. The pad 3302 may have an opening or may be hollow to allow the strap 3308 to pass through it. The strap 3308 is indicated in broken in lines in FIG. 4a, for example, to show it passing within the pad 3302. By forming the pad 3302 with an opening or making the pad hollow, the strap 3308 may pass freely through the pad. In other words, the pad 3302 may slide freely along the strap 3308. This allows the patient 1000 to easily pull the strap 3308 from the retractors 3304 when donning the patient interface system 3000. The pad 3302 may have a smoother inner surface along its opening or hollow portion to minimize friction as the pad slides along the strap 3308. Also, the pad 3302 may have a soft external surface to cushion the patient's face and prevent irritation.

FIGS. 4c to 4e show a series of figures demonstrating the use of the retractors 3304 wherein the patient 1000 is able to extend the strap 3308 by pulling the pad 3302 and allowing extension to fit around the head. In FIG. 4c the patient 1000 holds the patient interface 3301 with one hand and holds the pad 3302 with the other hand. In FIG. 4c, the patient 1000 may be just beginning to pull the strap 3308 from the retractors 3304. FIG. 4d shows the patient 1000 beginning to don the patient interface system 3000 by pulling the strap 3308 and the pad 3302 over the head. The strap 3308 may be sufficiently long such that it is wider than the circumference of the entire population's head. This will allow the patient 1000 to have sufficient excess strap 3308 to pull the strap around the head and then fit the patient interface 3301 by allowing the strap to retract in the retractors. FIG. 4e shows the patient 1000 with the patient interface system 3000 nearly donned. The pad 3302 can be seen near the back of the head and the seal-forming structure 3100 may be engaged with the patient's airways, the nose in this example. The patient 1000 may use one hand to adjust the engagement of the seal-forming structure 3100 with the airways and the other hand may be used to bring the pad 3302 into comfortable engagement with the back of the head. As can be seen in these examples, the pad 3302 may be located against an upper and rear portion of the patient's 1000 head such that the strap 3308 passes above the patient's ears and below the patient's eyes. This may be advantageous in that it allows for minimal obstruction of the patient's vision and minimal discomfort by not having the strap 3308 pressed against the ears.

The joints 3306 may be made of a flexible material, e.g., a material that is less rigid than material(s) of the patient interface 3301. This may allow the strap 3308 to be directed along the sides of the patient's 1000 head above the ears and below the eyes by affording some amount of flexibility to direct the tension force vectors of the strap 3308 in this direction. Furthermore, this may allow for a better fit with a variety of head shapes and sizes because the patient interface 3301 is relatively flexible in its engagement with the patient 1000 while the strap 3308 and the pad 3302 are placed in a comfortable position on the head. Moreover, the joints 3306 being relatively flexible may be beneficial in that this flexibility allows for some compensation of movement of the patient's 1000 head, for example. Also, tube torque generated by the air delivery conduit 4170 may be partially compensated by joints 3306 that are flexible.

A further example of the present technology, shown in FIG. 4g, is envisioned to include a single retractor 3304, rather than the pair of retractors 3304. In the place of one of the retractors 3304, one of the strap's 3308 ends may be fixedly attached to the patient interface 3301 or the joint 3306. This may provide for an asymmetric retraction of the strap 3308, rather than the symmetric retraction provided by a pair of retractors 3304. However, by virtue of the pad 3302 being able to slide along the length of the strap 3308, the patient 1000, when donning the patient interface system 3000 can grasp the pad and pull the strap from the retractor in a manner that would appear no different to the patient 1000 due to the slidable nature of the pad. Thus, the pad 3302 may be easily located by the patient 1000 on the back of the head, as shown in FIG. 4b for example, without a second retractor 3304 because the pad can be slid along the strap 3308 to the desired position, while the retractor provides adequate tension forces as described above.

FIGS. 7a and 7b show further examples of a patient interface system 3000 according to an example of the present technology. The patient interface 3301 according to these examples may be fitted with a seal-forming structure 3100 in the form of nasal pillows. The strap 3308 may be retracted in a single retractor 3304. The retractor 3304 may be fixedly attached to the patient interface 3301. The retractor 3304 may provide for retraction of both ends of the strap 3308 by a wound spring enclosed therein and the both ends of the strap may be connected to the spring to provide a dual winding function. In other words, both ends of the strap 3308 may be understood to be windable internally in the retractor 3304 in the same direction because they are both wrapped in the same direction. Additionally, it should also be understood that the retractor 3304 may have retract the strap without any patient actuation. In other words, it may be understood to be automatic. Although not shown in these views, the strap 3308 may be equipped with a pad 3302 to cushion the patient's head against the strap. Accordingly, the pad 3302 may be slidable along the strap 3308 for a comfortable fit, as discussed in relation to other examples.

FIG. 7b shows a variation of the example of FIG. 7a. In the example of FIG. 7b, a similar arrangement is depicted, however, rigidiser arms 3330 are shown as well. The rigidiser arms 3330 may serve as guide channels to direct the strap 3308 above the patient's ears and below the patient's eyes, for example, when the patient interface 3301 is engaged with the patient's airways. The rigidiser arms 3330 may be structured to allow the strap 3308 to pass freely therethrough. The rigidiser arms 3330 may provide for more stability to retain the strap 3308 in the desired position when the patient interface 3301 is in sealing engagement with the patient's airways. The rigidiser arms 3330 may also function to direct the tension force vectors generated by the strap 3308 when it is placed under tension due to the retractor 3304. Furthermore, the rigidiser arms 3330 may help to retain the seal-forming structure's 3100 sealing engagement with the patient's airways when the patient interface system is subjected to disruptive forces due to moving of the patient's head, for example. The rigidiser arms 3330 may be made from a deformable material. The rigidiser arms 3330 may be made from a material that is less rigid than a material(s) of the patient interface 3301. The rigidiser arms 3330 may be flexible to conform to the patient's face. The rigidiser arms 3330 may be generally flexible in respective planes parallel to the patient's Frankfort horizontal (see FIG. 2e) to accommodate for various head widths. The rigidiser arms 3330 may be relatively inflexible, i.e., the rigidiser arms may resist movement, in respective planes parallel to the patient's sagittal plane (see FIG. 2c) to prevent the rigidiser arms and/or the strap 3308 from moving across the patient's eyes or across the patient's ears. The rigidiser arms 3330 are shown with the strap 3308 exposed along the length of the rigidiser arms 3330, however, it should be understood that the rigidiser arms may be formed such that the strap may be enclosed along its length within the rigidiser arms.

While FIGS. 7a and 7b do not depict a connection port 3600 for connecting an air delivery conduit 4170 to the patient interface 3301, it should be understood that a connection port may be provided on the patient interface. For example, multiple connection ports 3600 may be provided on lateral, upper, and lower sides of the patient interface 3301 to afford flexibility in attachment of the air delivery conduit. In any event, it is envisioned that the air delivery conduit 4170 would be attachable to a connection port 3600 of the patient interface 3301 at a suitable location to provide a flow of pressurized gas to the patient, when the patient interface system is worn.

FIG. 12 shows a further example of the present technology where rigidiser arms 3330 are included. A single retractor 3304 is provided on the patient interface 3301 in this example to retract both ends of a strap 3308. The strap 3308 also passes enclosed through rigidiser arms 3330. The strap 3308 then passes through channels 3322 of a cushion 3310 that is retained against the rear of the head. The strap 3308 may pass below the patient's eyes and above the patient's ears. The rigidiser arms 3330 may aid in directing the strap 3308 along the desired path and the rigidiser arms may also help to direct the tension force vectors of the strap. The cushion 3310 can be seen extending below the patient's ears and may connect to the patient interface 3301, although the connection is not shown. The strap 3308, after passing through the channels 3322, may be directed over the top of the patient's head.

FIGS. 8a to 8c show views of a variation of the examples depicted in FIGS. 4a to 4f. In FIGS. 8a to 8c, additional pads 3303 may be provided to serve a further cushioning function against additional regions of the patient's 1000 face, for example the cheeks. The additional pads 3303, similar to the pad 3302, may be hollow or have an opening such that they can freely move or slide along the length of the strap 3308. This may allow for comfortable positioning of the additional pads 3303 as desired by the patient the face. While the additional pads 3302 are shown cushioning the cheek regions in these views, it should be understood that other areas may be cushioned additionally or alternatively as desired, such as the area where the upper portion of the ear joins the head, i.e., Otobasion superior (see FIG. 2d). The additional pads 3303 may be slidable along the length of the strap 3308 to cushion whatever areas the patient wishes to cushion. These views show a pair of additional pads 3303, however, it should also be understood that more than two additional pads may be provided along the length of the strap 3308 such that all areas of the patient's head desired to be cushioned can be cushioned. FIG. 8c shows the patient interface system with the strap 3308 in a retracted state and the pad 3302 is pulled adjacent to the additional pads 3303. The additional pads 3303 may be made of the same material(s) as the pad 3302, as described above, or may be made from different material(s). For example, the additional pads 3303 may include a smooth inner surface to minimize friction with the strap 3308. The additional pads 3303 may be made from soft external material to minimize patient irritation. The additional pads 3303 may be of the same dimensions as the pad 3302, or the additional pads may be larger or smaller, as desired to provide the desired additional cushioning. It should also be understood that the air delivery conduit 4170 is not depicted in these views for the sake of simplicity, but it is envisioned that these examples would include an air delivery conduit attached to the connection port 3600.

FIGS. 9a to 9f show further examples of the present technology with a pair of retractors 3304 fixedly attached to the patient interface 3301. The retractors 3304 may be arranged on the patient interface 3301 such that one retractor is vertically higher than the other, e.g., in a plane parallel to the patient's sagittal plane, when the patient interface is donned by the patient. Two straps 3308 may also be provided. One strap 3308 may pass above the patient's ears and below the patient's eyes when the patient interface system is worn by the patient. Also, another strap 3308 may pass below the patient's ears when the patient interface system is worn by the patient. Both ends of each strap 3308 may be connected to one of the two retractors 3304. The retractors 3304 may, accordingly, operate similar to the retractors described in relation to FIGS. 7a and 7b in that the retractors are capable of providing tension to both ends of the strap 3308 by winding both ends internally in the same direction. Alternatively, the retractors 3304 may only be connected to one end of each strap 3308, the other end being fixed to patient interface 3301. This arrangement would provide for the asymmetric retraction described above in relation to the alternative example shown in FIG. 4g. In either arrangement, each strap 3308 may be provided with a pad 3302 to cushion each respective strap against the patient's head. Accordingly, each pad 3302 may be free to slide along the length of the respective straps 3308. Furthermore, it is envisioned that the additional pads 3303 may also be provided to the strap 3308 as desired. These examples also show that the patient interface 3301 may be a full-face mask and the seal-forming structure 3100 may be structured to seal around the patient's nose and mouth together. Additionally, a retractor retainer 3305 may also be provided to retain the retractors 3304 on the patient interface 3301.

FIGS. 9c to 9f show a sequence of fitting the patient interface system 3000 according to an example of the present technology. In FIG. 9c, the patient 1000 is gripping the pads 3302 with one hand and the patient interface 3301 with the other hand to pull and extend the straps 3308. FIG. 9d shows the straps 3308 extended further and pulled over the head. In FIG. 9d the patient interface 3301 is beginning to engage with the patient's face and the seal-forming structure 3100 is being located as desired. Also, the patient 1000 is beginning to place the pads 3302 on the back of the head. FIG. 9e shows the seal-forming structure 3100 engaged with the patient's 1000 face and the patient 1000 is adjusting the location of the pads 3302 and the straps 3308. FIG. 9f shows the patient interface system fitted on the patient 1000. The seal-forming structure 3100 of the patient interface 3301 is engaged with the patient's face. The straps 3308 are also positioned on the patient's head such that one strap passes above the patient's ears and below the eyes and another strap passes below the patient's ears. Furthermore, the pads 3302 are engaged with the back of the head to cushion against the strap.

FIGS. 9a to 9f do not show a connection port 3600 or air delivery conduit 4170. However, it should be understood that the connection port 3600 may be provided at a convenient location on the patient interface 3301 so that the retractors 3304 may be fixed as desired.

FIGS. 11*a* to 11*e* show further examples of the patient interface system wherein the strap 3308 may be bifurcated. Bifurcating the strap 3308 may allow the strap to engage upper and rear portions of the patient's head to provide a more stable fit. Also, by spreading out the strap 3308, forces against the patient's head may be spread out and reduced.

FIGS. 11*a* and 11*b* show a single strap 3308 split at bifurcation points 3308.3 into an upper strap 3308.1 and a lower strap 3308.2. When the patient dons the patient interface system, the strap 3308 may pass above the patient's ears and below the patient's eyes. The upper strap 3308.1 may then extend toward and pass over the top of the patient's head, while the lower strap 3308.2 may pass toward and around the rear of the patient's head.

FIGS. 11*c* to 11*e* show an alternative example of bifurcation of the strap 3308. In these views, a pair of straps 3308 is each connected at both ends to a retractor 3304 that retracts both ends of each strap. A pair of sliders 3309 is also provided on the straps 3308. The sliders 3309 have two hollow portions that allow each strap to pass through as the sliders are slid along the strap. As shown in FIGS. 11*d* and 11*e*, the sliders 3309 may be moved along the straps 3308 to adjust the position of bifurcation. This may be advantageous to provide the benefits of a bifurcated strap arrangement while allowing the strap to fit a larger range of heads. Moving the sliders 3309 together would bring the bifurcations together allowing smaller upper and rear portions of a patient's head to be accommodated. While FIG. 11*c* does not show a patient interface 3301, it should be understood that the strap 3308 arrangement shown in this view could be accommodated on a patient interface 3301 as shown in FIG. 11*a*.

It is envisioned that any of the patient interface systems 3000 discussed above that include one or more retractors 3304 fixed to the patient interface 3301 may include additional pads 3303 to cushion the patient's cheeks and/or other head and/or facial regions against the strap(s) 3308. These additional pads 3303 may be hollow, tubular, and/or include an opening through which the strap(s) 3308 may freely pass. The additional pads 3303 may comprise a smooth internal surface to minimize friction with the at least one strap(s) 3308. The additional pads 3303 may include a soft external material to prevent irritation of the patient's skin as well. The material(s) of the additional pad 3303 may also be breathable to allow the patient's skin to ventilate through the additional pad. Also, the external material(s) of the additional pad 3303 may also provide for generation of a slight amount of friction with the patient's skin/hair such that the additional pad is capable of maintaining a desired position on the patient's head. It may be that the external material(s) of the additional pad 3303 is selected such that friction generated between external material(s) and the patient is higher than friction generated between the internal material(s) of the additional pad and the strap 3308. This may prevent the strap 3308 from dragging the additional pad 3303 across the patient to an undesired position by allowing the strap to slide freely therethrough.

It is also envisioned that the pad 3302 of any of the patient interface systems 3000 discussed above may include a smooth, internal surface on the opening, tubular, or hollow portion to minimize friction between the pad and the strap(s) 3308. The pad 3302 may also comprise a soft external material to prevent irritation of the patient's skin. The material(s) of the pad 3302 may also be breathable to allow the patient's skin to ventilate through the additional pad. Also, the external material(s) of the pad 3302 may also provide for generation of a slight amount of friction with the patient's skin/hair such that the pad is capable of maintaining a desired position on the patient's head. It may be that the external material(s) of the pad 3302 is selected such that friction generated between the external material(s) and the patient is higher than friction generated between the internal material(s) of the pad and the strap 3308. This may prevent the strap 3308 from dragging the pad 3302 across the patient to an undesired position by allowing the strap to slide freely therethrough.

It is envisioned that any of the patient interface systems 3000 discussed above that include one or more retractors 3304 fixed to the patient interface 3301 may include a joint 3306 to attach the retractor to the patient interface. The joint 3306 may comprise a material that is less rigid than the patient interface 3301 to allow the retractor 3304 to be flexed into a desired position and direct the strap(s) 3308 along the patient's head as desired when the patient interface system 3000 is donned and the strap(s) is under tension.

The strap(s) 3308 may comprise an inelastic material. The strap(s) 3308 may have a substantially rectangular cross-section. Alternatively, the strap(s) 3308 may have a substantially circular cross-section. The strap(s) 3308 may also be hollow. The strap(s) 3308 may also comprise a braided cord, a woven tape, and/or a knitted narrow fabric. The strap(s) 3308 may also comprise a textile, a polymer, and/or a composite material. The strap(s) 3308 may also comprise built-in cushioning. The strap(s) 3308 may also comprise a soft external material to prevent irritation of the patient's skin.

The retractor(s) 3304 described above may be configured to retract each strap 3308 with a retracting force of between about 2.2N and about 2.6N. The retractor 3304 may also be able to retract each strap 3308 with a retracting force of about 2.4N. It should be understood that when a single retractor 3304 is used to place two or more straps 3308 in tension, the retractor should be able to generate the above mentioned tension forces substantially equally in each of the straps. Thus, a retractor 3304 tensioning two straps 3308 may generate a retracting force of between about 2.2N and about 2.6N or about 2.4N, in each of the two straps. This may be accomplished by doubling the spring rate because both straps 3308 may be wound by the spring in the same direction.

The retractor 3304 may generate the desired tension forces by placing a wound spring, fixed at one end to a housing of the retractor and connected to at least one strap 3308 end at the other end, into tension. The end of the spring connected to the strap 3308 end may be directly connected to the strap end or an internal connection piece may be provided to serve an intermediate connecting function.

The retractor(s) 3304 may be fixedly attached to the patient interface 3301. For example, the retractor(s) 3304 may be overmolded to the patient interface 3301 or other mechanical interlock. The retractor(s) 3304 may be permanently connected to the patient interface 3301. The retractor(s) 3304 also may be attached by adhesive.

The retractors 3304 that are structured to retract more than one strap 3308 may be capable of performing the retraction of each strap substantially simultaneously.

Also, the retractors 3304 of the various examples described above may be structured to automatically retract the respective strap(s) 3308. In other words, patient actuation may not be required to retract the strap(s) 3308 and the retractors 3304 may hold the strap(s) in tension at all times.

Alternatively, it is envisioned that patient actuation may be required to start and stop retraction by the retractors 3304. A button or actuator may be provided to the retractor 3304 to facilitate the retraction in such examples.

The exemplary patient interface systems 3000 described above should be understood to include a seal-forming structure 3100 structured to form a seal with the patient's airways. A plenum chamber may also be included to connect the seal-forming structure 3100 to the patient interface 3301. The various examples depicted and described are shown with specific seal-forming structures 3100 structured to form a seal with the patient's nose and/or mouth. It should be understood that any of the above described examples may be compatible with nasal pillows, a nasal cushion, a full-face mask, an oral mask, or an oro-nasal mask.

Some of the examples of patient interface systems 3000 described above may have been depicted without a connection port 3600, a decoupling structure 3500, and an air delivery conduit 4170. It is envisioned that any of these examples may include a connection port 3600, a decoupling structure 3500, and an air delivery conduit 4170 to provide the flow pressurized gas to the patient wearing the patient interface system 3000. The connection port 3600 should be understood to be able to be provided on the patient interface 3301 at any suitable location based upon, for example, the desired position of the retractor(s) 3304.

5.3.3.1.2 Retractor(s) not on the Patient Interface

FIGS. 5a and 5b show side and front perspective views of a patient interface system donned on a patient 1000, according to an example of the present technology. FIG. 5c shows a side view of the exemplary patient interface. According to these examples, the patient interface system 3000 may include a patient interface 3301 and a seal-forming structure 3100. According to the depicted examples, the seal-forming structure 3100 is nasal pillows, however, a nasal cushion, a full-face mask, oral mask, and oro-nasal mask are also envisioned. A cushion 3310 that at least partially conforms to the patient's head is also included. A pair of retractors 3304 is fixedly attached to the cushion 3310 at opposite sides. A pair of straps 3308 may be included with an end of each of the pair of straps 3308 fixedly attached to the patient interface 3301 at attachment points 3312. The other end of each of the pair of straps 3308 is connected to one of the pair of retractors 3304.

The cushion 3310 may be a one-piece crown cushion having a substantially circular shape to follow the shape of the upper and rear portions of the patient's 1000 head. The cushion 3310 according to the depicted example may have a saddle-like shape, as can be seen for example in FIG. 5c. The retractors 3304 may be attached to the cushion 3310 at portions of the cushion that correspond to lateral sides of the patient's head, as shown in FIGS. 5a and 5b. The cushion 3310 may be formed from a soft, flexible composite material, for example Breathe-o-prene®. The cushion 3310 may also include a relatively rigid structural component to help the cushion maintain the shape shown in FIG. 5c, for example. The relatively rigid structural material may be covered partially or completely by a softer material to prevent irritation and discomfort for the patient.

The patient interface 3301 may include a connection port 3600 to receive a decoupling structure 3500 that may in turn connect an air delivery conduit 4170. The attachment points 3312 may be formed integrally with the patient interface 3301 or the attachment points may be separate components fixedly attached by adhesive, mechanical connection, etc.

The retractors 3304 may provide retraction of the ends of the respective straps 3308 without any actuation by the patient, similar to the retractors described elsewhere herein.

FIGS. 5d to 5f show a sequence of views of a patient 1000 donning a patient interface system 3000. FIG. 5d shows the patient 1000 grasping a portion of the cushion 3310 with one hand and holding the patient interface 3301 with another hand. The patient 1000 is pulling the patient interface 3301 away from the cushion 3310 to extend the straps 3308 so that the cushion can be pulled over the head. FIG. 5e shows the patient 1000 fitting the cushion 3310 on the head. A portion of the cushion 3310 is engaged with the top of the head and the patient's 1000 hand is fitting the rear portion of the cushion against the back of the patient's head. While fitting the cushion 3310, the patient 1000 is holding the patient interface 3301 away from the patient's face. FIG. 5f shows the cushion 3310 fitted to the patient's 1000 head and the patient interface 3301 is engaged to patient's face with the seal-forming structure 3100 engaged with the patient's airways. In FIG. 5f, the tension forces generated by the retractors 3304 are holding the seal-forming structure 3100 in sealing engagement with the patient's airways. It can also be seen that the straps 3308 may be directed above the patient's 1000 ears and below the patient's eyes when the patient interface system 3000 is donned on the patient.

FIG. 5g shows a further example of the present technology. The patient interface system 3000 shown in FIG. 5g is similar to the examples shown in FIGS. 5a to 5f, however, rigidiser arms 3314 may be provided as well to fixedly connect the straps 3308 to the patient interface 3301. The rigidiser arms 3314 may provide for more stability to retain the strap 3308 in the desired position when the patient interface 3301 is in sealing engagement with the patient's airways. The rigidiser arms 3314 may also function to direct the tension force vectors generated by the strap 3308 when it is placed under tension due to the retractor 3304. Furthermore, the rigidiser arms 3314 may help to retain the seal-forming structure's 3100 sealing engagement with the patient's airways when the patient interface system is subjected to disruptive forces due to moving of the patient's head, for example. The rigidiser arms 3314 may be made from a deformable material. The rigidiser arms 3314 may be made from a material that is less rigid than a material(s) of the patient interface 3301. The rigidiser arms 3314 may be flexible to conform to the patient's face. The rigidiser arms 3314 may be generally flexible in respective planes parallel to the patient's Frankfort horizontal (see FIG. 2e) to accommodate for various head widths. The rigidiser arms 3314 may be relatively inflexible, i.e., the rigidiser arms may resist movement, in respective planes parallel to the patient's sagittal plane (see FIG. 2c) to prevent the rigidiser arms and/or the strap 3308 from moving across the patient's eyes or across the patient's ears.

FIG. 5f shows a further variation of the example depicted in FIG. 5h. The rigidiser arms 3314 may be included, however, the cushion may comprise two parts, a top cushion 3310.1 and a rear cushion 3310.2. The top cushion 3310.1 may fit to the top of the patient's 1000 head and the rear cushion 3310.2 may fit to the rear of the patient's head. The retractors 3304 may be fixedly attached to opposite sides of the rear cushion 3310.2. The straps 3308 may pass from the rigidiser arms 3314 toward and through a loop 3310.3 at each end of the top cushion 3310.1 and then to the retractors 3304. The strap 3308 can be seen in FIG. 5h passing above the patient's 1000 ear and below the patient's eye.

FIG. 6a shows another exemplary patient interface system 3000. The patient interface system 3000 may include a pair of retractors 3304 and a pair of straps 3308. Each of the pair of retractors 3304 may be configured to retract both ends of each of the pair of straps 3308, as described elsewhere herein. The retractors 3304 may be fixedly attached to a retractor cushion 3318 that may fit to an upper and/or rear portion of the patient's 1000 head. A guide cushion 3316 may also be provided to direct one of the straps 3308 above the patient's ears and below the patient's eyes, while directing the other strap below the patient's ears. The straps 3308 can be seen retaining the seal-forming structure 3100 of the patient interface 3301 in sealing engagement with the patient's 1000 face. The guide cushion 3316 may include tabs 3320 to secure the straps 3308 to the guide cushion. The tabs 3320 may attach to the guide cushion 3316 by a hook and loop connection for example. The guide cushion 3316 may also fit to a rear portion of the patient's head. The straps 3308 may pass freely through the guide cushion 3316. The retractor cushion 3318 may be formed from a soft, flexible composite material, for example Breathe-o-prene®. The retractor cushion 3318 may also comprise a relatively rigid structural component that may be covered with a softer material to prevent patient discomfort. The guide cushion 3316 may be formed from a soft, flexible composite material, for example Breathe-o-prene®. The guide cushion 3316 may also comprise a relatively rigid structural component that may be covered with a softer material to prevent patient discomfort.

FIG. 6b shows another example of the patient interface system 3000, according to an example of the present technology. The patient interface system 3000 may include a pair of retractors 3304 and a pair of straps 3308. Each of the pair of retractors 3304 may be configured to retract both ends of each of the pair of straps 3308, as described elsewhere herein A pair of retractor cushions 3318 may be fixedly attached to the pair of retractor cushions. One retractor 3304 and one retractor cushion 3318 may be seen at the top of the patient's head to direct one of the straps 3308 above the patient's ears and below the patient's eyes. The other retractor 3304 and retractor cushion 3318 may be seen located at the back of the patient's head directing the other strap 3308 below the patient's ears. The straps 3308 can be seen retaining the seal-forming structure 3100 of the patient interface 3301 in sealing engagement with the patient's 1000 face. The retractor cushion 3318 may be formed from a soft, flexible composite material, for example Breathe-o-prene®. The retractor cushion 3318 may also comprise a relatively rigid structural component that may be covered with a softer material to prevent patient discomfort.

FIG. 6c shows another example of the patient interface system 3000. The patient interface system 3000 may include a crown cushion 3310 and a pair of straps 3308, each connected to the patient interface 3301 at one end and a single retractor 3304 at the other end. The retractor 3304 may be disposed on the crown cushion 3310 such that the retractor is located above the patient's head when the patient interface system 3000 is donned by the patient. The retractor 3304 may be configured to retract an end of each of the pair of straps 3308, as described elsewhere herein by winding both straps in the same direction. The crown cushion 3310 may also include a channel 3322 on each side of the retractor 3304 to direct a strap 3308 above the patient's ears and below the patient's eyes when the patient interface system is donned by the patient. The patient interface 3301 may include a seal-forming structure 3100 that is shown in this example as nasal pillows. However, it should be understood that full-face masks, nasal cushions, oral masks, and oronasal masks may also be used.

FIG. 6d shows a further example of the patient interface system 3000, according to an example of the present technology. The patient interface system 3000 may include a crown cushion 3310 and a single strap 3308. A single retractor 3304 may be disposed on the crown cushion 3310 such that the retractor is located above the patient's head when the patient interface system 3000 is donned by the patient. The retractor 3304 may be configured to retract both ends of the strap 3308. The patient interface system 3000 may also include a pair of patient interface channels 3324, each connected to an opposite side of the patient interface 3301. The strap 3308 may pass freely through each of the pair of patient interface channels 3324 such that two portions of the strap 3308 are directed below the patient's eyes and above the patient's ears when the patient interface system is donned by the patient. The crown cushion 3310 may also include a cushion channel 3322 and the strap may pass freely through the cushion channel such that two portions of the strap are directed below the patient's ears when the patient interface system is donned by the patient.

FIG. 6f shows a further variation of the example of the patient interface system 3000 of FIG. 6d. In this depicted example, each of the pair of patient interface channels 3324 may be spaced from the patient interface 3301 by an extension 3328. A single strap 3308 may again be provided that may pass behind the lower, rear portion of the patient's 1000 head and be directed by cushion channels 3322. An upper portion of the strap 3308 can be seen passing above the patient's ears and below the eyes, while a lower portion of the strap can be seen passing below the ears.

FIG. 6e shows another example of a patient interface system 3000, according to the present technology. The patient interface system 3000 may include a crown cushion 3310 and a pair of straps 3308. Each of the pair of straps 3308 may be connected to the patient interface 3301 at one end by a connection point 3326. The patient interface system 3000 may include a single retractor 3304 disposed on the crown cushion 3310 such that the retractor is located above the patient's head when the patient interface system is donned by the patient. The retractor 3304 may be configured to retract one end of each of the pair of straps 3308 simultaneously, as described elsewhere herein. The patient interface 3301 may have a pair of patient interface channels 3324, each disposed on an opposite side of the patient interface such that each strap 3308 may pass freely through each of the pair of patient interface channels. An upper portion of each strap 3308 may be seen directed below the patient's 1000 eyes and above the patient's ears when the patient interface system 3000 is donned by the patient. The crown cushion 3310 may comprise a pair of cushion channels 3322 and each of the pair of straps 3308 may pass freely through the respective cushion channels such that two portions of each strap is directed below the patient's 1000 ears. Furthermore, each of the pair of straps 3308 may be doubled back through a respective cushion channel 3322 when the patient interface system 3000 is donned by the patient 1000.

FIG. 13 shows another example of a patient interface system 3000 in accordance with the present technology. The exemplary patient interface system 3000 shown here may be a variation of the example shown in FIG. 6c. For example, the cushion 3310 may be elongate and/or rectangular in shape, rather than a circular shape, as depicted in FIG. 6c. The retractor 3304 may be located on top of the patient's head and may retract one end of each of a pair of straps 3308 substantially simultaneously and without patient actuation. Each of the pair of straps 3308 may pass freely through a channel 3322 located at each end of the cushion 3310. The channels 3322 may help to direct the straps 3308 above the patient's ears and below the patient's eyes. Also, the cushion 3310 may be structured to fit on a lower and/or rear portion of the patient's head. FIG. 13 also shows that ends of the straps 3308 are fixedly attached to the patient interface 3301 via rigidiser arms 3314. The rigidiser arms may also help to direct the straps 3308 above the patient's ears and below the patient's eyes. It is also envisioned that the patient interface 3301 may not include the rigidiser arms 3314. Instead, ends of the straps 3308 may be fixed directly to the patient interface 3301.

It is envisioned that any of the patient interface systems 3000 discussed above that include one or more retractors 3304 fixed to the cushion 3310 may include additional pads 3303 to cushion the patient's cheeks and/or other head and/or facial regions against the strap(s) 3308. These additional pads 3303 may be hollow, tubular, and/or include an opening through which the strap(s) 3308 may freely pass. The additional pads 3303 may comprise a smooth internal surface to minimize friction with the at least one strap(s) 3308. The additional pads 3303 may include a soft external material to prevent irritation of the patient's skin as well. The material(s) of the additional pad 3303 may also be breathable to allow the patient's skin to ventilate through the additional pad. Also, the external material(s) of the additional pad 3303 may also provide for generation of a slight amount of friction with the patient's skin/hair such that the additional pad is capable of maintaining a desired position on the patient's head. It may be that the external material(s) of the additional pad 3303 is selected such that friction generated between external material(s) and the patient is higher than friction generated between the internal material(s) of the additional pad and the strap 3308. This may prevent the strap 3308 from dragging the additional pad 3303 across the patient to an undesired position by allowing the strap to slide freely therethrough.

The cushion(s) 3310 of the various examples discussed above may be formed from a soft, flexible composite material, for example Breathe-o-prene®. The cushion(s) 3310 may also include a relatively rigid structural component to help the cushion maintain its shape. The relatively rigid structural material may be covered partially or completely by a softer material to prevent irritation and discomfort for the patient. The cushion(s) 3310 may also include a breathable external material to allow the patient's skin to ventilate therethrough.

The loops 3310.3, cushion channels 3322, and patient interface channels 3324 should all be understood to include a relatively smooth internal surface. This allows the strap(s) 3308 to pass freely through these features as the patient pulls and extends the strap(s) from the retractor(s) 3304 and as the retractor(s) retract the strap(s) to fit the patient interface system 3000 to the patient's head.

The strap(s) 3308 may comprise an inelastic material. The strap(s) 3308 may have a substantially rectangular cross-section. Alternatively, the strap(s) 3308 may have a substantially circular cross-section. The strap(s) 3308 may also be hollow. The strap(s) 3308 may also comprise a braided cord, a woven tape, and/or a knitted narrow fabric. The strap(s) 3308 may also comprise a textile, a polymer, and/or a composite material. The strap(s) 3308 may also comprise built-in cushioning. The strap(s) 3308 may also comprise a soft external material to prevent irritation of the patient's skin.

The retractor(s) 3304 described above may be configured to retract each strap 3308 with a retracting force of between about 2.2N and about 2.6N. The retractor 3304 may also be able to retract each strap 3308 with a retracting force of about 2.4N. It should be understood that when a single retractor 3304 is used to place two or more straps 3308 in tension, the retractor should be able to generate the above mentioned tension forces substantially equally in each of the straps. Thus, a retractor 3304 tensioning two straps 3308 may generate a retracting force of between about 2.2N and about 2.6N or about 2.4N, in each of the two straps. This may be accomplished by doubling the spring rate because both straps 3308 may be wound by the spring in the same direction.

The retractor 3304 may generate the desired tension forces by placing a wound spring, fixed at one end to a housing of the retractor and connected to at least one strap 3308 end at the other end, into tension. The end of the spring connected to the strap 3308 end may be directly connected to the strap end or an internal connection piece may be provided to serve an intermediate connecting function.

The retractors 3304 that are structured to retract more than one strap 3308 may be capable of performing the retraction of each strap substantially simultaneously.

The retractor(s) 3304 may be fixedly attached to the cushion(s) 3310. The retractor(s) 3304 may be sewn to the cushion(s) 3310 or other mechanical connections may be used. The retractor(s) 3304 may also be attached to the cushion(s) 3310 by adhesive.

Also, the retractors 3304 of the various examples described above may be structured to automatically retract the respective strap(s) 3308. In other words, patient actuation may not be required to retract the strap(s) 3308 and the retractors 3304 may hold the strap(s) in tension at all times. Alternatively, it is envisioned that patient actuation may be required to start and stop retraction by the retractors 3304. A button or actuator may be provided to the retractor 3304 to facilitate the retraction in such examples.

The exemplary patient interface systems 3000 described above should be understood to include a seal-forming structure 3100 structured to form a seal with the patient's airways. A plenum chamber may also be included to connect the seal-forming structure 3100 to the patient interface 3301. The various examples depicted and described are shown with specific seal-forming structures 3100 structured to form a seal with the patient's nose and/or mouth. It should be understood that any of the above described examples may be compatible with nasal pillows, a nasal cushion, a full-face mask, an oral mask, or an oro-nasal mask.

Some of the examples of patient interface systems 3000 described above may have been depicted without a connection port 3600, a decoupling structure 3500, and an air delivery conduit 4170. It is envisioned that any of these examples may include a connection port 3600, a decoupling structure 3500, and an air delivery conduit 4170 to provide the flow pressurized gas to the patient wearing the patient interface system 3000. The connection port 3600 should be understood to be able to be provided on the patient interface 3301 at any suitable location based upon, for example, the desired position of the retractor(s) 3304.

5.3.3.1.3 Further Examples

FIG. 10a shows a further example of a patient interface system 3000 according to an example of the present technology. The patient interface 3301 according to this example includes a seal-forming structure 3100, a single retractor 3304, and a patient interface channel 3324. One strap may be provided that is retracted at both ends by the retractor 3304. A cushion 3310 may be provided in the form of a crown cushion and may include a pair of cushion channels 3322. The cushion channels 3322 may serve to direct an upper portion of the strap 3308 above the patient's ears and below the patient's eyes, while a lower portion of the strap is directed below the patient's ears. While this view shows the patient interface channel 3324 attached to the patient interface 3301 above the retractor 3304, it should be understood that locating the retractor above the patient interface channel would also be possible.

FIG. 10b shows a further example of the patient interface system 3000 according to the present technology. Fixedly attached to the patient interface 3301 may be a patient interface channel 3324 and a retractor 3304. A cushion 3310 may also be provided. The cushion 3310 may be substantially circular in the form of a crown cushion. The cushion 3310 may include channels 3322 and a retractor 3304. Two straps 3308 may also be provided, one for each retractor 3304, and each retractor may be configured to retract both ends of the respective strap. The upper strap 3308 may directed by the patient interface channel 3324 and the cushion channels 3322 to direct the strap above the patient's ears and below the patient's eyes. The lower strap 3308 may also be directed by the lower cushion channel 3322 below the patient's ears.

It is envisioned that any of the patient interface systems 3000 discussed above that include one or more retractors 3304 fixed to the cushion 3310 and/or the patient interface 3301 may include additional pads 3303 to cushion the patient's cheeks and/or other head and/or facial regions against the strap(s) 3308. These additional pads 3303 may be hollow, tubular, and/or include an opening through which the strap(s) 3308 may freely pass. The additional pads 3303 may comprise a smooth internal surface to minimize friction with the at least one strap(s) 3308. The additional pads 3303 may include a soft external material to prevent irritation of the patient's skin as well. The material(s) of the additional pad 3303 may also be breathable to allow the patient's skin to ventilate through the additional pad. Also, the external material(s) of the additional pad 3303 may also provide for generation of a slight amount of friction with the patient's skin/hair such that the additional pad is capable of maintaining a desired position on the patient's head. It may be that the external material(s) of the additional pad 3303 is selected such that friction generated between external material(s) and the patient is higher than friction generated between the internal material(s) of the additional pad and the strap 3308. This may prevent the strap 3308 from dragging the additional pad 3303 across the patient to an undesired position by allowing the strap to slide freely therethrough.

The cushion(s) 3310 of the various examples discussed above may be formed from a soft, flexible composite material, for example Breathe-o-prene®. The cushion(s) 3310 may also include a relatively rigid structural component to help the cushion maintain its shape. The relatively rigid structural material may be covered partially or completely by a softer material to prevent irritation and discomfort for the patient. The cushion(s) 3310 may also include a breathable external material to allow the patient's skin to ventilate therethrough.

It is envisioned that any of the patient interface systems 3000 discussed above that include one or more retractors 3304 fixed to the patient interface 3301 may include a joint 3306 to attach the retractor to the patient interface. The joint 3306 may comprise a material that is less rigid than the patient interface 3301 to allow the retractor 3304 to be flexed into a desired position and direct the strap(s) 3308 along the patient's head as desired when the patient interface system 3000 is donned and the strap(s) is under tension.

The cushion channels 3322, and patient interface channels 3324 should all be understood to include a relatively smooth internal surface. This allows the strap(s) 3308 to pass freely through these features as the patient pulls and extends the strap(s) from the retractor(s) 3304 and as the retractor(s) retract the strap(s) to fit the patient interface system 3000 to the patient's head.

The strap(s) 3308 may comprise an inelastic material. The strap(s) 3308 may have a substantially rectangular cross-section. Alternatively, the strap(s) 3308 may have a substantially circular cross-section. The strap(s) 3308 may also be hollow. The strap(s) 3308 may also comprise a braided cord, a woven tape, and/or a knitted narrow fabric. The strap(s) 3308 may also comprise a textile, a polymer, and/or a composite material. The strap(s) 3308 may also comprise built-in cushioning. The strap(s) 3308 may also comprise a soft external material to prevent irritation of the patient's skin.

The retractor(s) 3304 described above may be configured to retract each strap 3308 with a retracting force of between about 2.2N and about 2.6N. The retractor 3304 may also be able to retract each strap 3308 with a retracting force of about 2.4N. It should be understood that when a single retractor 3304 is used to place two or more straps 3308 in tension, the retractor should be able to generate the above mentioned tension forces substantially equally in each of the straps. Thus, a retractor 3304 tensioning two straps 3308 may generate a retracting force of between about 2.2N and about 2.6N or about 2.4N, in each of the two straps. This may be accomplished by doubling the spring rate because both straps 3308 may be wound by the spring in the same direction.

The retractor 3304 may generate the desired tension forces by placing a wound spring, fixed at one end to a housing of the retractor and connected to at least one strap 3308 end at the other end, into tension. The end of the spring connected to the strap 3308 end may be directly connected to the strap end or an internal connection piece may be provided to serve an intermediate connecting function.

The retractors 3304 that are structured to retract more than one strap 3308 may be capable of performing the retraction of each strap substantially simultaneously.

The retractor(s) 3304 may be fixedly attached to the cushion(s) 3310. The retractor(s) 3304 may be sewn to the cushion(s) 3310 or other mechanical connections may be used. The retractor(s) 3304 may also be attached to the cushion(s) 3310 by adhesive.

The retractor(s) 3304 may be fixedly attached to the patient interface 3301. For example, the retractor(s) 3304 may be overmolded to the patient interface 3301 or other mechanical interlock. The retractor(s) 3304 may be permanently connected to the patient interface 3301. The retractor(s) 3304 also may be attached by adhesive.

Also, the retractors 3304 of the various examples described above may be structured to automatically retract the respective strap(s) 3308. In other words, patient actuation may not be required to retract the strap(s) 3308 and the retractors 3304 may hold the strap(s) in tension at all times. Alternatively, it is envisioned that patient actuation may be required to start and stop retraction by the retractors 3304. A button or actuator may be provided to the retractor 3304 to facilitate the retraction in such examples.

The exemplary patient interface systems 3000 described above should be understood to include a seal-forming structure 3100 structured to form a seal with the patient's airways. A plenum chamber may also be included to connect the seal-forming structure 3100 to the patient interface 3301. The various examples depicted and described are shown with specific seal-forming structures 3100 structured to form a seal with the patient's nose and/or mouth. It should be understood that any of the above described examples may be compatible with nasal pillows, a nasal cushion, a full-face mask, an oral mask, or an oro-nasal mask.

Some of the examples of patient interface systems 3000 described above may have been depicted without a decoupling structure 3500 and an air delivery conduit 4170. It is envisioned that any of these examples may include a decoupling structure 3500 and an air delivery conduit 4170 to provide the flow of pressurized gas to the patient wearing the patient interface system 3000. The connection port 3600 should be understood to be able to be provided on the patient interface 3301 at any suitable location based upon, for example, the desired position of the retractor(s) 3304.

5.3.4 Vent

In one form, the patient interface 3000 may include a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure 3500, e.g. a swivel 3510.

5.3.5 Decoupling Structure(s)

In one form the patient interface 3000 includes at least one decoupling structure 3500, for example a swivel or a ball and socket.

5.3.6 Connection Port

Connection port 3600 may allow for connection to the air circuit 4170.

5.3.7 Forehead Support

In one form, the patient interface 3000 may include a forehead support.

5.3.8 Anti-Asphyxia

In one form, the patient interface 3000 may include an anti-asphyxia valve 3900.

5.3.9 Ports

In one form of the present technology, a patient interface 3000 may include one or more ports, that allow access to the volume within the plenum chamber 3200. In one form this allows a clinician to supply supplemental oxygen. In one form this allows for the direct measurement of a property of gases within the plenum chamber 3200, such as the pressure.

5.4 Pap Device 4000

A PAP device 4000 in accordance with one aspect of the present technology comprises mechanical and pneumatic components 4100, electrical components 4200 and is programmed to execute one or more algorithms 4300. The PAP device may have an external housing 4010, formed in two parts, an upper portion 4012 of the external housing 4010, and a lower portion 4014 of the external housing 4010. In alternative forms, the external housing 4010 may include one or more panel(s) 4015. The PAP device 4000 may comprise a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 may comprise an inlet air filter 4112, an inlet muffler, a controllable pressure device capable of supplying air at positive pressure (e.g., a controllable blower 4142), and an outlet muffler. One or more pressure sensors and flow sensors may be included in the pneumatic path.

The pneumatic block 4020 may comprise a portion of the pneumatic path that is located within the external housing 4010.

The PAP device 4000 may have an electrical power supply 4210 and one or more input devices 4220. Electrical components 4200 may be mounted on a single Printed Circuit Board Assembly (PCBA) 4202. In an alternative form, the PAP device 4000 may include more than one PCBA 4202.

5.4.1 PAP Device Mechanical & Pneumatic Components

5.4.1.1 Air Filter(s)

A PAP device 4000 in accordance with one form of the present technology may include an air filter 4110, or a plurality of air filters 4110.

In one form, an inlet air filter 4112 is located at the beginning of the pneumatic path upstream of a controllable blower 4142. See FIG. 3c.

In one form, an outlet air filter 4114, for example an antibacterial filter, is located between an outlet of the pneumatic block 4020 and a patient interface 3000. See FIG. 3c.

5.4.1.2 Pressure Device

In a form of the present technology, a pressure device for producing a flow of air at positive pressure is a controllable blower 4142. For example the blower 4142 may include a brushless DC motor with one or more impellers housed in a volute. The blower 4142 may be capable of delivering a supply of air, for example about 120 litres/minute, at a positive pressure in a range from about 4 cmH2O to about 20 cmH2O, or in other forms up to about 30 cmH2O.

5.4.1.3 Pressure Device 4140

In a one form of the present technology, a pressure device 4140 for producing a flow of air at positive pressure is a controllable blower 4142. For example the blower may include a brushless DC motor 4144 with one or more impellers housed in a volute. The blower may be capable of delivering a supply of air, for example about 120 litres/minute, at a positive pressure in a range from about 4 $cmH_2O$ to about 20 $cmH_2O$, or in other forms up to about 30 $cmH_2O$.

The pressure device 4140 is under the control of the therapy device controller 4240.

5.5 Humidifier

5.5.1 Humidifier Overview

In one form of the present technology there is provided a humidifier 5000, as shown in FIG. 3b, that may comprise a water reservoir and a heating plate.

5.6 Glossary

For the purposes of the present technology disclosure, in certain forms of the present technology, one or more of the following definitions may apply. In other forms of the present technology, alternative definitions may apply.

5.6.1 General

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

5.6.2 Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

APAP: Automatic Positive Airway Pressure. Positive airway pressure that is continually adjustable between minimum and maximum limits, depending on the presence or absence of indications of SDB events.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation ($SaO_2$), partial pressure of carbon dioxide ($PCO_2$), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug.

Motor: A device for converting electrical energy into rotary movement of a member. In the present context the rotating member is an impeller, which rotates in place around a fixed axis so as to impart a pressure increase to air moving along the axis of rotation.

Positive Airway Pressure (PAP) device: A device for providing a supply of air at positive pressure to the airways.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

5.6.3 Aspects of the Respiratory Cycle

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Duty cycle: The ratio of inhalation time, Ti to total breath time, Ttot.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
 (i) Flattened: Having a rise followed by a relatively flat portion, followed by a fall.
 (ii) M-shaped: Having two local peaks, one at the leading edge, and one at the trailing edge, and a relatively flat portion between the two peaks.
 (iii) Chair-shaped: Having a single local peak, the peak being at the leading edge, followed by a relatively flat portion.
 (iv) Reverse-chair shaped: Having a relatively flat portion followed by single local peak, the peak being at the trailing edge.

Hypopnea: Preferably, a hypopnea will be taken to be a reduction in flow, but not a cessation of flow. In one form, a hypopnea may be said to have occurred when there is a reduction in flow below a threshold for a duration. In one form in adults, the following either of the following may be regarded as being hypopneas:
  (i) a 30% reduction in patient breathing for at least 10 seconds plus an associated 4% desaturation; or
  (ii) a reduction in patient breathing (but less than 50%) for at least 10 seconds, with an associated desaturation of at least 3% or an arousal.

Hyperpnea: An increase in flow to a level higher than normal flow.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory flow, airflow, patient airflow, respiratory airflow (Qr): These synonymous terms may be understood to refer to the PAP device's estimate of respiratory airflow, as opposed to "true respiratory flow" or "true respiratory airflow", which is the actual respiratory flow experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

5.6.4 PAP Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

Pressure: Force per unit area. Pressure may be measured in a range of units, including $cmH_2O$, $g-f/cm^2$, hectopascal. $1 cmH_2O$ is equal to 1 $g-f/cm^2$ and is approximately 0.98 hectopascal. In this specification, unless otherwise stated, pressure is given in units of $cmH_2O$. For nasal CPAP treatment of OSA, a reference to treatment pressure is a reference to a pressure in the range of about 4-20 $cmH_2O$, or about 4-30 $cmH_2O$. The pressure in the patient interface is given the symbol Pm.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound power is usually given in decibels SPL, that is, decibels relative to a reference power, normally taken as $20 \times 10^{-6}$ pascal (Pa), considered the threshold of human hearing.

5.6.5 Terms for Ventilators

Adaptive Servo-Ventilator: A ventilator that has a changeable, rather than fixed target ventilation. The changeable target ventilation may be learned from some characteristic of the patient, for example, a respiratory characteristic of the patient.

Backup rate: A parameter of a ventilator that establishes the minimum respiration rate (typically in number of breaths per minute) that the ventilator will deliver to the patient, if not otherwise triggered.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

EPAP (or EEP): a base pressure, to which a pressure varying within the breath is added to produce the desired mask pressure which the ventilator will attempt to achieve at a given time.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the ventilator aims to achieve, rather than what it actually achieves.

Servo-ventilator: A ventilator that measures patient ventilation has a target ventilation, and which adjusts the level of pressure support to bring the patient ventilation towards the target ventilation.

Spontaneous/Timed (S/T)—A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Ventilator: A mechanical device that provides pressure support to a patient to perform some or all of the work of breathing.

5.6.6 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricula or Pinna: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

*Glabella*: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion

5.6.7 Anatomy of the Skull

Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.6.8 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.6.9 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILAS TIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using AS™ D2240.

Polycarbonate: a typically transparent thermoplastic polymer of Bisphenol-A Carbonate.

5.6.10 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. The headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to a mean portion of a patient interface having walls enclosing a volume of space, the volume having air therein pressurised above atmospheric pressure in use. A shell may form part of the walls of a mask plenum chamber. In one form, a region of the patient's face forms one of the walls of the plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will preferably be taken to mean a curved structure having bending, tensile and compressive stiffness, for example, a portion of a mask that forms a curved structural wall of the mask. Preferably, compared to its overall dimensions it is relatively thin. In some forms, a shell may be faceted. Preferably such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. Preferably there is little or no leak flow of air from the swivel in use.

Tie: A tie will be taken to be a structural component designed to resist tension.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

5.6.11 Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principle directions, will be said to have a positive curvature. A flat surface will be taken to have zero curvature.

Floppy: A quality of a material, structure or composite that is the combination of features of:
Readily conforming to finger pressure.
Unable to retain its shape when caused to support its own weight.
Not rigid.
Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

5.7 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.8 Reference Signs List

| | |
|---|---|
| patient | 1000 |
| partner | 1100 |
| patient interface system | 3000 |
| structure | 3100 |
| plenum chamber | 3200 |
| patient interface | 3301 |
| pad | 3302 |
| additional pad | 3303 |
| retractor | 3304 |
| retractor retainer | 3305 |
| joint | 3306 |
| strap | 3308 |
| slider | 3309 |
| cushion | 3310 |
| top cushion | 3310.1 |
| rear cushion | 3310.2 |
| loop | 3310.3 |
| attachment point | 3312 |
| rigidiser arm | 3314 |
| guide cushion | 3316 |
| retractor cushion | 3318 |
| tab | 3320 |
| channel | 3322 |
| patient interface channel | 3324 |
| connection point | 3326 |
| extension | 3328 |
| rigidiser arm | 3330 |
| vent | 3400 |
| decoupling structure | 3500 |
| connection port | 3600 |
| pap device | 4000 |

| | |
|---|---|
| external housing | 4010 |
| upper portion | 4012 |
| portion | 4014 |
| panel | 4015 |
| chassis | 4016 |
| handle | 4018 |
| pneumatic block | 4020 |
| pneumatic component | 4100 |
| air filter | 4110 |
| inlet air filter | 4112 |
| outlet air filter | 4114 |
| pressure device | 4140 |
| blower | 4142 |
| controllable blower | 4142 |
| brushless DC motor | 4144 |
| air delivery conduit | 4170 |
| air circuit | 4170 |
| electrical component | 4200 |
| PCBA | 4202 |
| board Assembly PCBA | 4202 |
| electrical power supply | 4210 |
| input device | 4220 |
| therapy device controller | 4240 |
| algorithm | 4300 |
| humidifier | 5000 |

The invention claimed is:

1. A patient interface system to treat sleep disordered breathing of a patient with pressurized gas, comprising:
   a patient interface including:
   a plenum chamber configured to be pressurised above atmospheric pressure in use; and
   a seal-forming structure configured to seal with the patient's face around the patient's airways, the seal-forming structure being connected to a perimeter of the plenum chamber;
   at least one strap;
   at least one retractor fixedly attached to the patient interface, said at least one retractor connected to the at least one strap and configured to wind the at least one strap internally within the at least one retractor without patient actuation;
   a joint connecting the at least one retractor to the patient interface; and
   at least one pad to cushion a rearward portion of the patient's head, said at least one pad having an opening, wherein said at least one strap passes through said opening to allow the at least one pad to move freely relative to said at least one strap.

2. The patient interface system of claim 1, wherein said at least one retractor comprises a pair of retractors, each of the retractors being disposed on a corresponding lateral side of the patient interface, and
   wherein each of the retractors is connected to a respective end of said at least one strap.

3. The patient interface system of claim 2, wherein said at least one strap consists of a single strap, each of the retractors being configured to retract a respective end of said single strap, and
   wherein said single strap is configured to pass above the patient's ears and below the patient's eyes when the patient interface system is donned by the patient.

4. The patient interface system of claim 2, further comprising two joints, each of the joints connecting a corresponding one of the retractors to the patient interface.

5. The patient interface system of claim 4, wherein each of the joints is constructed from a flexible material.

6. The patient interface system of claim 2, wherein each of the retractors further comprises a spring configured to tension the at least one strap.

7. The patient interface system of claim 1, wherein said at least one retractor consists of a single retractor connected to a first end of the at least one strap and disposed on a first side of said patient interface, and
   wherein a second end of said at least one strap is fixedly attached to a second side of said patient interface, said second side being opposite said first side.

8. The patient interface system of claim 7, wherein the single retractor further comprises a spring configured to tension the at least one strap.

9. The patient interface system of claim 1, wherein said at least one retractor consists of a first retractor and a second retractor, said first retractor disposed on the patient interface higher than the second retractor in a plane parallel to the patient's sagittal plane,
   wherein said at least one strap consists of a first strap and a second strap and said at least one pad consists of a first pad and a second pad, each corresponding to the first strap and the second strap, and
   wherein the first retractor is structured to retract both ends of the first strap and the second retractor is structured to retract both ends of the second strap.

10. The patient interface system of claim 9, further comprising two joints, each of the joints connecting a corresponding one of the first retractor and the second retractor to the patient interface.

11. The patient interface system of claim 10, wherein each of the joints is constructed from a flexible material.

12. The patient interface system of claim 9, wherein each of the first retractor and the second retractor further comprises a spring configured to tension a corresponding one of the first strap and the second strap.

13. The patient interface system of claim 1, wherein said at least one retractor consists of a single retractor disposed centrally on the patient interface in a horizontal plane,
   wherein the at least one strap consists of a single strap, and
   wherein the single retractor is structured to retract both ends of the single strap.

14. The patient interface system of claim 13, wherein said single strap is configured to pass above the patient's ears and below the patient's eyes when the patient interface system is donned by the patient.

15. The patient interface system of claim 14, further comprising a pair of rigidiser arms, each of the rigidiser arms being disposed on a corresponding lateral side of said patient interface,
   wherein each of the rigidiser arms is structured to allow the strap to pass freely therethrough such that tension force of the strap is directed above the patient's ears and below the patient's eyes when the patient interface system is donned by the patient.

16. The patient interface system of claim 13, wherein the single retractor further comprises a spring configured to tension the single strap.

17. The patient interface system of claim 1, wherein said at least one strap consists of a pair of straps,
   wherein said at least one retractor consists of a single retractor disposed centrally on the patient interface, said single retractor being structured to retract a corresponding end of each of the pair of straps, and
   wherein a pair of sliders are each slidingly disposed on the pair of straps to provide a pair of adjustable bifurcation points between the pair of straps.

18. The patient interface system of claim 1, further comprising additional pads to cushion the patient's cheeks against the at least one strap when said patient interface system is donned on the patient, the additional pads each comprise an additional pad opening,
   wherein said at least one strap passes through said additional pad opening to allow the additional pads to move freely relative to said at least one strap.

19. The patient interface system of claim 1, wherein each at least one pad comprises a smooth surface on the opening to minimize friction between the at least one pad and the at least one strap.

20. The patient interface system of claim 1, wherein the at least one strap comprises an inelastic material.

21. The patient interface system of claim 1, wherein the joint is constructed from a flexible material.

22. The patient interface system of claim 1, wherein the at least one retractor further comprises a spring configured to tension the at least one strap.

23. The patient interface system of claim 1, wherein the patient interface is nasal pillows.

24. The patient interface system of claim 1, wherein the patient interface is a nasal cushion.

25. The patient interface system of claim 1, wherein the patient interface is a full-face mask.

26. The patient interface system of claim 1, wherein the patient interface is an oro-nasal mask.

27. The patient interface system of claim 1, wherein the seal-forming structure is constructed from a soft, flexible, resilient material.

28. The patient interface system of claim 1, wherein the patient interface further comprises an anti-asphyxia valve.

29. The patient interface system of claim 1, wherein the patient interface further comprises a vent comprising a plurality of holes and being constructed and arranged to washout exhaled carbon dioxide.

30. The patient interface system of claim 1, wherein the patient interface further comprises a connection port configured to connect to an air delivery conduit to deliver pressurized gas to the patient.

31. The patient interface system of claim 30, wherein the patient interface further comprises a decoupling structure configured to connect the air delivery conduit to the connection port.

32. The patient interface system of claim 31, wherein the decoupling structure further comprises a vent comprising a plurality of holes and being constructed and arranged to washout exhaled carbon dioxide.

33. The patient interface system of claim 30, wherein the at least one retractor is fixedly attached to the patient interface at a location laterally outward of the connection port.

* * * * *